(12) United States Patent
Park et al.

(10) Patent No.: US 12,084,433 B2
(45) Date of Patent: *Sep. 10, 2024

(54) HETEROCYCLIC COMPOUND AND ORGANIC LIGHT-EMITTING DEVICE INCLUDING THE SAME

(71) Applicant: Samsung Display Co., Ltd., Yongin-si (KR)

(72) Inventors: Junha Park, Yongin-si (KR); Munki Sim, Yongin-si (KR); Hyoyoung Lee, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 275 days.

This patent is subject to a terminal disclaimer.

(21) Appl. No.: 16/250,946

(22) Filed: Jan. 17, 2019

(65) Prior Publication Data

US 2019/0292169 A1    Sep. 26, 2019

(30) Foreign Application Priority Data

Mar. 23, 2018    (KR) .................. 10-2018-0034091

(51) Int. Cl.
*H10K 50/16*    (2023.01)
*C07D 251/24*    (2006.01)
(Continued)

(52) U.S. Cl.
CPC ......... *C07D 405/04* (2013.01); *C07D 251/24* (2013.01); *C07D 403/04* (2013.01);
(Continued)

(58) Field of Classification Search
CPC ........... H01L 51/50–56; H01L 51/5072; H01L 51/0071; H01L 51/0072; H01L 51/0073;
(Continued)

(56) References Cited

U.S. PATENT DOCUMENTS 5,645,948 A    7/1997   Shi et al.
6,465,115 B2  10/2002   Shi et al.
(Continued)

FOREIGN PATENT DOCUMENTS

CN    105315219 A    2/2016
CN    105315265 A    2/2016
(Continued)

OTHER PUBLICATIONS

WO-2018190522-A1 Machine Translation.*
(Continued)

*Primary Examiner* — Dylan C Kershner
(74) *Attorney, Agent, or Firm* — Lewis Roca Rothgerber Christie LLP

(57) ABSTRACT

Provided are a heterocyclic compound and an organic light-emitting device including the same. The organic light-emitting device includes: a first electrode; a second electrode facing the first electrode; and an organic layer between the first electrode and the second electrode, the organic layer including an emission layer and at least one of the heterocyclic compound.

18 Claims, 2 Drawing Sheets

(51) Int. Cl.
    *C07D 403/04*     (2006.01)
    *C07D 403/10*     (2006.01)
    *C07D 405/04*     (2006.01)
    *C07D 405/10*     (2006.01)
    *C07D 405/14*     (2006.01)
    *C07D 409/04*     (2006.01)
    *C07D 409/10*     (2006.01)
    *C07D 471/04*     (2006.01)
    *C07D 519/00*     (2006.01)
    *H10K 50/125*     (2023.01)
    *H10K 85/60*      (2023.01)

(52) U.S. Cl.
    CPC ......... *C07D 403/10* (2013.01); *C07D 405/10* (2013.01); *C07D 405/14* (2013.01); *C07D 409/04* (2013.01); *C07D 409/10* (2013.01); *C07D 471/04* (2013.01); *C07D 519/00* (2013.01); *H10K 50/16* (2023.02); *H10K 85/626* (2023.02); *H10K 85/6572* (2023.02); *H10K 85/6574* (2023.02); *H10K 85/6576* (2023.02); *H10K 50/125* (2023.02); *H10K 50/166* (2023.02); *H10K 85/654* (2023.02)

(58) Field of Classification Search
    CPC .. H01L 51/0074; H10K 50/16; C07D 405/04; C07D 251/24; C07D 403/10; C07D 405/10; C07D 405/14; C07D 409/04; C07D 409/10; C07D 471/04; C07D 519/00
    See application file for complete search history.

(56) References Cited

U.S. PATENT DOCUMENTS

| | | | |
|---|---|---|---|
| 6,596,415 B2 | 7/2003 | Shi et al. | |
| 6,818,919 B2 | 11/2004 | Robeson et al. | |
| 7,189,989 B2 | 3/2007 | Ise | |
| 7,982,213 B2 | 7/2011 | Okajima et al. | |
| 8,436,344 B2 | 5/2013 | Seo et al. | |
| 8,455,272 B2 | 6/2013 | Sato | |
| 8,999,525 B2 | 4/2015 | Lee et al. | |
| 9,178,001 B2 | 11/2015 | Kwak et al. | |
| 9,252,368 B2 | 2/2016 | Aihara et al. | |
| 9,391,281 B2 | 7/2016 | Lee et al. | |
| 9,425,407 B2 | 8/2016 | Hwang et al. | |
| 9,705,088 B2 | 7/2017 | Park et al. | |
| 9,718,764 B2 | 8/2017 | Stoessel et al. | |
| 9,997,716 B2 | 6/2018 | Zeng et al. | |
| 10,023,599 B2 | 7/2018 | Bierbach et al. | |
| 10,236,452 B2 | 3/2019 | Jeong et al. | |
| 10,249,824 B2 | 4/2019 | Park et al. | |
| 10,297,762 B2 | 5/2019 | Zeng et al. | |
| 10,361,375 B2 | 7/2019 | Zeng et al. | |
| 10,367,147 B2 | 7/2019 | Kim et al. | |
| 10,903,432 B2 | 1/2021 | Sim et al. | |
| 11,152,576 B2 | 10/2021 | Heo et al. | |
| 11,208,402 B2 | 12/2021 | Jung et al. | |
| 11,228,001 B2 | 1/2022 | Heo et al. | |
| 11,370,782 B2 | 6/2022 | Jung et al. | |
| 2002/0132134 A1 | 9/2002 | Hu et al. | |
| 2003/0165715 A1 | 9/2003 | Yoon et al. | |
| 2004/0036077 A1 | 2/2004 | Ise | |
| 2004/0053069 A1 | 3/2004 | Sotoyama et al. | |
| 2004/0137270 A1 | 7/2004 | Seo et al. | |
| 2005/0002857 A1 | 1/2005 | Pez et al. | |
| 2005/0221124 A1 | 10/2005 | Hwang et al. | |
| 2005/0274961 A1 | 12/2005 | Iou | |
| 2006/0252857 A1 | 11/2006 | Schäfer et al. | |
| 2007/0200490 A1 | 8/2007 | Kawamura et al. | |
| 2009/0019768 A1 | 1/2009 | Toseland et al. | |
| 2009/0134784 A1 | 5/2009 | Lin et al. | |
| 2010/0039026 A1 | 2/2010 | Yang et al. | |
| 2010/0155714 A1 | 6/2010 | Seo et al. | |
| 2010/0200883 A1 | 8/2010 | Sato | |
| 2010/0320451 A1 | 12/2010 | Kawamura | |
| 2011/0121268 A1 | 5/2011 | Nagao et al. | |
| 2011/0121274 A1 | 5/2011 | Parham et al. | |
| 2011/0156013 A1 | 6/2011 | Kim et al. | |
| 2011/0198629 A1 | 8/2011 | Lee et al. | |
| 2011/0227053 A1 | 9/2011 | Bae et al. | |
| 2012/0056165 A1 | 3/2012 | Kawamura et al. | |
| 2012/0126692 A1 | 5/2012 | Ise et al. | |
| 2012/0223276 A1 | 9/2012 | Parham et al. | |
| 2012/0256172 A1 | 10/2012 | Ito et al. | |
| 2012/0267620 A1 | 10/2012 | Min et al. | |
| 2012/0286249 A1 | 11/2012 | Lee et al. | |
| 2013/0001526 A1 | 1/2013 | Kwak et al. | |
| 2013/0306959 A1 | 11/2013 | Ikeda et al. | |
| 2013/0306962 A1 | 11/2013 | Yamamoto et al. | |
| 2014/0027754 A1 | 1/2014 | Ueoka et al. | |
| 2014/0138659 A1 | 5/2014 | Shin et al. | |
| 2014/0299192 A1 | 10/2014 | Lee et al. | |
| 2014/0323723 A1 | 10/2014 | Ahn et al. | |
| 2014/0330013 A1 | 11/2014 | Aihara et al. | |
| 2015/0014656 A1 | 1/2015 | Lim et al. | |
| 2015/0041773 A1* | 2/2015 | Park ................... | H10K 85/626 546/159 |
| 2015/0060787 A1 | 3/2015 | Park et al. | |
| 2015/0069342 A1 | 3/2015 | Lee et al. | |
| 2015/0069347 A1 | 3/2015 | Kim et al. | |
| 2015/0069355 A1 | 3/2015 | Hwang et al. | |
| 2015/0171336 A1† | 6/2015 | Park | |
| 2015/0303380 A1 | 10/2015 | Kambe et al. | |
| 2015/0318510 A1 | 11/2015 | Ito et al. | |
| 2015/0349268 A1 | 12/2015 | Zeng et al. | |
| 2016/0028021 A1 | 1/2016 | Zeng et al. | |
| 2016/0043327 A1 | 2/2016 | Yoo et al. | |
| 2016/0046563 A1 | 2/2016 | Stoessel et al. | |
| 2016/0164004 A1 | 6/2016 | Seo et al. | |
| 2016/0197289 A1 | 7/2016 | Sado et al. | |
| 2016/0218298 A1 | 7/2016 | Lee et al. | |
| 2016/0315268 A1 | 10/2016 | Stoessel | |
| 2016/0351817 A1† | 12/2016 | Kim | |
| 2017/0098779 A1 | 4/2017 | Lee et al. | |
| 2017/0200902 A1 | 7/2017 | Lee et al. | |
| 2017/0271596 A1 | 9/2017 | Lee | |
| 2017/0317294 A1 | 11/2017 | Kim et al. | |
| 2018/0051003 A1 | 2/2018 | Koo et al. | |
| 2018/0066180 A1* | 3/2018 | Huh ................... | H10K 50/805 |
| 2018/0102484 A1 | 4/2018 | Mizutani et al. | |
| 2019/0051841 A1* | 2/2019 | Sim ................... | H10K 85/6572 |
| 2019/0198780 A1 | 6/2019 | Kim et al. | |
| 2019/0233398 A1 | 8/2019 | Oh et al. | |
| 2019/0245149 A1† | 8/2019 | Heo | |
| 2019/0263834 A1 | 8/2019 | Jeong et al. | |
| 2019/0341558 A1* | 11/2019 | Yang ................... | H01L 51/0072 |
| 2020/0048232 A1* | 2/2020 | Cha .................... | C07D 401/10 |
| 2020/0131138 A1† | 4/2020 | Han | |
| 2020/0287142 A1* | 9/2020 | Huh ................... | H10K 85/615 |
| 2021/0020848 A1* | 1/2021 | Yang .................. | C07D 405/04 |
| 2021/0119137 A1* | 4/2021 | Cha .................... | C09K 11/06 |

FOREIGN PATENT DOCUMENTS

| | | | |
|---|---|---|---|
| EP | 3072943 A1 | 9/2016 | |
| EP | 3246963 A2 | 11/2017 | |
| JP | 10-17860 A | 1/1998 | |
| JP | 10-338871 A | 12/1998 | |
| JP | 11-87067 A | 3/1999 | |
| JP | 2003045662 A | 2/2003 | |
| JP | 2003-123983 A | 4/2003 | |
| JP | 2004-022334 | 1/2004 | |
| JP | 2004-103576 A | 4/2004 | |
| JP | 2004-107263 A | 4/2004 | |
| JP | 2004-281390 A | 10/2004 | |
| JP | 2007-508275 A | 4/2007 | |
| JP | 4060669 B2 | 3/2008 | |
| JP | 2008-120688 A | 5/2008 | |
| JP | 2009-021336 A | 1/2009 | |
| JP | 2010-141353 A | 6/2010 | |
| JP | 2010-182637 A | 8/2010 | |

(56) References Cited

FOREIGN PATENT DOCUMENTS

| | | |
|---|---|---|
| JP | 2010-195708 A | 9/2010 |
| JP | 2011-012190 A | 1/2011 |
| JP | 2011-49512 A | 3/2011 |
| JP | 2013-100239 A | 5/2013 |
| JP | 2015-504600 A | 2/2015 |
| JP | 2015-524797 A | 8/2015 |
| JP | 2016-6039 A | 1/2016 |
| JP | 2016-19002 A | 2/2016 |
| JP | 2016-516084 A | 6/2016 |
| JP | 2017-31131 A | 2/2017 |
| JP | 2017-509635 A | 4/2017 |
| JP | 2017-107992 A | 6/2017 |
| KR | 10-2003-0067773 A | 8/2003 |
| KR | 10-0525408 B1 | 11/2005 |
| KR | 10-0691543 B1 | 3/2007 |
| KR | 10-2010-056398 A | 5/2010 |
| KR | 10-0958641 | 5/2010 |
| KR | 10-2010-0088612 A | 8/2010 |
| KR | 10-2010-0099327 A | 9/2010 |
| KR | 10-2010-0118690 A | 11/2010 |
| KR | 10-2011-0040874 A | 4/2011 |
| KR | 10-2011-0075690 A | 7/2011 |
| KR | 10-2011-0094271 A | 8/2011 |
| KR | 10-2012-0020901 A | 3/2012 |
| KR | 10-2012-0051598 A | 5/2012 |
| KR | 10-2012-0057198 A | 5/2012 |
| KR | 10-2012-0065214 A | 6/2012 |
| KR | 10-2012-0101558 A | 9/2012 |
| KR | 10-2012-0104087 A | 9/2012 |
| KR | 10-2012-0104246 A | 9/2012 |
| KR | 10-2012-0116838 A | 10/2012 |
| KR | 10-2012-0127683 A | 11/2012 |
| KR | 10-2012-0138671 A | 12/2012 |
| KR | 10-2013-0116041 A | 10/2013 |
| KR | 10-2013-0127567 A | 11/2013 |
| KR | 10-2013-0135181 A | 12/2013 |
| KR | 10-2013-0142969 A | 12/2013 |
| KR | 10-2014-0009918 A | 1/2014 |
| KR | 10-2014-0009919 A | 1/2014 |
| KR | 10-2014-0076520 A | 6/2014 |
| KR | 10-2014-0079306 A | 6/2014 |
| KR | 10-2014-0082351 A | 7/2014 |
| KR | 10-2014-0091049 A | 7/2014 |
| KR | 20140132244 A † | 11/2014 |
| KR | 10-2015-0018229 A | 2/2015 |
| KR | 10-2015-0025259 A | 3/2015 |
| KR | 10-2015-0027897 A | 3/2015 |
| KR | 10-2015-0028860 A | 3/2015 |
| KR | 10-2015-0028935 A | 3/2015 |
| KR | 10-2015-0054797 A | 5/2015 |
| KR | 10-2015-0069346 A | 6/2015 |
| KR | 10-2015-0099750 A | 9/2015 |
| KR | 10-2015-0124000 A | 11/2015 |
| KR | 10-2015-0124637 A | 11/2015 |
| KR | 10-2015-0132873 A | 11/2015 |
| KR | 10-2015-0136579 A | 12/2015 |
| KR | 10-2016-0006633 A | 1/2016 |
| KR | 10-2016-0018332 A | 2/2016 |
| KR | 10-2016-0046046 A | 4/2016 |
| KR | 10-1627691 | 6/2016 |
| KR | 10-2016-0141359 | 12/2016 |
| KR | 10-2017-0023025 A | 3/2017 |
| KR | 10-2017-0032833 A | 3/2017 |
| KR | 10-2017-0049440 A | 5/2017 |
| KR | 10-2017-0104718 | 9/2017 |
| KR | 10-2017-0134264 A | 12/2017 |
| KR | 10-2018-0005533 A | 1/2018 |
| KR | 20180010132 A † | 1/2018 |
| KR | 10-2018-0051355 A | 5/2018 |
| KR | 10-2018-0059286 A | 6/2018 |
| KR | 10-2018-0061075 A | 6/2018 |
| KR | 10-2018-0086126 A | 7/2018 |
| KR | 10-2018-0115217 A | 10/2018 |
| KR | 10-2018-0120569 A | 11/2018 |
| KR | 10-2018-0130329 A | 12/2018 |
| KR | 10-2019-0013527 A | 2/2019 |
| KR | 10-2019-0016638 A | 2/2019 |
| KR | 10-2019-0079341 A | 7/2019 |
| KR | 10-2019-0101882 A | 9/2019 |
| KR | 10-2019-0106753 A | 9/2019 |
| TW | 201100522 A1 | 1/2011 |
| WO | WO 2004/106311 A2 | 12/2004 |
| WO | WO 2010/126270 A1 | 11/2010 |
| WO | WO 2010/015306 A1 | 2/2012 |
| WO | WO 2012/086170 A1 | 6/2012 |
| WO | WO 2012/173073 A1 | 12/2012 |
| WO | WO 2014/104720 A1 | 7/2014 |
| WO | WO 2016/002864 A1 | 1/2016 |
| WO | WO 2016/121597 A1 | 8/2016 |
| WO | WO-2018190522 A1 * | 10/2018 ........... C07D 401/14 |
| WO | WO-2018199466 A1 * | 11/2018 ........... C07D 307/91 |

OTHER PUBLICATIONS

Hatalis, et al. "Polysilicon TFT active matrix organic EL displays." Cockpit Displays IV: Flat Panel Displays for Defense Applications. vol. 3057. SPIE, 1997.*

D'Andrade, et al. "Controlling exciton diffusion in multilayer white phosphorescent organic light emitting devices." Advanced Materials 14.2 (2002): 147-151.*

Adachi, Chihaya, et al., "Confinement of charge carriers and molecular excitons within 5-nm-thick emitter layer in organic electroluminescent devices with a double heterostructure," Applied Physics Letters, 57 (6), Aug. 6, 1990, 5 pages.

Johansson, Nicklas, et al., "Solid-State Amplified Spontaneous Emission in Some Spiro-Type Molecules: A New Concept for the Design of Solid-State Lasing Molecules," Advanced Materials, vol. 10, No. 14, 1998, pp. 1136-1141.

Sakamoto, Youichi, et al., "Synthesis, Characterization, and Electron-Transport Property of Perfluorinated Phenylene Dendrimers," J. Am. Chem. Soc., vol. 122, No. 8, 2000, pp. 1832-1833.

Tang, C.W., et al., "Organic electroluminescent diodes," Appl. Phys. Lett., vol. 51, No. 12, Sep. 21, 1987, pp. 913-915.

Tao, Y.T., et al., "Sharp green electroluminescence from 1H-pyrazolo[3,4-b]quinoline-based light-emitting diodes," Applied Physics Letters, vol. 77, No. 11, Sep. 11, 2000, 4 pages.

Yamaguchi, Shigehiro, et al. "Diphenylamino-Substituted 2,5-Diarylsiloles for Single-Layer Organic Electroluminescent Devices," Chemistry Letters, 2001, pp. 98-99.

Berger, Ricarda, et al., "New symmetrically substituted 1,3,5-triazines as host compounds for channel-type inclusion formation," CrystEngComm, 2012, vol. 14, 3 pages.

Debnath, Pradip, et al., "A novel straightforward synthesis of 2,4,6-triaryl-1,3,5-triazines via copper-catalyzed cyclization of N-benzylbenzamidines," Tetrahedron Letters, 2014, vol. 55, 3 pages.

Ishi-I, Tsutomu, et al., "High Electron Drift Mobility in an Amorphous Film of 2,4,6,-Tris[4-(1-naphthyl)phenyl]-1,3,5-triazine," Chemistry Letters, 2004, vol. 33, No. 10, 2 pages.

Kotha, Sambasivarao, et al., "Synthesis of nano-sized C3-symmetric 2,4,6-triphenyl-1,3,5-s-triazine and 1,3,5-triphenylbenzene derivatives via the trimerization followed by Suzuki-Miyaura cross-coupling or O-alkylation reactions and their biological evaluation," Indian Journal of Chemistry, Dec. 2009, vol. 48B, 5 pages.

Kwon, Jang Hyeok et al., "Preparation of phenanthroline derivatives for organic electric device," Sep. 18, 2017, XP002782646.

Lee, Dong Ryun, et al., "Design Strategy for 25% External Quantum Efficiency in Green and Blue Thermally Activated Delayed Fluorescent Devices," Advanced Materials, 2015, vol. 27, 7 pages.

Tong et al; Light-Driven Proton Reduction in Aqueous Medium Catalyzed by a Family of Cobalt Complexes with Tetradentate Polyoyridine-Type Ligands, 2015, Inorganic Chemistry, 54, 7873-7884. (Year: 2015).

Zeika, Olaf, et al., "Synthesis of Polynitroxides Based on Nucleophilic Aromatic Substitution," Organic Letters, 2010, vol. 12, No. 16, 4 pages.

Internet Material: 2009 Fall Assembly and Symposium. Vol. 34, No. 2, 2009; Publication Date, Oct. 8, 2009-Oct. 9, 2009; Title: A novel conjugated polymer based on 4H-benzo[det]carbazole backbone for OLED, 1 page.

(56) References Cited

OTHER PUBLICATIONS

Swensen et al.; Blue phosphorescent organic light-emitting devices utilizing cesium-carbonate-doped 2,4,6-tris(2',4'-difluoro-[1,1'-biphenyl]-4-yl)-1,3,5-triazine; Journal of Photonics for Energy (2011), 1, 011008/1-011008/11 (Year: 2011).
EPO Extended Search Report dated Jul. 11, 2018, for corresponding European Patent Application No. 18175088.6 (8 pages).
EPO Extended Search Report dated Sep. 21, 2018, for corresponding European Patent Application No. 18178734.2 (11 pages).
Machine translation of JP 2003045662, translation generated Feb. 2020, 70 pages. (Year: 2020).
"Fused pyridine derivatives," Heterocycles, vol. 57, 2002, 1 page.
Rahman, A.F.M. Motiur, et al., "Synthesis and Properties of Benzo[b]-1,10-phenanthrolines and Their Ruthenium(II) Complexes," Heteroatom Chemistry, vol. 18, No. 6, 2007, pp. 650-656.
Heterocycles, vol. 78, No. 6, 2009, 7 pages.
Jahng, Yurngdong, et al., "Synthesis and Properties of 2,2'-Di(heteroaryl)-9,9'-spirobifluorenes," Bulletin of the Chemical Society of Japan, vol. 83, No. 6, 2010, pp. 672-677.
U.S. Notice of Allowance from U.S. Appl. No. 15/866,885, dated Jun. 29, 2021, 10 pages.
U.S. Notice of Allowance from U.S. Appl. No. 15/867,357, dated Mar. 31, 2021, 10 pages.
U.S. Office Action from U.S. Appl. No. 14/198,372, dated Dec. 10, 2015, 7 pages.
U.S. Office Action from U.S. Appl. No. 14/290,950, dated Oct. 6, 2016, 7 pages.
U.S. Office Action from U.S. Appl. No. 15/866,885, dated Apr. 15, 2020, 12 pages.
U.S. Office Action from U.S. Appl. No. 15/866,885, dated Jan. 28, 2021, 10 pages.
U.S. Office Action from U.S. Appl. No. 15/867,357, dated Dec. 9, 2020, 12 pages.
U.S. Office Action from U.S. Appl. No. 15/867,357, dated Feb. 20, 2020, 8 pages.
U.S. Office Action from U.S. Appl. No. 15/867,357, dated Jun. 25, 2020, 9 pages.
U.S. Office Action from U.S. Appl. No. 15/867,357, dated Sep. 16, 2021, 9 pages.
U.S. Office Action from U.S. Appl. No. 15/913,162, dated Jun. 15, 2020, 9 pages.
U.S. Office Action from U.S. Appl. No. 15/913,162, dated Mar. 6, 2020, 9 pages.
U.S. Advisory Action from U.S. Appl. No. 15/866,885, dated Nov. 9, 2020, 2 pages.
U.S. Advisory Action from U.S. Appl. No. 15/867,357, dated Aug. 17, 2020, 3 pages.
U.S. Notice of Allowance from U.S. Appl. No. 14/198,372, dated Apr. 13, 2016, 9 pages.
U.S. Notice of Allowance from U.S. Appl. No. 14/290,950, dated Mar. 9, 2017, 8 pages.
U.S. Notice of Allowance from U.S. Appl. No. 15/866,885, dated Apr. 15, 2022, 27 pages.
U.S. Notice of Allowance from U.S. Appl. No. 15/866,885, dated Nov. 10, 2021, 27 pages.
U.S. Notice of Allowance from U.S. Appl. No. 15/867,357, dated Apr. 4, 2022, 8 pages.
U.S. Notice of Allowance from U.S. Appl. No. 15/913,162, dated Aug. 12, 2020, 5 pages.
U.S. Office Action from U.S. Appl. No. 15/866,885, dated Sep. 2, 2020, 12 pages.
U.S. Restriction Requirement from U.S. Appl. No. 15/866,885, dated Jan. 13, 2020, 7 pages.
Chinese Office Action dated Jan. 18, 2022, issued in Chinese Patent Application No. 201810652269.6 (9 pages).
U.S. Final Office Action dated Feb. 3, 2022, issued in U.S. Appl. No. 15/867,357 (9 pages).
Fink, Ralf et al., "Aromatic polyethers with 1,3,5-triazine units as hole-blocking/elecgtron-transport materials in LEDs," Proceedings of SPIE, vol. 3148, 1997, 9 pages.
Japanese Office Action dated Jun. 7, 2022, issued in Japanese Patent Application No. 2018-117229, 5 pages.
U.S. Notice of Allowance dated Aug. 29, 2022, issued in U.S. Appl. No. 15/867,357 (10 pages).
Korean Notice of Allowance, for Patent Application No. 10-2017-0100434, dated Mar. 23, 2022, 6 pages.
Notice of Allowance for U.S. Appl. No. 15/866,885 dated Oct. 21, 2022, 27 pages.
Office Action for U.S. Appl. No. 17/395,913 dated Jan. 20, 2023, 12 pages.
Notice of Allowance dated Feb. 21, 2023 issued in corresponding KR Patent Application No. 10-2018-0034091, 2pp.
US Final Office Action dated May 25, 2023, issued in U.S. Appl. No. 17/395,913 (8 pages).
US Notice of Allowance dated Jul. 28, 2023, issued in U.S. Appl. No. 17/395,913 (8 pages).

\* cited by examiner
† cited by third party

| 190 |
| --- |
| 150 |
| 110 |

| 190 |
| --- |
| 150 |
| 110 |
| 210 |

| 220 |
|---|
| 190 |
| 150 |
| 110 |

| 220 |
|---|
| 190 |
| 150 |
| 110 |
| 210 |

HETEROCYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2018-0034091, filed on Mar. 23, 2018, in the Korean Intellectual Property Office, the entire content of which is incorporated herein by reference.

BACKGROUND

1. Field

One or more embodiments of the present disclosure relate to a heterocyclic compound for an organic light-emitting device and an organic light-emitting device including the same.

2. Description of the Related Art

Organic light-emitting devices are self-emission devices that have wide viewing angles, high contrast ratios, short response times, and excellent characteristics in terms of brightness, driving voltage, and response speed, compared to other devices in the art.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

Aspects of embodiments of the present disclosure provide heterocyclic compound having a novel structure and an organic light-emitting device including the same.

Additional aspects of embodiments of the present disclosure will be set forth in part in the description which follows and, in part, will be apparent from the description, or may be learned by practice of the presented embodiments.

An aspect of an embodiment provides a heterocyclic compound represented by Formula 1:

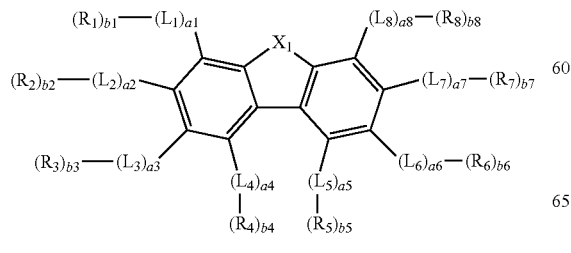

Formula 1

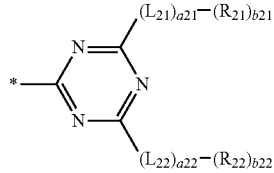

Formula 2-1

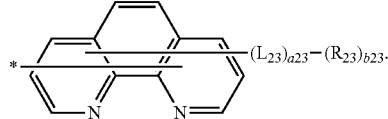

Formula 2-2

In Formulae 1, 2-1, and 2-2, $X_1$ may be selected from $C(R_{11})(R_{12})$, $Si(R_{13})(R_{14})$, $N(R_{15})$, O, and S, $L_1$ to $L_8$ and $L_{21}$ to $L_{23}$ may each independently be a single bond, a substituted or unsubstituted, a $C_3$-$C_{60}$ carbocyclic group, or a substituted or unsubstituted $C_1$-$C_{60}$ heterocyclic group, a1 to a8 and a21 to a23 may each independently be an integer of 1 to 5, wherein, when a1 is two or more, two more of $L_1$(s) may be identical to or different from each other, when a2 is two or more, two more of $L_2$(s) may be identical to or different from each other, when a3 is two or more, two more of $L_3$(s) may be identical to or different from each other, when a4 is two or more, two more of $L_4$(s) may be identical to or different from each other, when a5 is two or more, two more of $L_5$(s) may be identical to or different from each other, when a6 is two or more, two more of $L_6$(s) may be identical to or different from each other, when a7 is two or more, two more of $L_7$(s) may be identical to or different from each other, when a8 is two or more, two more of $L_8$(s) may be identical to or different from each other, when a21 is two or more, two more of $L_{21}$(s) may be identical to or different from each other, when a22 is two or more, two more of $L_{22}$(s) may be identical to or different from each other, and when a23 is two or more, two more of $L_{23}$(S) may be identical to or different from each other, $R_1$ to $R_8$ and $R_{11}$ to $R_{15}$ may each independently be selected from a group represented by Formula 2-1, a group represented by Formula 2-2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, at least one selected from $R_1$ to $R_8$ may be a cyano group or a cyano group-containing carbocyclic group, and at least one of the remaining $R_1$ to $R_8$ may be a group represented by Formula 2-1 or a group represented by Formula 2-2, when $X_1$ in Formula 1 is $C(R_{11})(R_{12})$, at least one selected from $R_1$ to $R_8$ may be a cyano group-containing carbocyclic group, and $R_{11}$ and $R_{12}$ may not be simultaneously —F, $R_{11}$ and $R_{12}$ may optionally be linked with each other via a single bond, $R_{21}$ to $R_{23}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, wherein $R_{23}$ may not be a cyano group, b1 to b8 and b21 to b23 may each independently be an integer of 1 to 5, wherein, when b1 is two or more, two more of $R_1$(s) may be identical to or different from each other, when b2 is two or more, two more of $R_2$(s) may be identical to or different from each other, when b3 is two or more, two more of $R_3$(s) may be identical to or different from each other, when b4 is two or more, two more of $R_4$(s) may be identical to or different from each other, when b5 is two or more, two more of $R_5$(s) may be identical to or different from each other, when b6 is two or more, two more of $R_6$(s) may be identical to or different from each other, when b7 is two or more, two more of $R_7$(s) may be identical to or different from each other, when b8 is two or more, two more of $R_8$(s) may be identical to or different from each other, when b21 is two or more, two more of $R_{21}$(s) may be identical to or different from each other, when b22 is two or more, two more of $R_{22}$(s) may be identical to or different from each other, and when b23 is two or more, two more of $R_{23}$(s) may be identical to or different from each other, $R_1$ to $R_8$, $R_{11}$ to $R_{15}$, $R_{21}$ to $R_{23}$, $L_1$ to $L_8$, and $L_{21}$ to $L_{23}$ may not include a carbazole group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Another aspect of an embodiment of the present disclosure provides an organic light-emitting device including: a first electrode; a second electrode facing the first electrode; and an organic layer between the first electrode and the second electrode, wherein the organic layer includes an emission layer and at least one of the heterocyclic compound.

Another aspect of an embodiment of the present disclosure provides an electronic apparatus including: a thin film transistor including a source electrode, a drain electrode, an activation layer, and a gate electrode; and the organic light-emitting device, wherein the first electrode of the organic light-emitting device is electrically connected to one of the source electrode and the drain electrode of the thin film transistor.

BRIEF DESCRIPTION OF THE DRAWING

These and/or other aspects will become apparent and more readily appreciated from the following description of the embodiments, taken in conjunction with the accompanying drawings in which:

FIGS. 1-4 are each a schematic cross-sectional view of an organic light-emitting device according to an embodiment.

DETAILED DESCRIPTION

Reference will now be made in more detail to embodiments of the present disclosure, examples of which are illustrated in the accompanying drawings, wherein like reference numerals refer to like elements throughout. In this regard, the present embodiments may have different forms and should not be construed as being limited to the descriptions set forth herein. In the drawings, the relative sizes of elements, layers, and regions may be exaggerated for clarity. Accordingly, the embodiments are merely described below, by referring to the figures, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list.

An aspect of the present disclosure provides a heterocyclic compound represented by Formula 1:

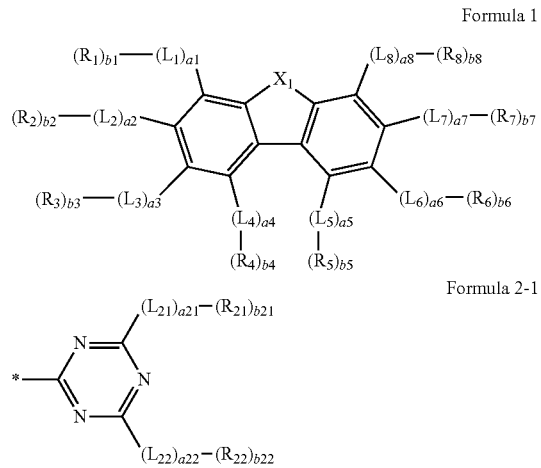

Formula 1

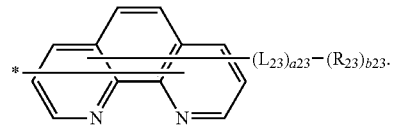

Formula 2-2

Formulae 1, 2-1, and 2-2 will be described in more detail below.

In Formula 1, $X_1$ may be selected from $C(R_{11})(R_{12})$, $Si(R_{13})(R_{14})$, $N(R_{15})$, O, and S.

In one embodiment, $X_1$ may be selected from $C(R_{11})(R_{12})$, $N(R_{15})$, O, and S.

In Formulae 1, 2-1, and 2-2, $L_1$ to $L_8$ and $L_{21}$ to $L_{23}$ may each independently be a single bond, a substituted or unsubstituted, a $C_3$-$C_{60}$ carbocyclic group, or a substituted or unsubstituted $C_1$-$C_{60}$ heterocyclic group.

In one embodiment, $L_1$ to $L_8$ and $L_{21}$ to $L_{23}$ may each independently be selected from:

a benzene group, a pentalene group, an indene group, an azulene group, a heptalene group, an indacene group, an acenaphthene group, a fluorene group, a spirofluorene group, a benzofluorene group, a dibenzofluorene group, a phenalene group, a phenanthrene group, an anthracene group, a fluoranthene group, a triphenylene group, a pyrene group, a chrysene group, a naphthacene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an indole group, an isoindole group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a triazole group, a tetrazole group, an oxadiazole group, a triazine group, a dibenzofuran group, and a dibenzothiophene group; and a benzene group, a pentalene group, an indene group, an azulene group, a heptalene group, an indacene group, an acenaphthene group, a fluorene group, a spirofluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a rubicene group, a coronene group, an ovalene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an indole group, an isoindole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a triazole group, a tetrazole group, an oxadiazole group, a triazine group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, and a dibenzothiophenyl group, but embodiments of the present disclosure are not limited thereto.

For example, $L_1$ to $L_8$ and $L_{21}$ to $L_{23}$ may each independently be selected from groups represented by Formulae 3-1 to 3-26:

3-1
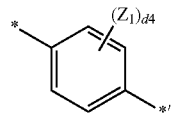

3-2
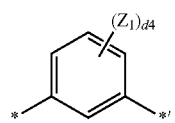

3-3
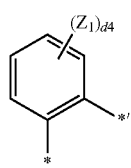

3-4
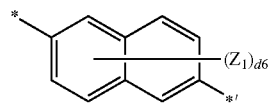

-continued 3-5
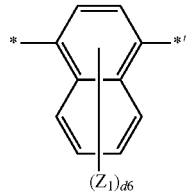

3-6
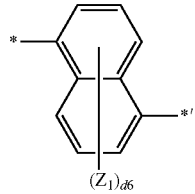

3-7
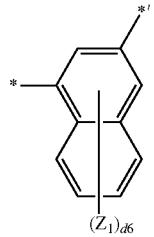

3-8
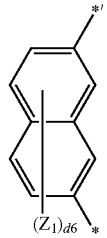

3-9
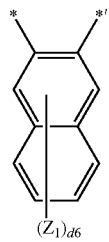

3-10
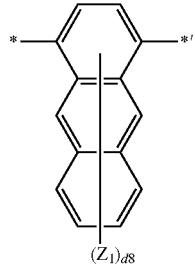

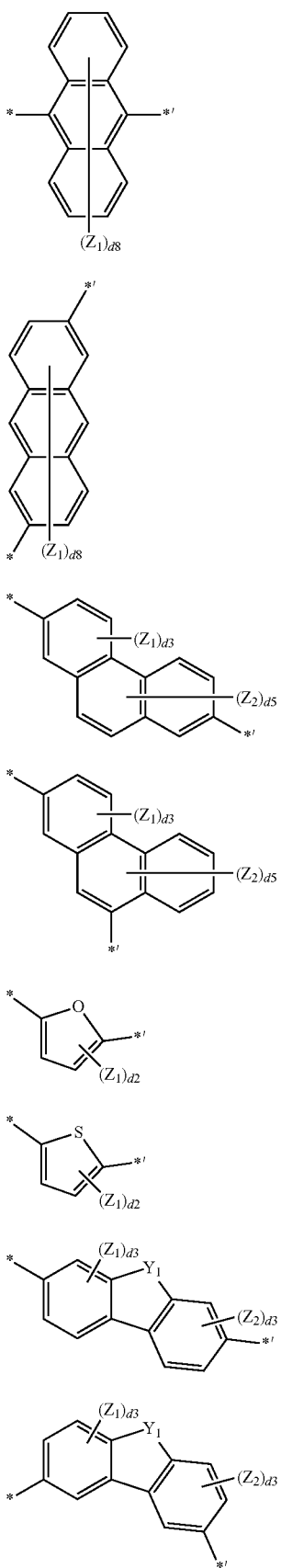
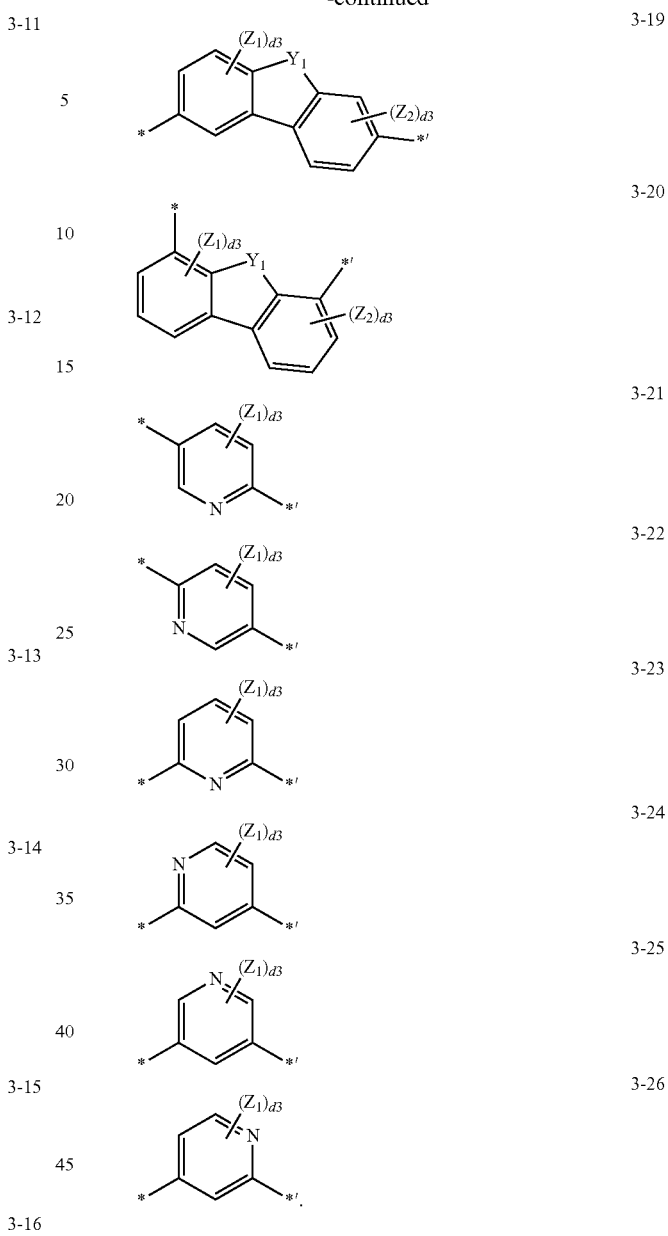

In Formulae 3-1 to 3-26, $Y_1$ may be O, S, $C(Z_3)(Z_4)$, or $Si(Z_6)(Z_7)$, $Z_1$ to $Z_7$ may each independently be selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, and a dibenzothiophenyl group, d2 may be an integer of 0 to 2,
d3 may be an integer 0 to 3,
d4 may be an integer 0 to 4,
d5 may be an integer 0 to 5,
d6 may be an integer 0 to 6,
d8 may be an integer 0 to 8, and
* and *' each indicate a binding site to a neighboring atom.

In Formulae 1, 2-1, and 2-2, a1 to a8 and a21 to a23 may each independently be an integer of 1 to 5. When a1 is two or more, two more of $L_1(s)$ may be identical to or different from each other, when a2 is two or more, two more of $L_2(s)$ may be identical to or different from each other, when a3 is two or more, two more of $L_3(s)$ may be identical to or different from each other, when a4 is two or more, two more of $L_4(s)$ may be identical to or different from each other, when a5 is two or more, two more of $L_5(s)$ may be identical to or different from each other, when a6 is two or more, two more of $L_6(s)$ may be identical to or different from each other, when a7 is two or more, two more of $L_7(s)$ may be identical to or different from each other, when a8 is two or more, two more of $L_8(s)$ may be identical to or different from each other, when a21 is two or more, two more of $L_{21}(s)$ may be identical to or different from each other, when a22 is two or more, two more of $L_{22}(s)$ may be identical to or different from each other, and when a23 is two or more, two more of $L_{23}(s)$ may be identical to or different from each other.

In one embodiment, a1 to a8 and a21 to a23 may each independently be an integer of 1 to 3, but embodiments of the present disclosure are not limited thereto.

For example, a1 to a8 and a21 to a23 may each independently be 1 or 2.

In Formula 1, $R_1$ to $R_8$ and $R_{11}$ to $R_{15}$ may each independently be a group represented by Formula 2-1, a group represented by Formula 2-2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein at least one selected from $R_1$ to $R_8$ may be a cyano group or a cyano group-containing carbocyclic group, and at least one of the rest of $R_1$ to $R_8$ may be a group represented by Formula 2-1 or a group represented by Formula 2-2.

In Formula 1, when $X_1$ is C($R_{11}$)($R_{12}$), at least one selected from $R_1$ to $R_8$ may be a cyano group-containing carbocyclic group, wherein $R_{11}$ and $R_{12}$ may not be simultaneously-F, and $R_{11}$ and $R_{12}$ may optionally be linked each other via a single bond.

In one embodiment, $R_1$ to $R_8$ and $R_{11}$ to $R_{13}$ may each independently be selected from:

a group represented by Formula 2-1, a group represented by Formula 2-2, hydrogen, deuterium, —F, —Cl, —Br, —I, a hydroxyl group, a cyano group, a nitro group, an amidino group, a hydrazino group, a hydrazono group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, and a dibenzosilolyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, and a dibenzosilolyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, and $Q_{31}$ to $Q_{33}$ may each independently be selected from:
a $C_1$-$C_{20}$ alkyl group, a $C_1$-$C_{20}$ alkoxy group, a phenyl group, a biphenyl group, and a terphenyl group; and
a phenyl group substituted with at least one selected from deuterium, —F, —Cl, —Br, —I, a cyano group, a $C_1$-$C_{20}$ alkyl group, and a $C_1$-$C_{20}$ alkoxy group.

The cyano group-containing cyclic compound refers to a group in which at least one hydrogen of a cyclic group is substituted with a cyano group.

In one embodiment, the cyano group-containing cyclic compound may be selected from:
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, and a dibenzosilolyl group, each substituted with at least one cyano group.

For example, the term "a phenyl group in which at least one cyano group is substituted," as used herein, refers to a phenyl group in which at least one hydrogen thereof is substituted with a cyano group; or a phenyl group in which some of at least one hydrogen thereof are substituted with a cyano group, and the rest of the at least one hydrogen thereof are substituted with a group other than a cyano group (for example, a methyl group, an ethyl group, or halogen). For example, a phenyl group including at least one cyano group as a substituent, such a substituted phenyl group may include a phenyl group in which two cyano groups are substituted, a phenyl group in which two cyano groups are substituted, and a phenyl group in which two cyano groups and one methyl group are substituted.

In one embodiment, the cyano group-containing cyclic compound may be selected from groups represented by Formulae 4-1 to 4-16:

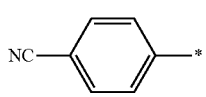

4-1

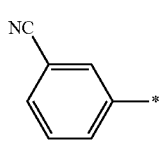

4-2

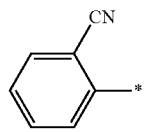

4-3

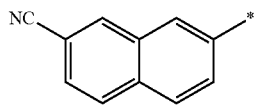

4-4

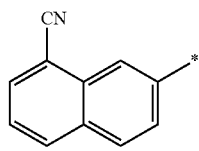

4-5

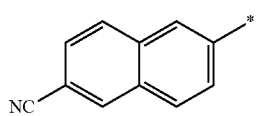

4-6

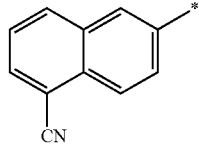

4-7

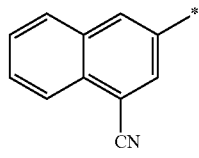

4-8

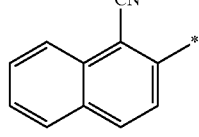

4-9

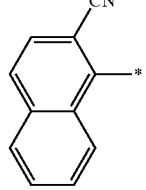

4-10

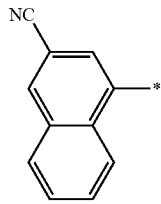

4-11

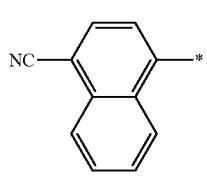

4-12

-continued

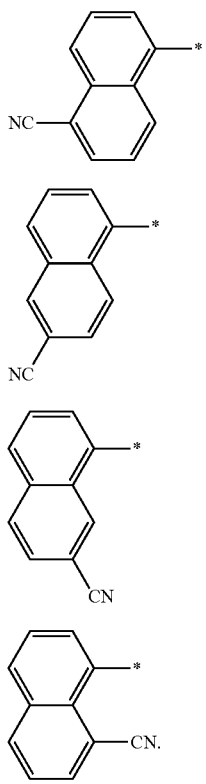

4-13

4-14

4-15

4-16

In Formulae 4-1 to 4-16, * indicates a binding site to a neighboring atom.

In Formulae 2-1 to 2-3, $R_{21}$ to $R_{23}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $R_{23}$ may not be a cyano group.

In one embodiment, $R_{21}$ to $R_{23}$ may each independently be selected from:

a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, and an imidazopyridinyl group;

a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, an imidazopyridinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $R_{23}$ may not include a cyano group.

In Formulae 1, 2-1, and 2-2, b1 to b8 and b21 to b23 may each independently be an integer of 1 to 5, and when b1 is two or more, two more of R$_1$(s) may be identical to or different from each other, when b2 is two or more, two more of R$_2$(s) may be identical to or different from each other, when b3 is two or more, two more of R$_3$(s) may be identical to or different from each other, when b4 is two or more, two more of R$_4$(s) may be identical to or different from each other, when b5 is two or more, two more of R$_5$(s) may be identical to or different from each other, when b6 is two or more, two more of R$_6$(s) may be identical to or different from each other, when b7 is two or more, two more of R$_7$(s) may be identical to or different from each other, when b8 is two or more, two more of R$_8$(s) may be identical to or different from each other, when b21 is two or more, two more of R$_{21}$(s) may be identical to or different from each other, when b22 is two or more, two more of R$_{22}$(S) may be identical to or different from each other, and when b23 is two or more, two more of R$_{23}$(s) may be identical to or different from each other.

In one embodiment, b1 to b8 and b21 to b23 may each independently be an integer of 1 to 3, but embodiments of the present disclosure are not limited thereto.

In Formulae 1, 2-1, and 2-2, R$_1$ to R$_8$, R$_{11}$ to R$_{15}$, R$_{21}$ to R$_{23}$, L$_1$ to L$_8$, and L$_{21}$ to L$_{23}$ may not each include a carbazole group. The heterocyclic compound represented by Formula 1 may not include a carbazole group, except in the case where X$_1$ is N(R$_{15}$).

In Formula 1, at least one of R$_6$ and R$_7$ may be a group represented by Formula 2-1 or 2-2, and at least one selected from R$_1$, R$_2$, R$_3$, R$_4$, R$_5$, R$_7$, and R$_8$ may be a cyano group or a cyano group-containing carbocyclic group.

In one embodiment, at least one of R$_6$ and R$_7$ may be a group represented by Formula 2-1 or 2-2, and at least one selected from R$_1$, R$_2$, R$_3$, and R$_4$ may be a cyano group or a cyano group-containing carbocyclic group.

For example, R$_6$ may be a group represented by Formula 2-1 or 2-2, and at least one selected from R$_1$, R$_2$, R$_3$, and R$_4$ may be a cyano group or a cyano group-containing carbocyclic group.

For example, R$_7$ may be a group represented by Formula 2-1 or 2-2, and at least one selected from R$_1$, R$_2$, R$_3$, and R$_4$ may be a cyano group or a cyano group-containing carbocyclic group.

For example, R$_6$ may be a group represented by Formula 2-1 or 2-2, and at least one selected from R$_5$, R$_7$, and R$_8$ may be a cyano group or a cyano group-containing carbocyclic group.

For example, R$_7$ may be a group represented by Formula 2-1 or 2-2, and at least one selected from R$_5$, R$_6$, and R$_8$ may be a cyano group or a cyano group-containing carbocyclic group.

In Formula 1, at least one selected from R$_2$, R$_3$, and R$_8$ may be a cyano group or a cyano group-containing cyclic group.

Formula 2-2 may be represented by one selected from Formulae 2-2(1) to 2-2(4):

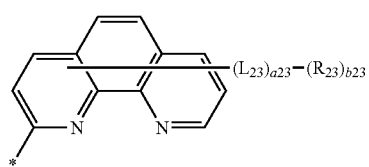

In Formulae 2-2(1) to 2-2(4),

L$_{23}$, a23, R$_{23}$, and b23 may respectively be the same as defined above.

The heterocyclic compound represented by Formula 1 may be selected from Compounds 1 to 95:

3
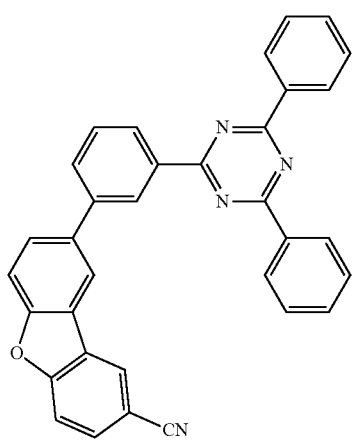
4
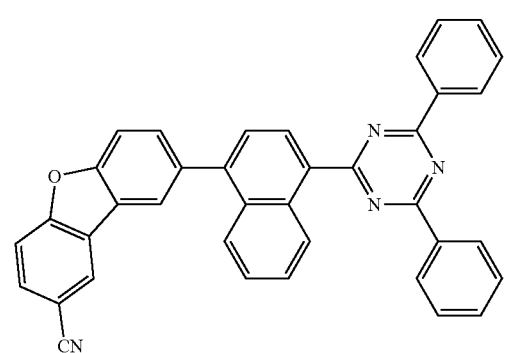
5
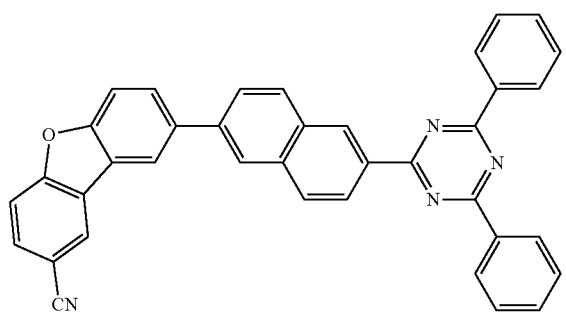
6
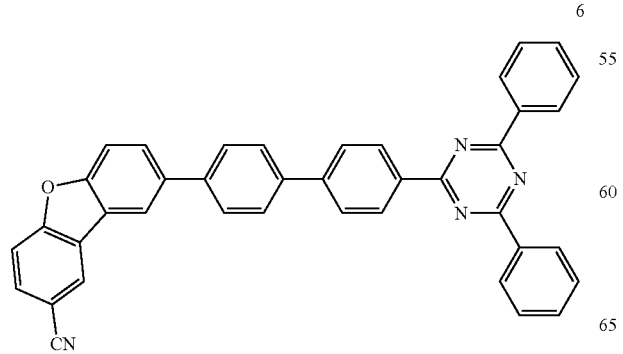
7
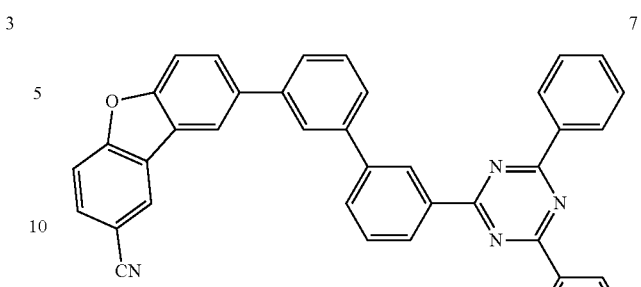
8
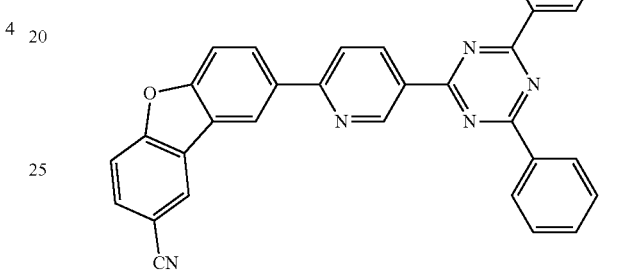
9
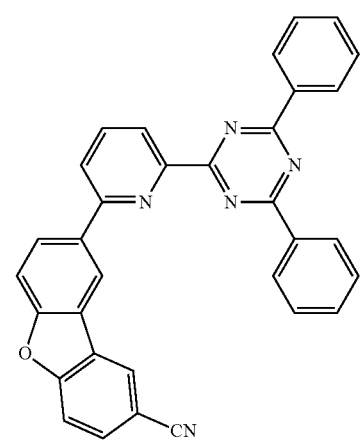
10
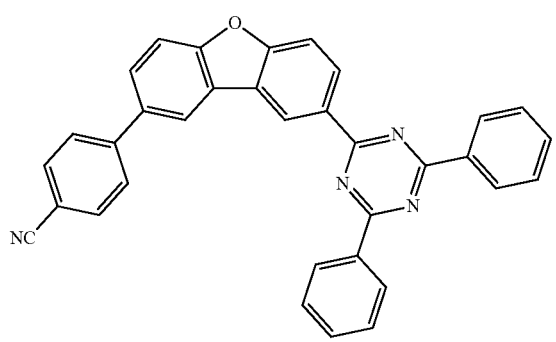

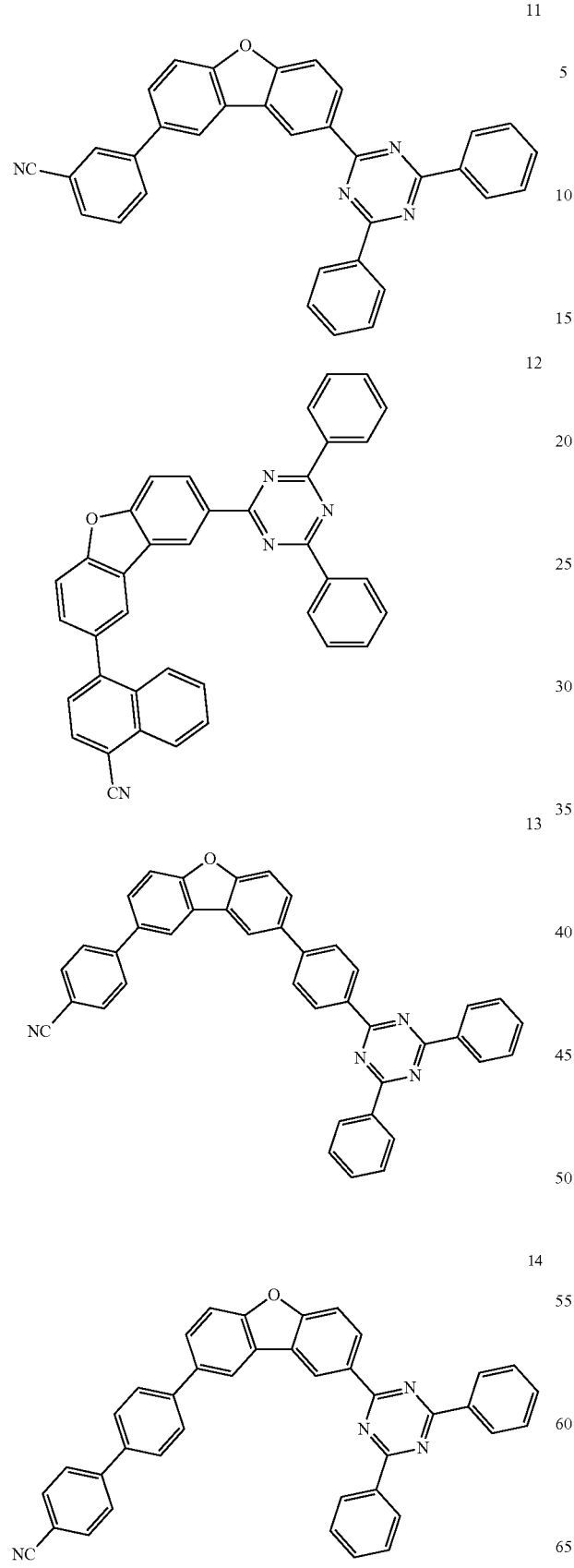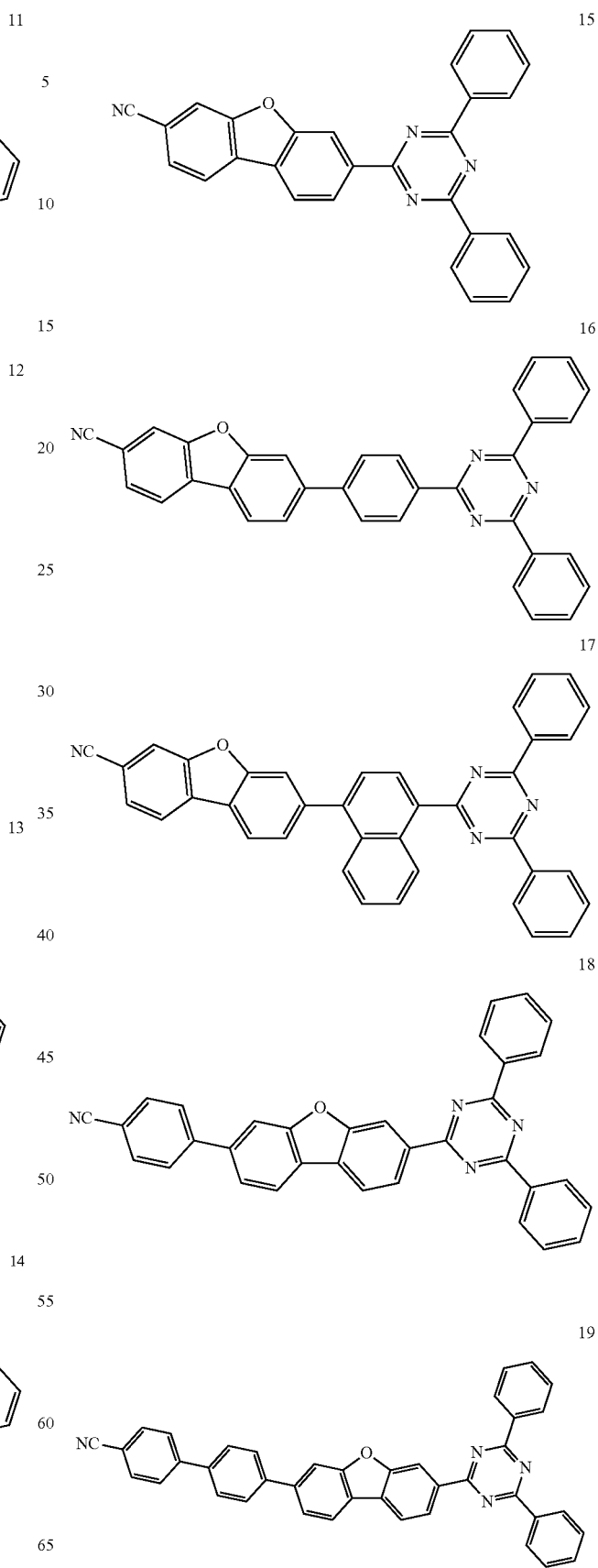

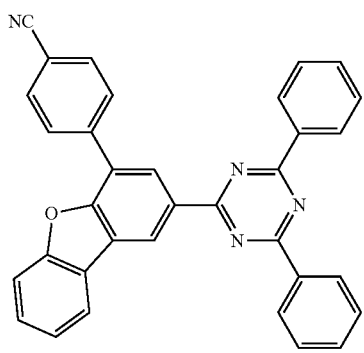
20
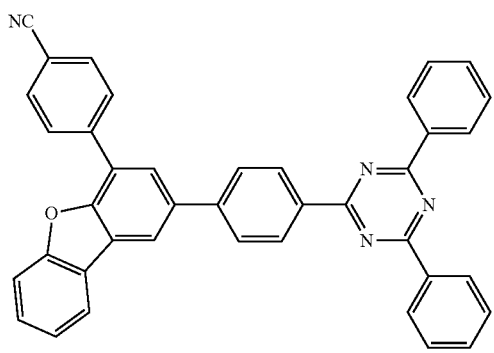
21
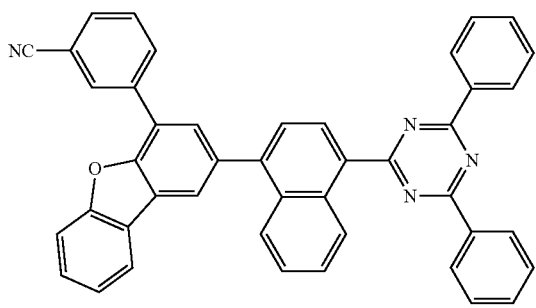
22
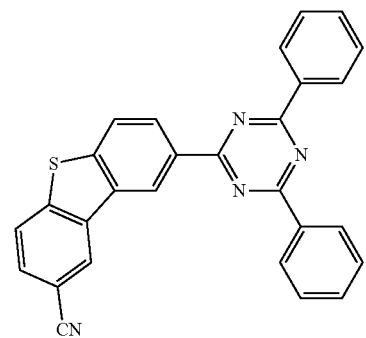
23
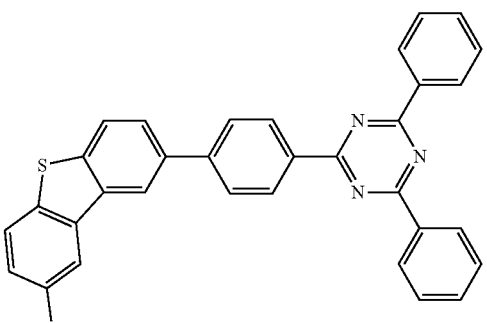
24
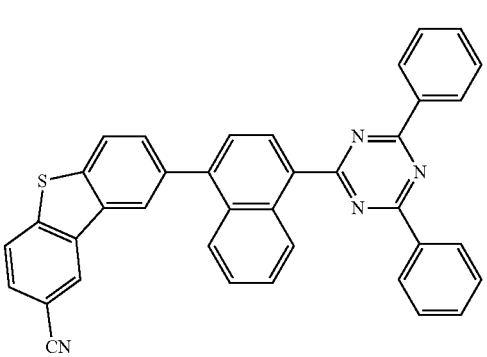
25
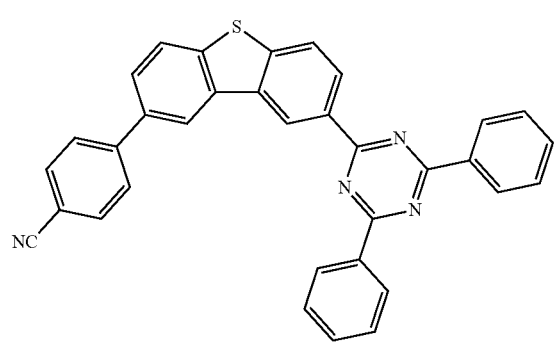
26
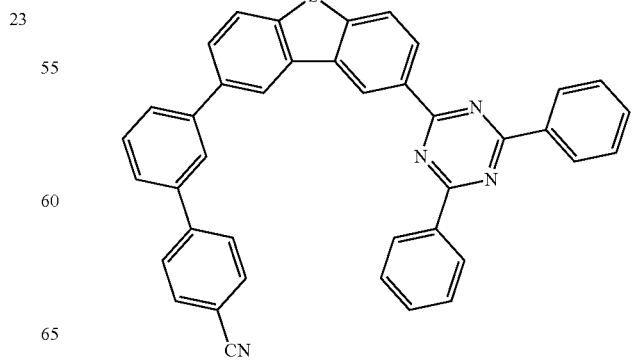
27

28
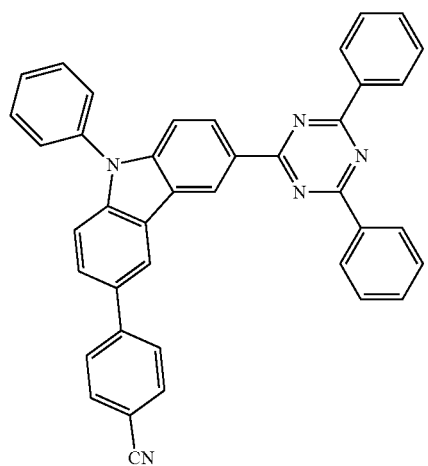
29
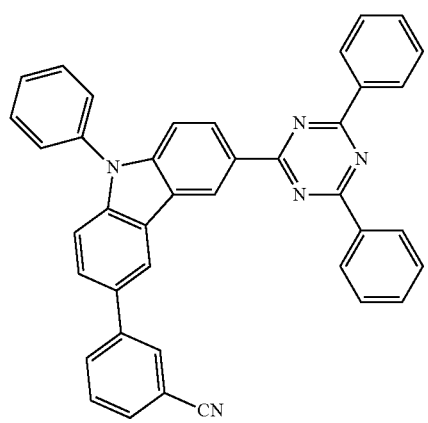
30
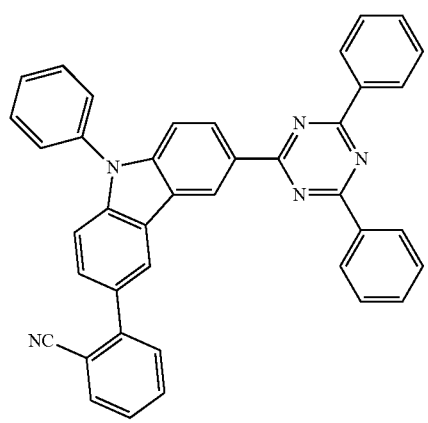
31
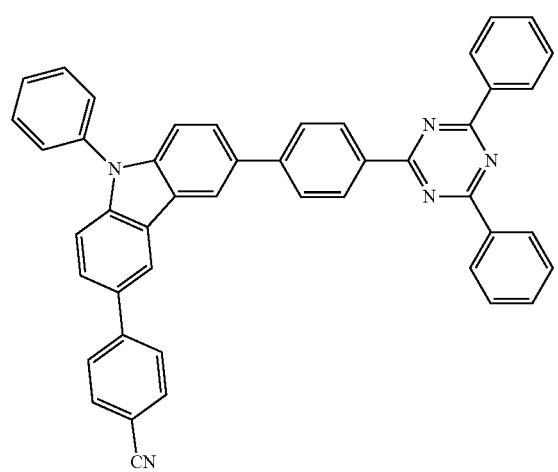
32
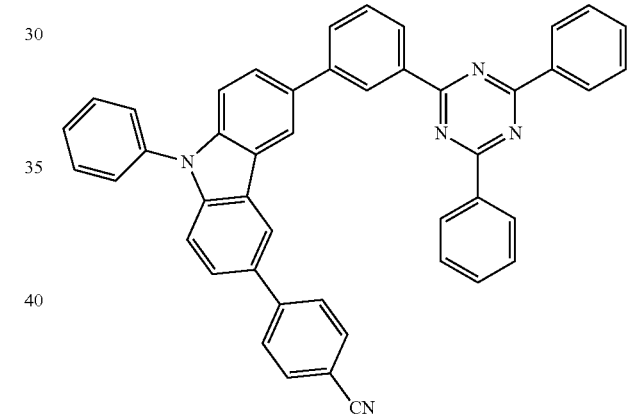
33
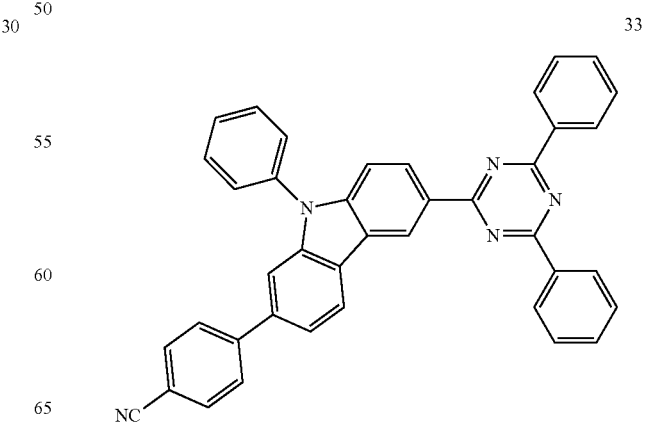

34
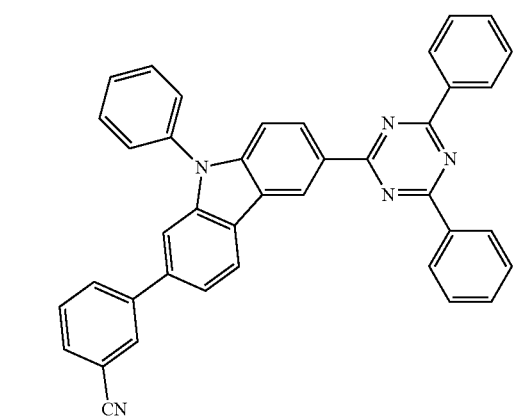
35
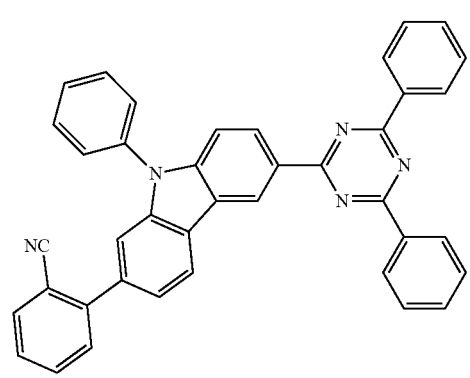
36
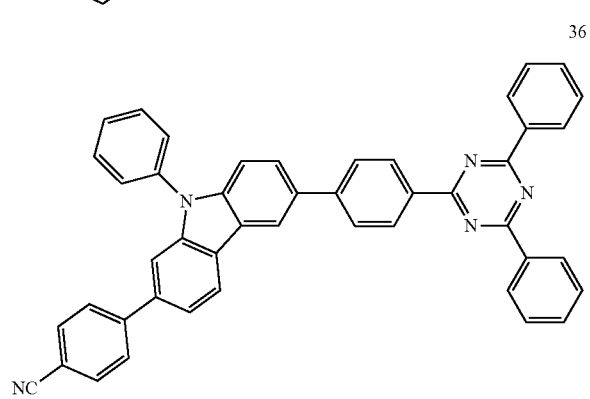
37
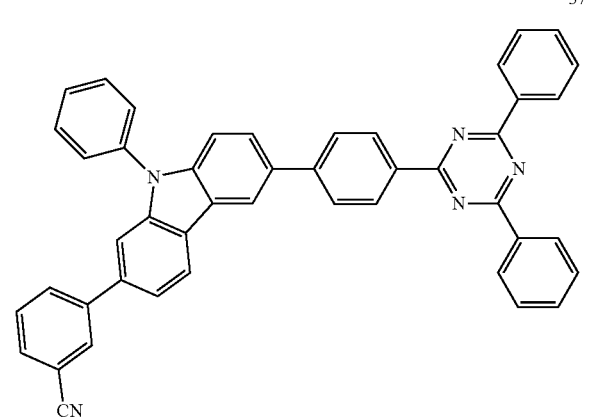
38
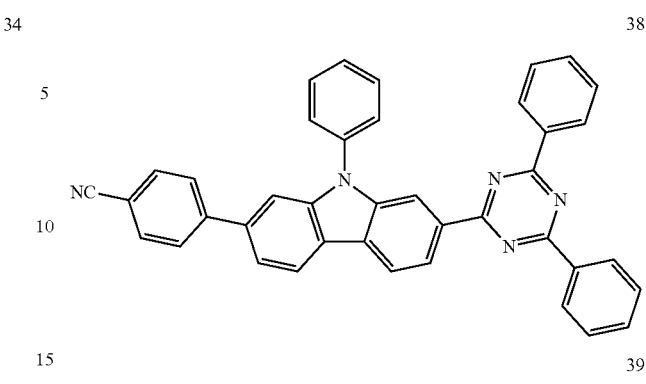
39
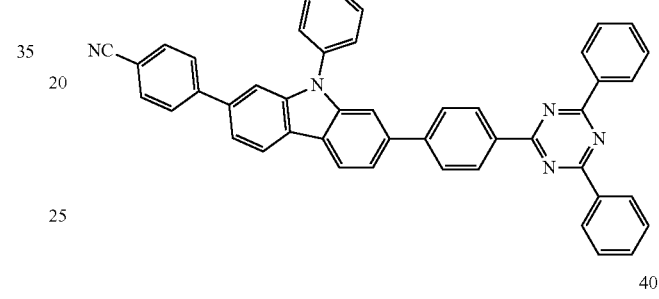
40
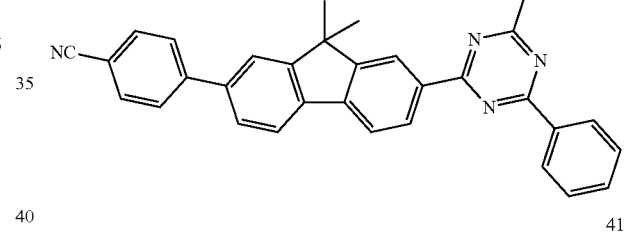
41
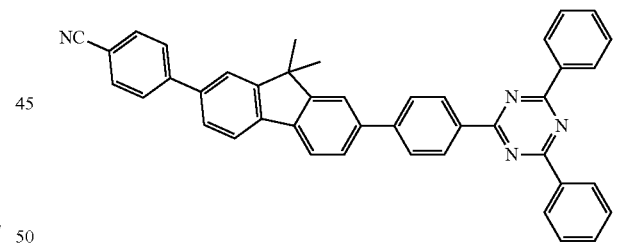
42
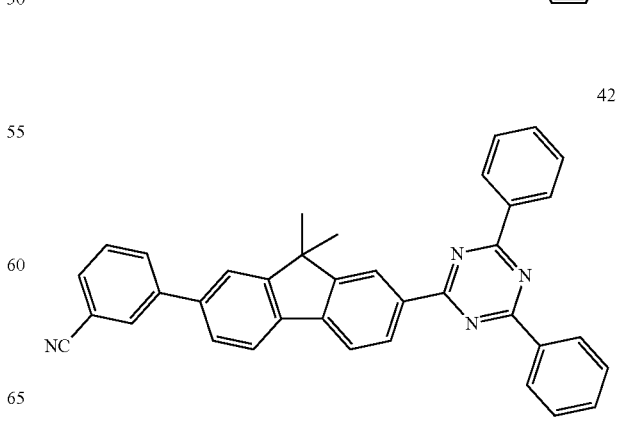

43
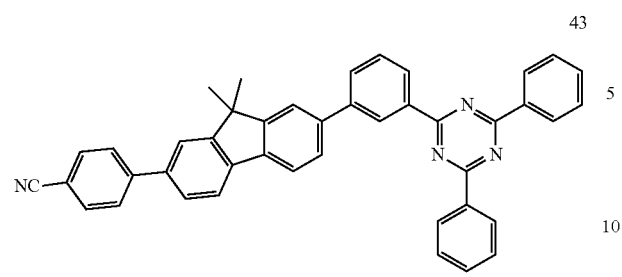
44
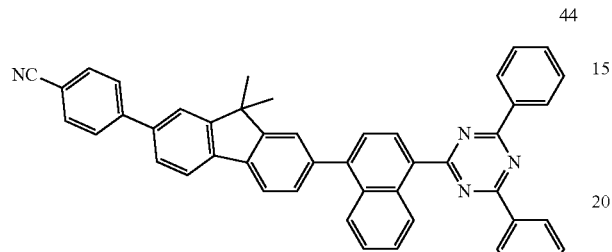
45
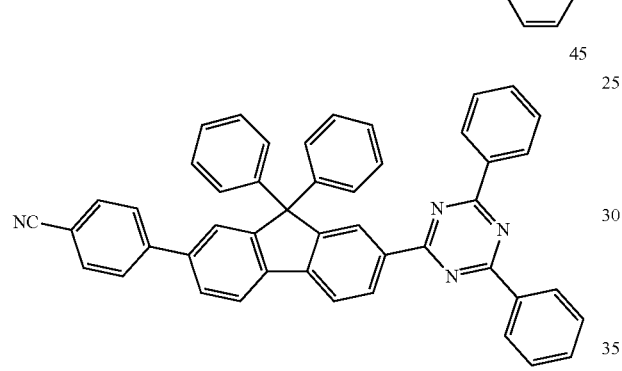
46
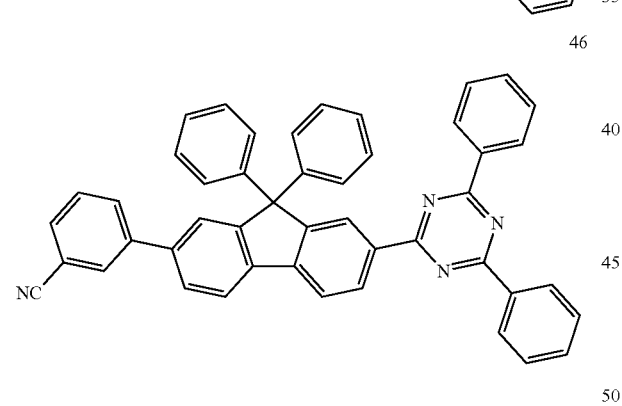
47
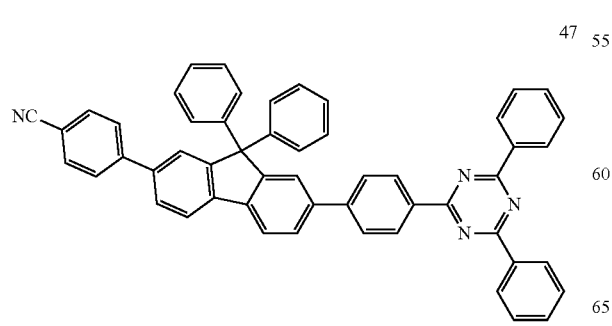
48
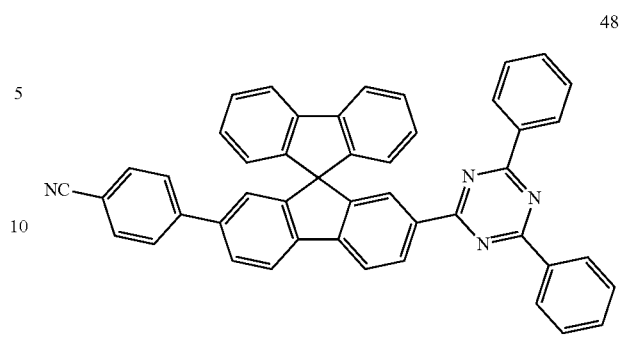
49
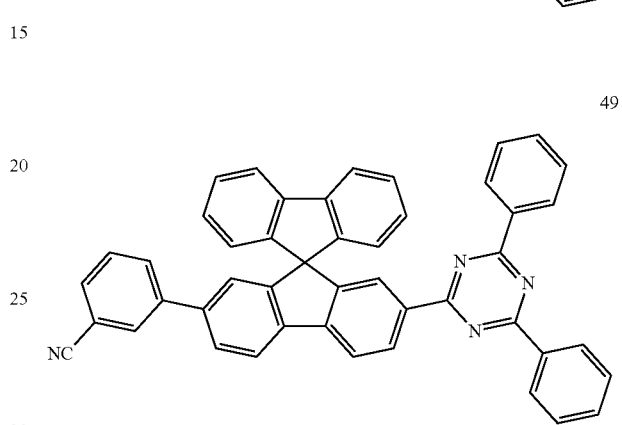
50
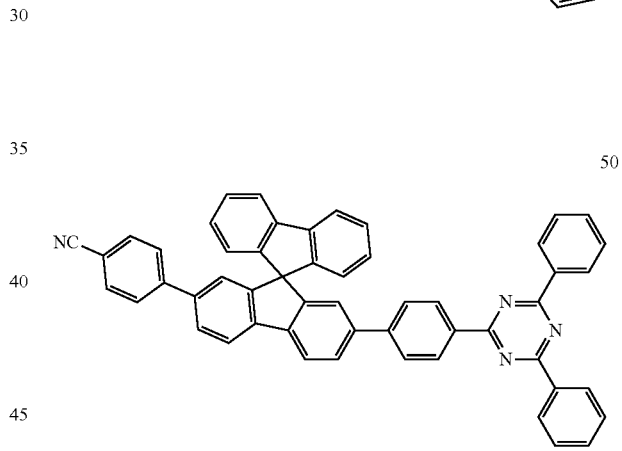
51
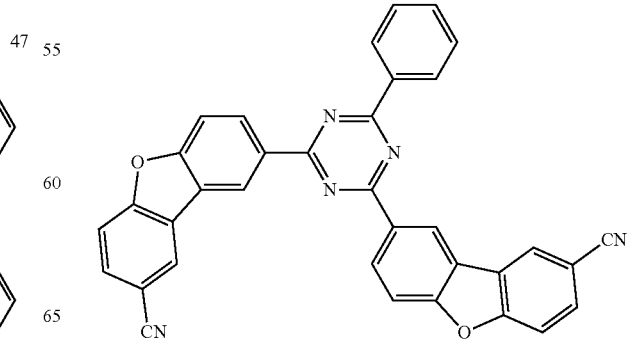

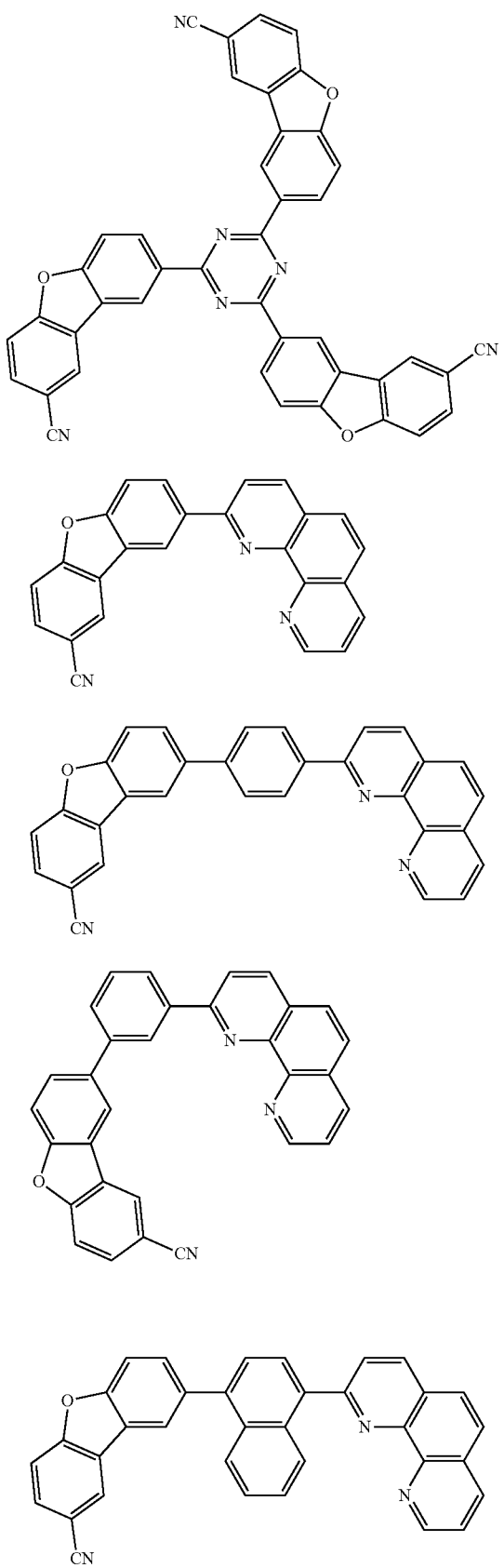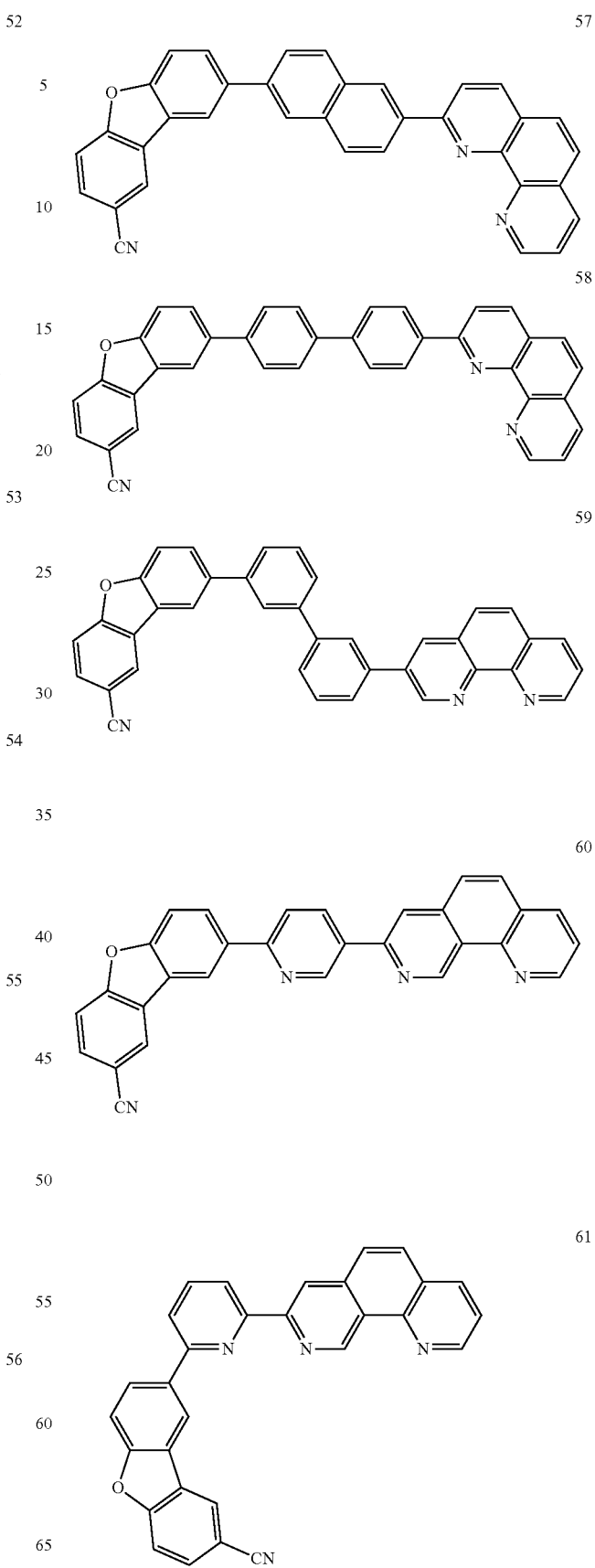

-continued
62 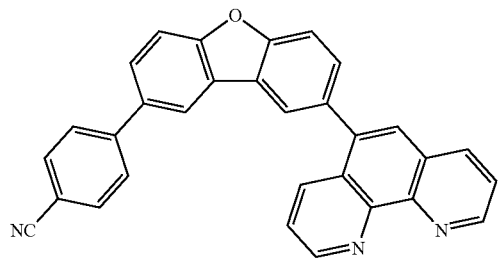
63 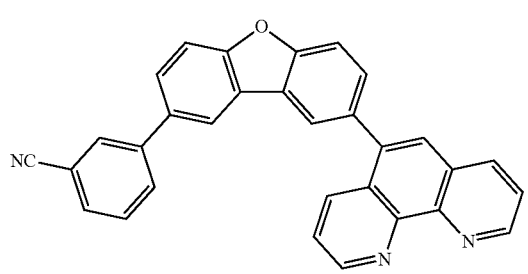
64 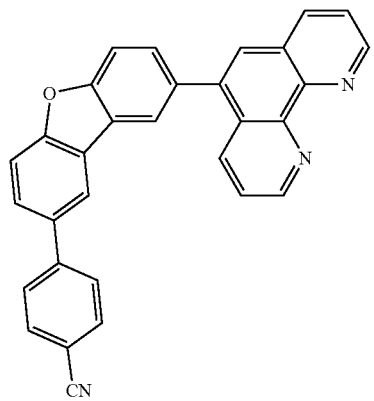
65 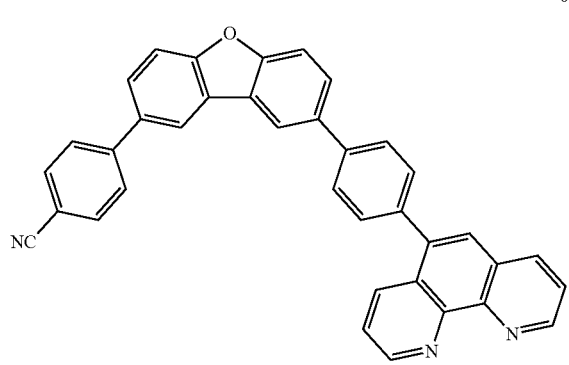
-continued
66 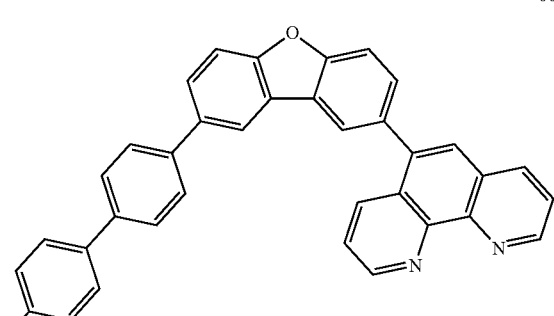
67 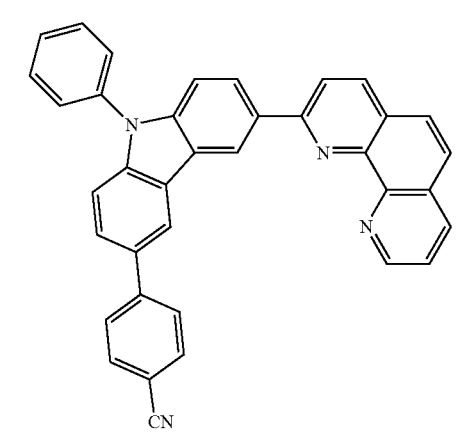
68 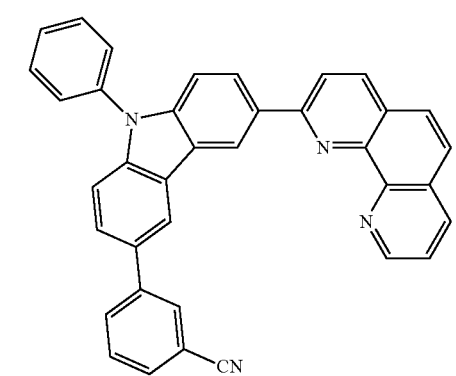
69 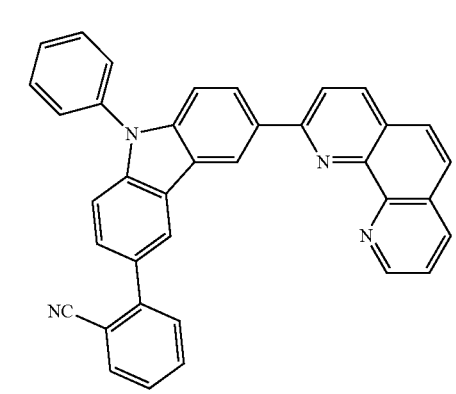

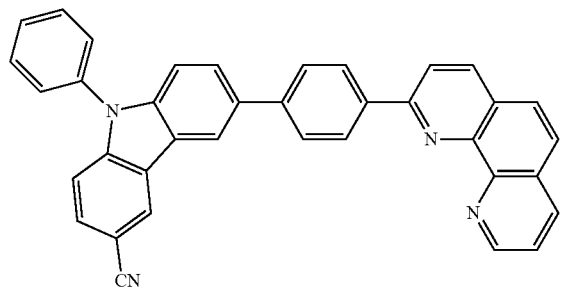
70
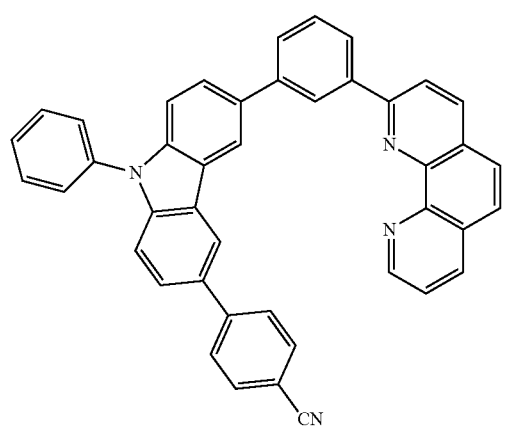
71
72
73
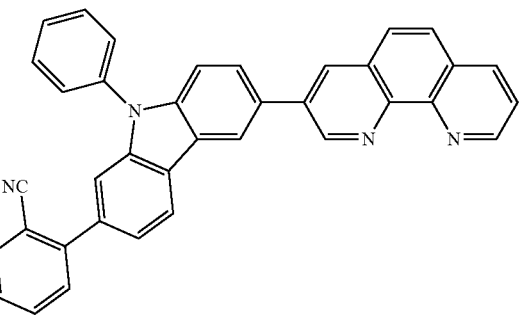
74
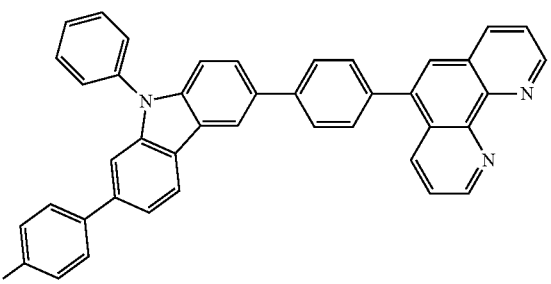
75
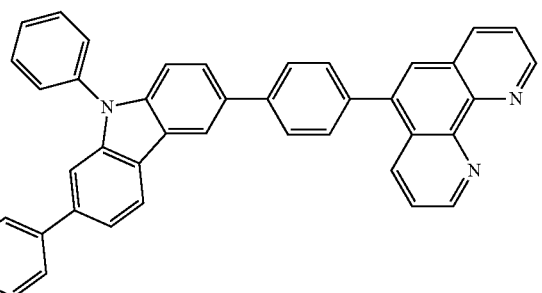
76
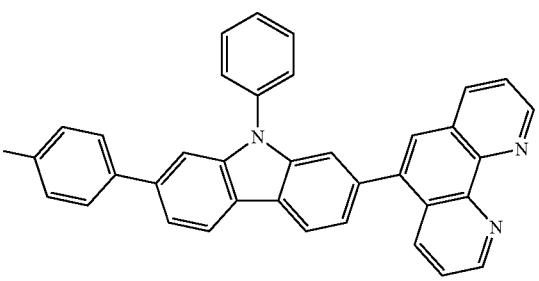
77
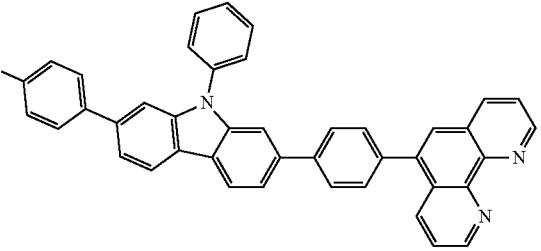
78

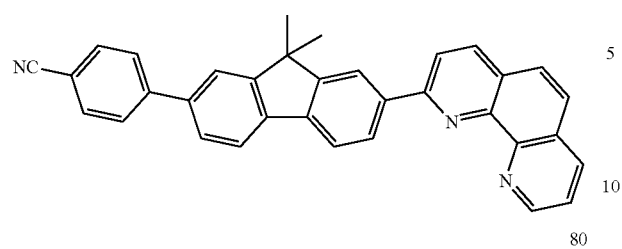
79
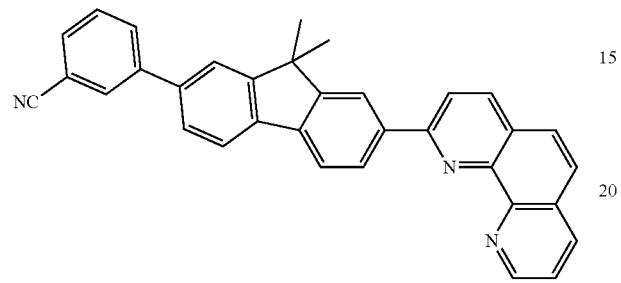
80
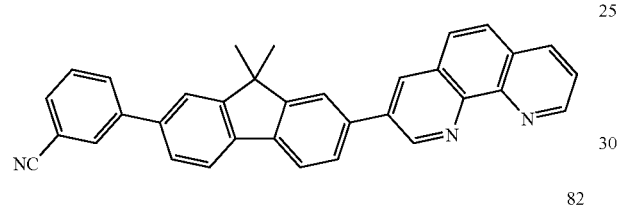
81
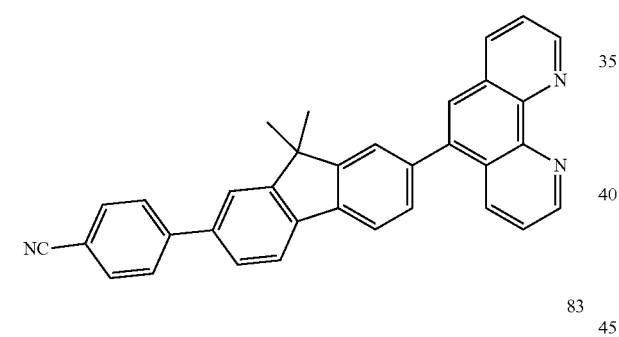
82
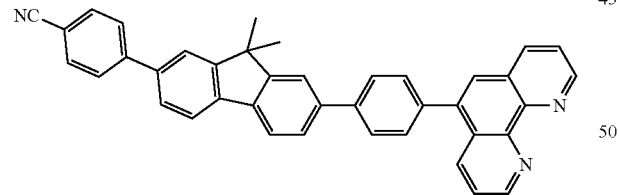
83
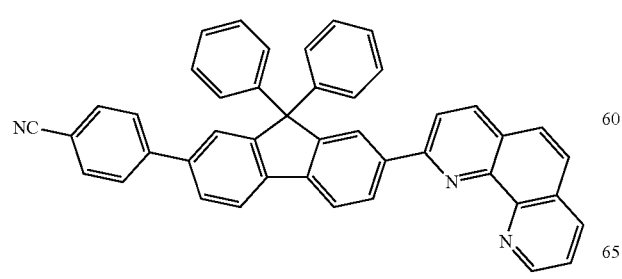
84
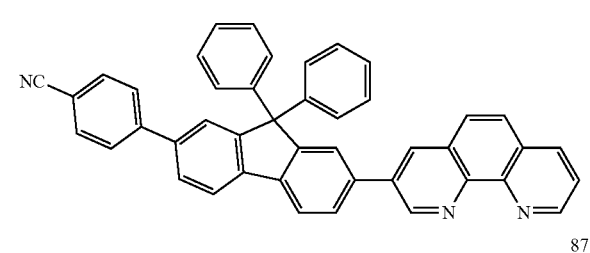
85
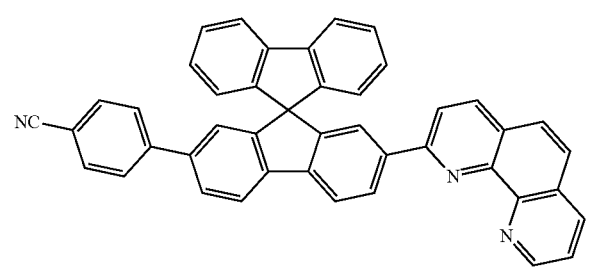
86
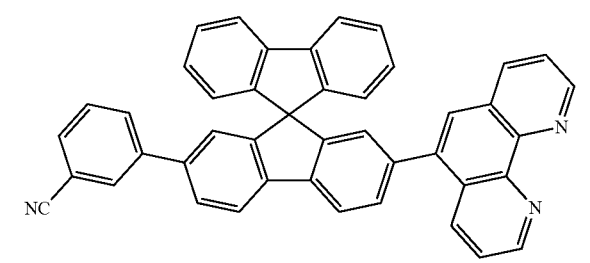
87
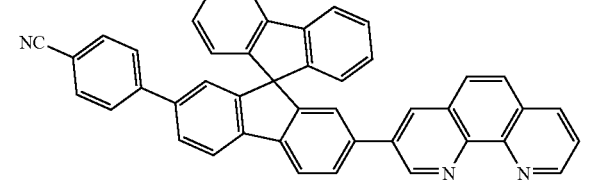
88
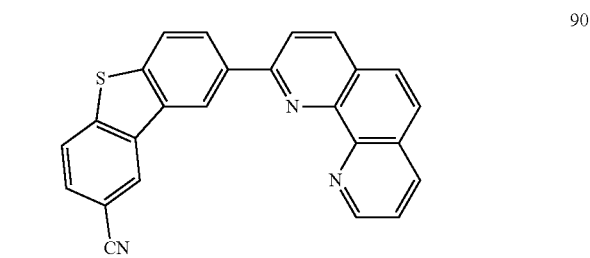
89
90

-continued

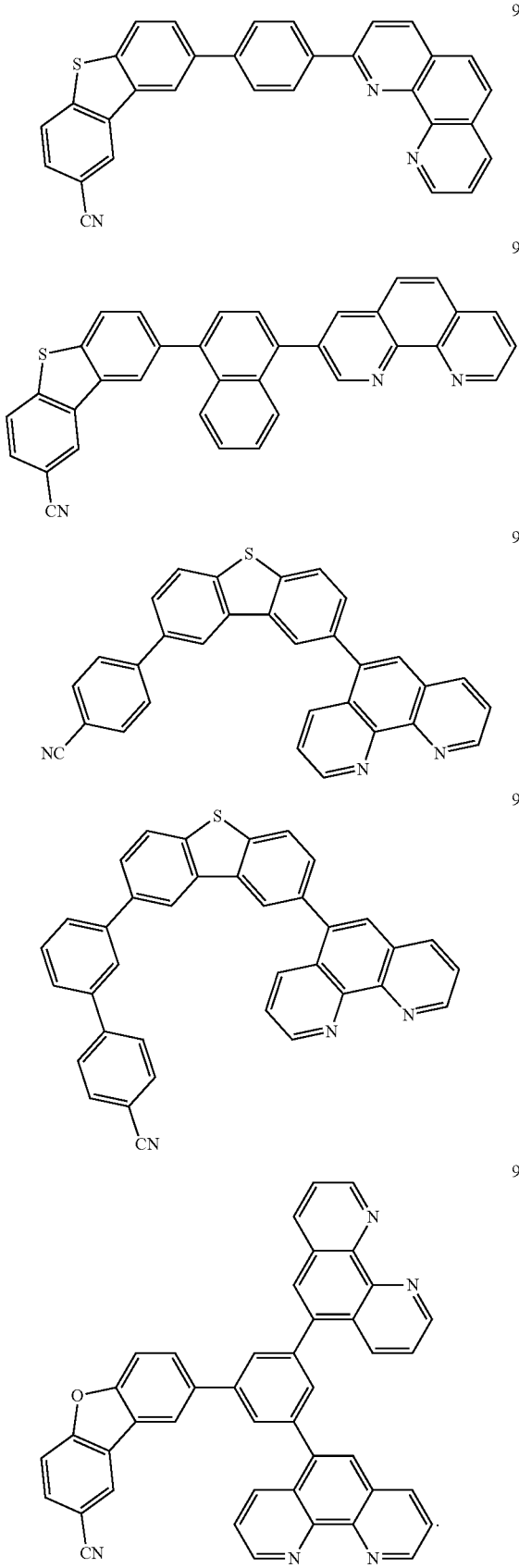

The heterocyclic compound may include a structure of Formula 1. In particular, the inclusion of a nitrogen-containing ring, such as a triazine or a phenanthroline, and a condensed polycyclic group in which a cyano group or a cyano group-containing cyclic group is substituted, may lead to improvement of electron transport capability. In this regard, an organic light-emitting device including, as an electron transport material, the heterocyclic compound may accordingly obtain low driving voltage, high efficiency, and long lifespan characteristics.

In the heterocyclic compound, a condensed polycyclic group may be substituted with a cyano group or a cyano group-containing cyclic group, thereby obtaining improved electron transport capability due to improved dipole moment.

In addition, the heterocyclic compound may include, as a substituent of the condensed polycyclic group, a cyano group or a cyano group-containing cyclic group instead of a fluoro group, thereby further improving electron transport capability and increasing effects in terms of mobility.

A synthesis method for the heterocyclic compound represented by Formula 1 would be readily apparent to those of ordinary skill in the art by referring to the following examples.

At least one of the heterocyclic compound of Formula 1 may be used between a pair of electrodes of an organic light-emitting device. For example, the heterocyclic compound may be included in at least one layer selected from a hole transport region, an electron transport region, and an emission layer. In one or more embodiments, the heterocyclic compound of Formula 1 may be used as a material for a capping layer located outside a pair of electrodes of an organic light-emitting device.

Accordingly, provided is an organic light-emitting device including: a first electrode; a second electrode facing the first electrode; and an organic layer between the first electrode and the second electrode, the organic layer including an emission layer, wherein the organic layer includes at least one of the heterocyclic compound.

The expression "an organic layer includes at least one heterocyclic compound," as used herein, may include a case in which "an organic layer includes identical compounds represented by Formula 1" and a case in which "an organic layer includes two or more different heterocyclic compounds represented by Formula 1."

For example, the first electrode is an anode and the second electrode is a cathode, and the organic layer includes a hole transport region between the first electrode and the emission layer and an electron transport region between the emission layer and the second electrode, and the hole transport region includes a hole injection layer, a hole transport layer, a buffer layer, an electron blocking layer, or any combination thereof, and the electron transport region includes a buffer layer, a hole blocking layer, an electron transport layer, an electron injection layer, or any combination thereof.

In one embodiment, the electron transport region may include at least one of the heterocyclic compounds.

For example, the electron transport region may include an electron transport layer and an electron injection layer, and the electron transport layer may include at least one of the heterocyclic compounds.

For example, the hole transport region may include a p-dopant, the p-dopant may have a lowest unoccupied molecular orbital (LUMO) level of about −3.5 eV or less.

For example, the p-dopant may include a cyano group-containing compound.

A host in the emission layer may include at least one selected from an anthracene-based compound, a pyrene-based compound, an arylamine-based compound, and a styryl-based compound, but embodiments of the present disclosure are not limited thereto.

In the organic light-emitting device, the emission layer may be a first emission layer emitting first color light,
the organic light-emitting device may further include i) at least one second color light emission layer-second emission layer or ii) at least one second color light emission layer-second emission layer and at least one third color light emission layer-third emission layer, between the first electrode and the second electrode,
a maximum emission wavelength of the first color light, a maximum emission wavelength of the second color light, and a maximum emission wavelength of the third color light are identical (e.g., substantially identical) to or different from each other, and
the first color light and the second color light are emitted in the form of mixed light, or the first color light, the second color light, and the third color light are emitted in the form of mixed light.

The organic light-emitting device may further include at least one selected from a first capping layer disposed in a pathway along which light generated in an emission layer proceeds toward the outside through the first electrode and a second capping layer disposed in a pathway along which light generated in an emission layer proceeds toward the outside through the second electrode, and the at least one selected from the first capping layer and the second capping layer may include at least one heterocyclic compound represented by Formula 1.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the heterocyclic compound.

Another aspect of an embodiment of the present disclosure provides an electronic apparatus including a thin film transistor and the organic light-emitting device,
wherein the thin-film transistor may include a source electrode, a drain electrode, an activation layer, and a gate electrode, and
the first electrode of the organic light-emitting device may be electrically connected with at least one of the source electrode and the drain electrode of the thin film transistor.

The term "organic layer," as used herein, refers to a single layer and/or a plurality of layers disposed between the first electrode and the second electrode of the organic light-emitting device. A material included in the "organic layer" is not limited to an organic material. For example, the organic layer may include an inorganic material in addition to an organic material.

Description of FIG. 1

Figures 1, 2:
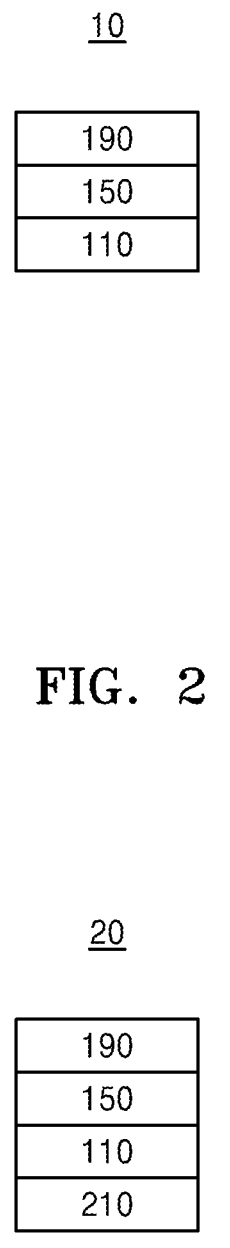

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

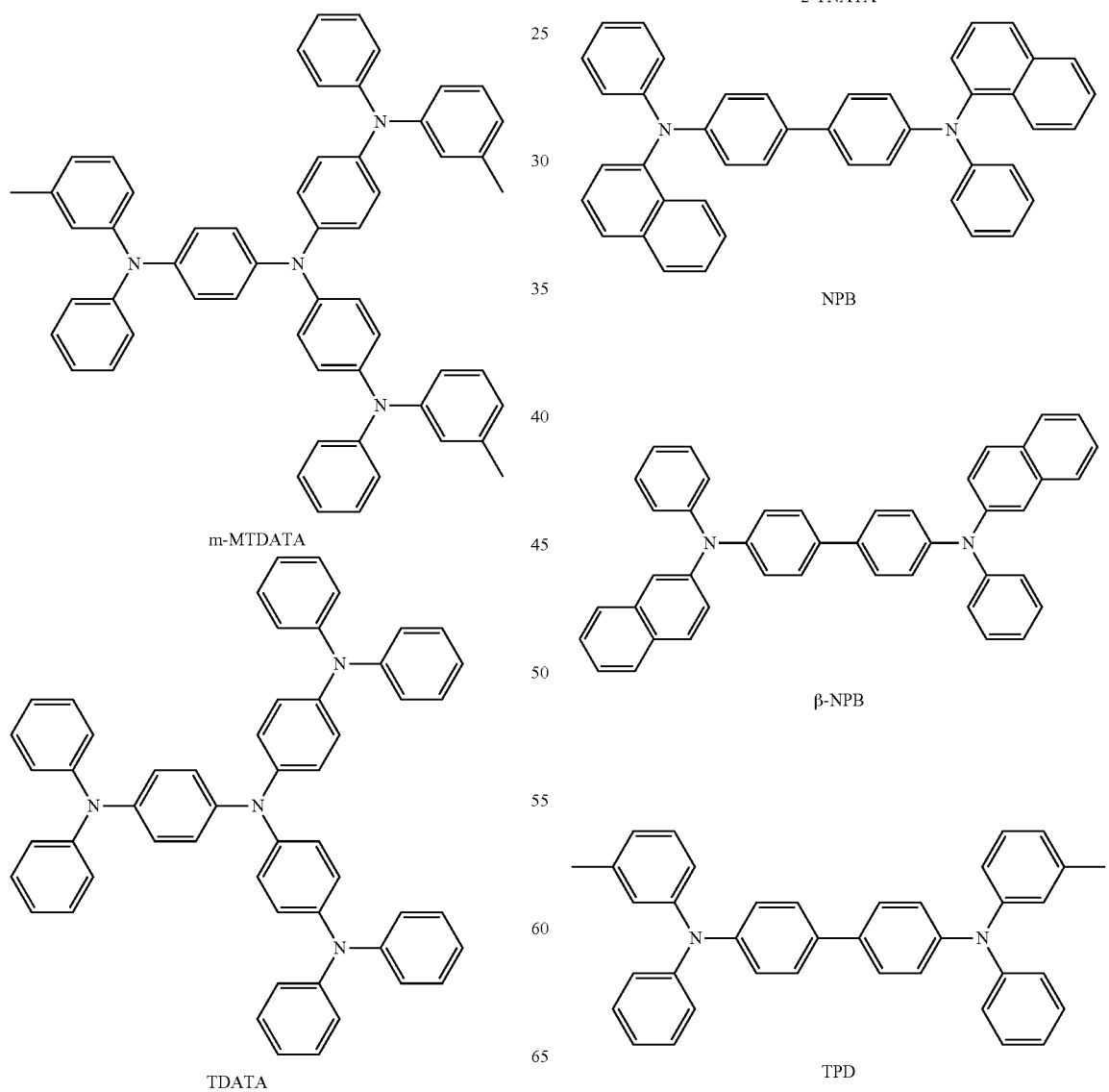

45
-continued

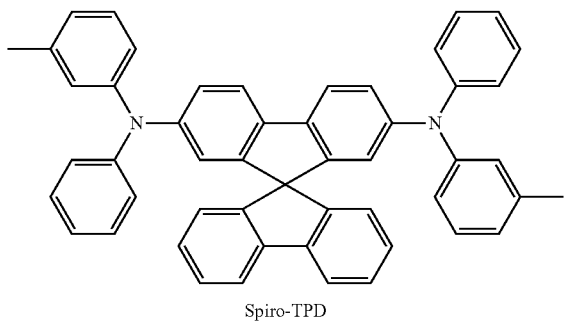
Spiro-TPD

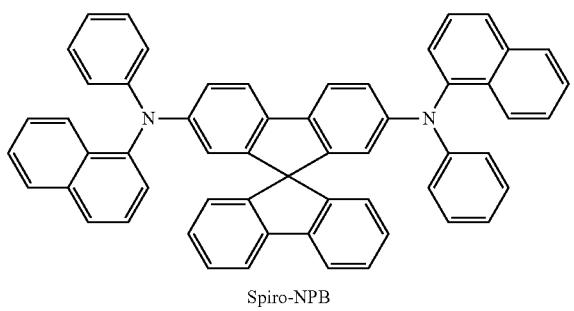
Spiro-NPB

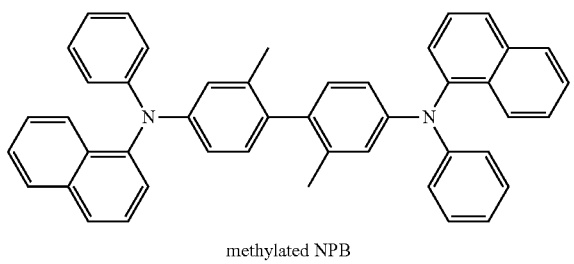
methylated NPB

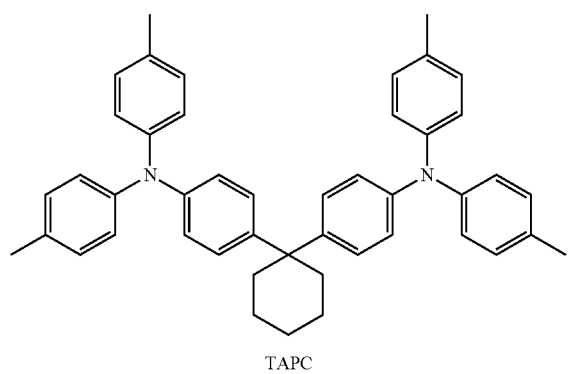
TAPC

46
-continued

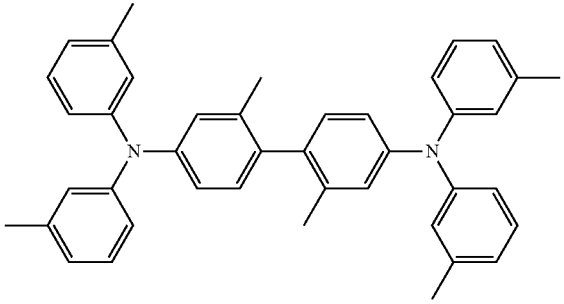
HMTPD

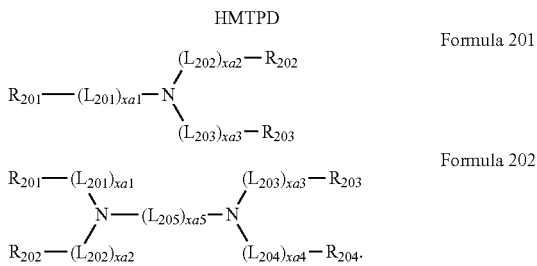

Formula 201
Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked each other via each other a single bond, a dimethyl-methylene group, or a diphenyl-methylene group, and $R_{203}$ and $R_{204}$ may optionally be linked each other via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $-Si(Q_{31})(Q_{32})(Q_{33})$, and $-N(Q_{31})(Q_{32})$, and $Q_{31}$ to $Q_{33}$ may respectively be the same as defined above.

In one or more embodiments, in Formula 201, at least one selected from $R_{201}$ to $R_{203}$:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group;

but embodiments of the present disclosure are not limited thereto.

In one or more embodiments, in Formula 202, i) $R_{201}$ and $R_{202}$ may be linked each other via a single bond, and/or ii) $R_{203}$ and $R_{204}$ may be linked each other via a single bond.

In one or more embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

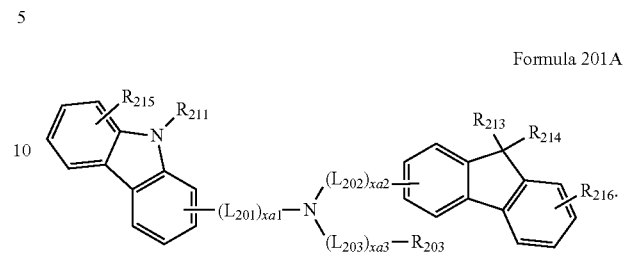

Formula 201A

In one embodiment, the compound represented by Formula 201 may be represented by Formula 201A(1) below, but embodiments of the present disclosure are not limited thereto:

Formula 201A(1)

In one embodiment, the compound represented by Formula 201 may be represented by Formula 201A-1 below, but embodiments of the present disclosure are not limited thereto:

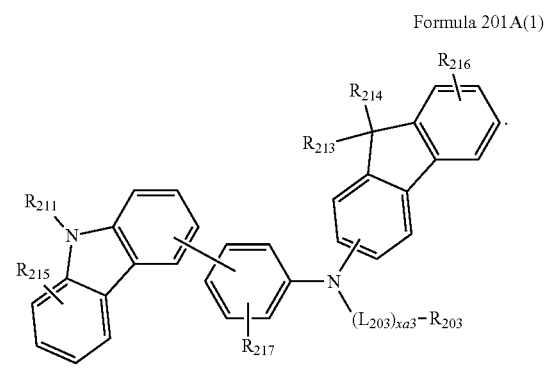

Formula 201A-1

In one embodiment, the compound represented by Formula 202 may be represented by Formula 202A:

Formula 202A

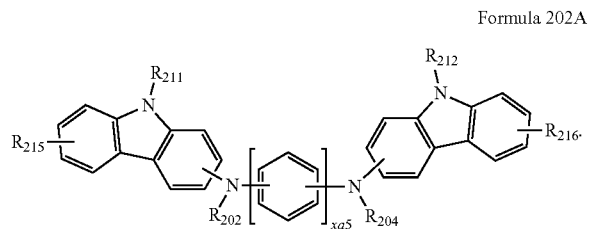

In one embodiment, the compound represented by Formula 202 may be represented by Formula 202A-1:

Formula 202A-1

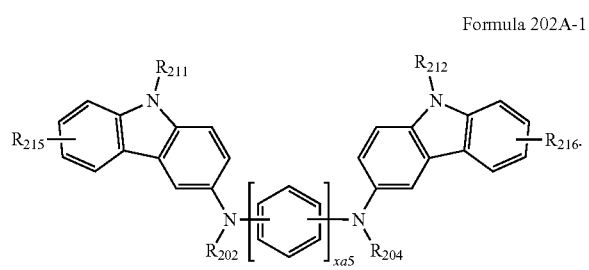

In Formulae 201A, 201A(1), 201A-1, 202A, and 202A-1, $L_{201}$ to $L_{203}$, xa1 to xa3, xa5, and $R_{202}$ to $R_{204}$ may respectively be the same as defined above, $R_{211}$ and $R_{212}$ may respectively be the same as defined in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

HT1

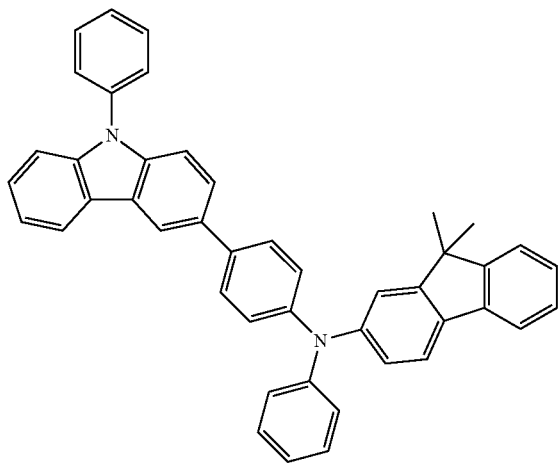

HT2

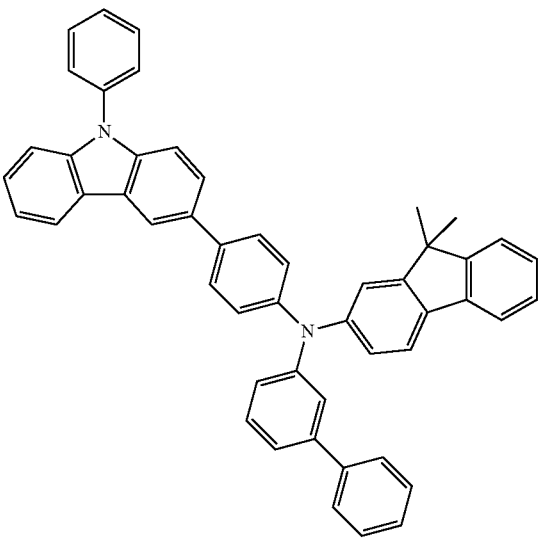

HT3
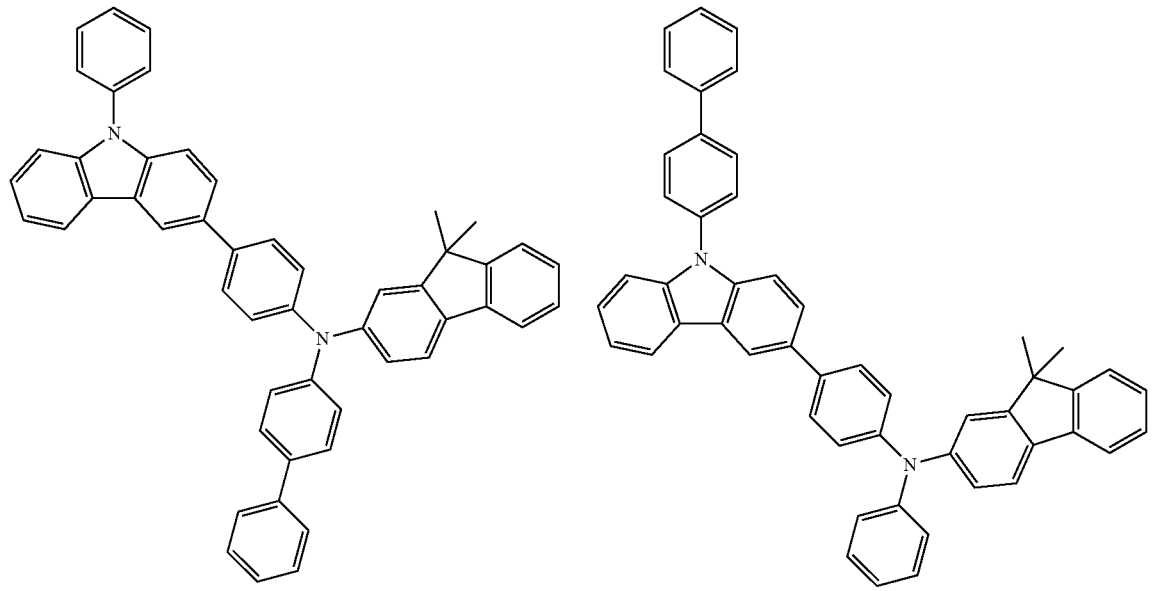
HT4
HT5
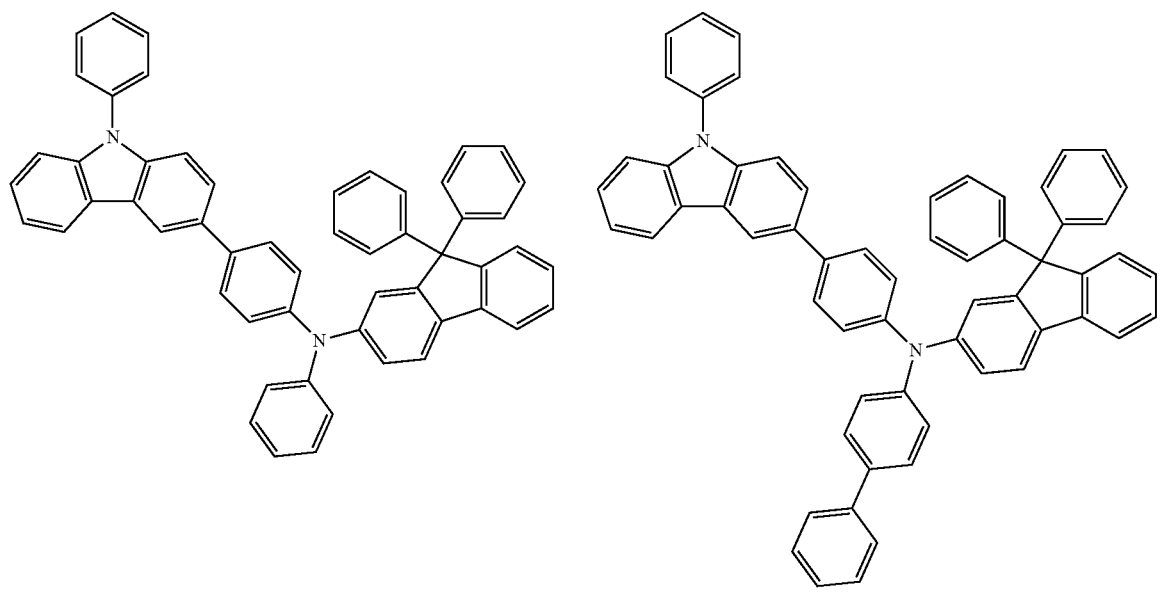
HT6

-continued
HT7
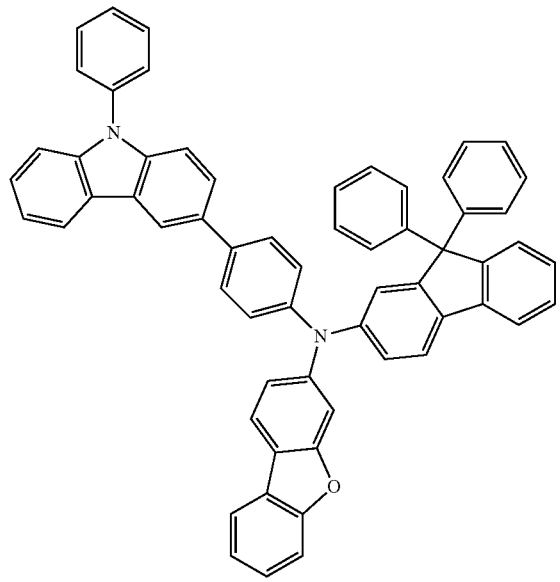
HT8
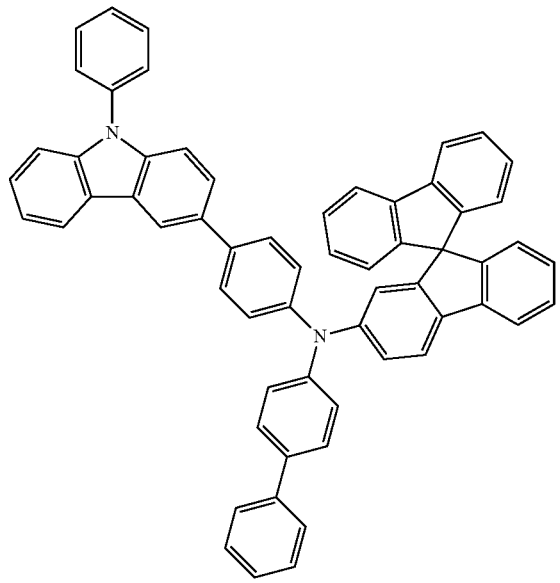
HT9
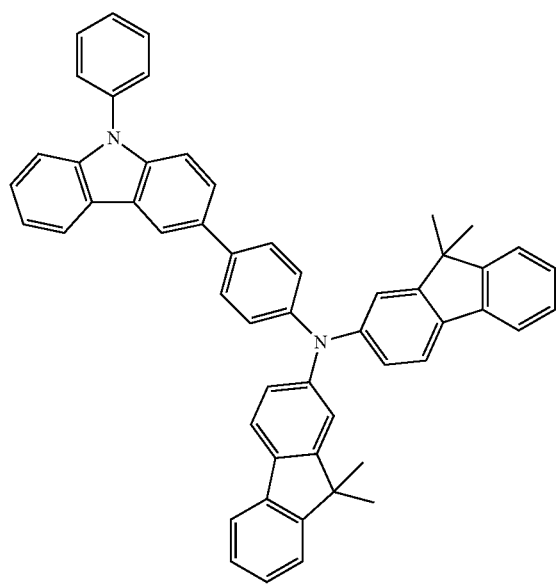
HT10
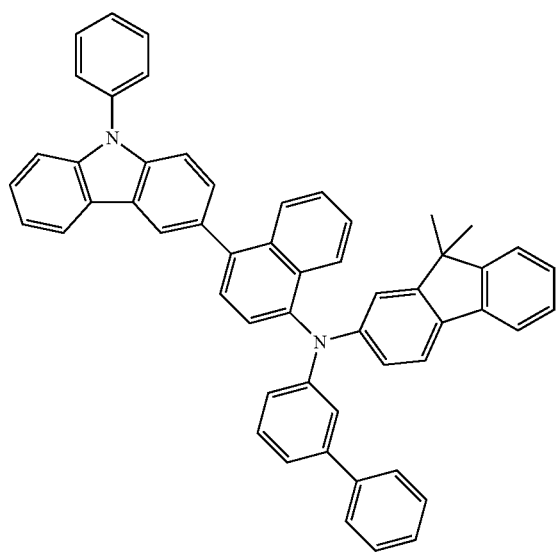

-continued
HT11
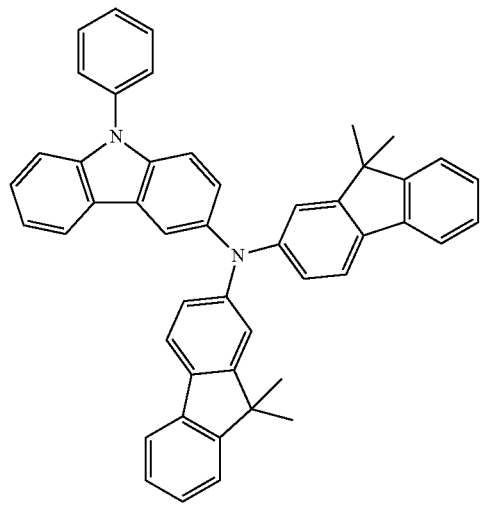
HT12
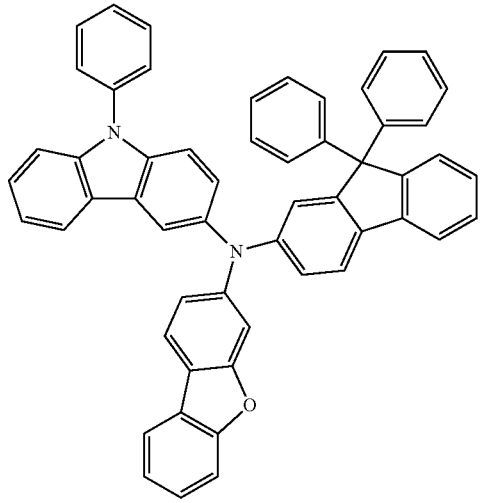
HT13
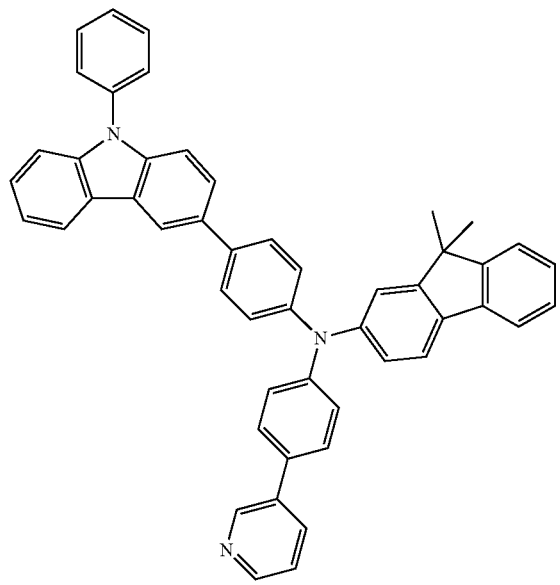
HT14
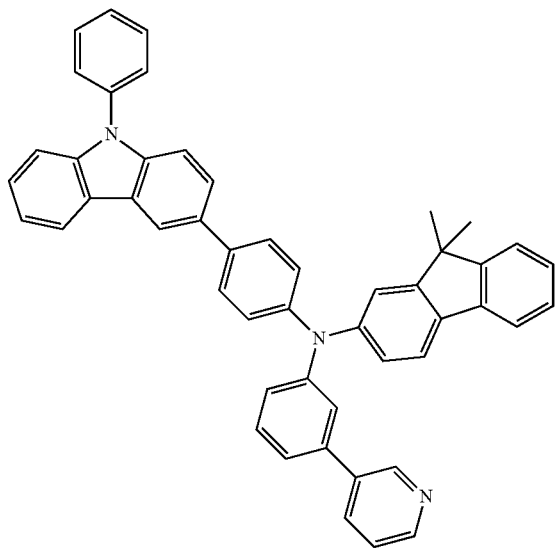
HT15
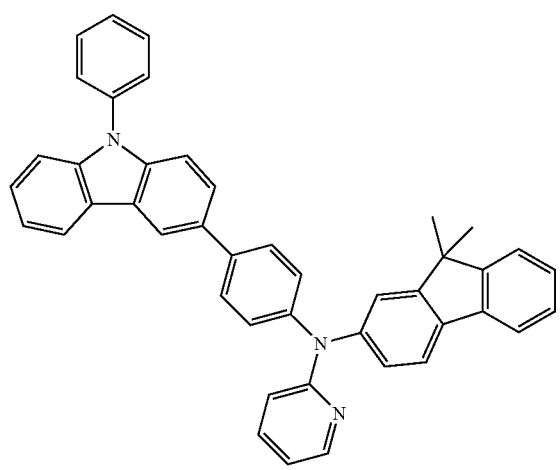
HT16
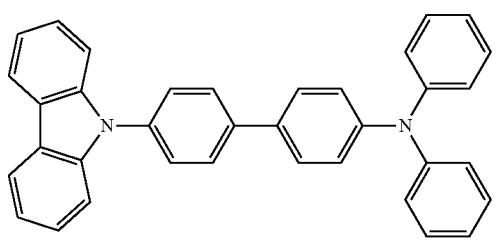

-continued
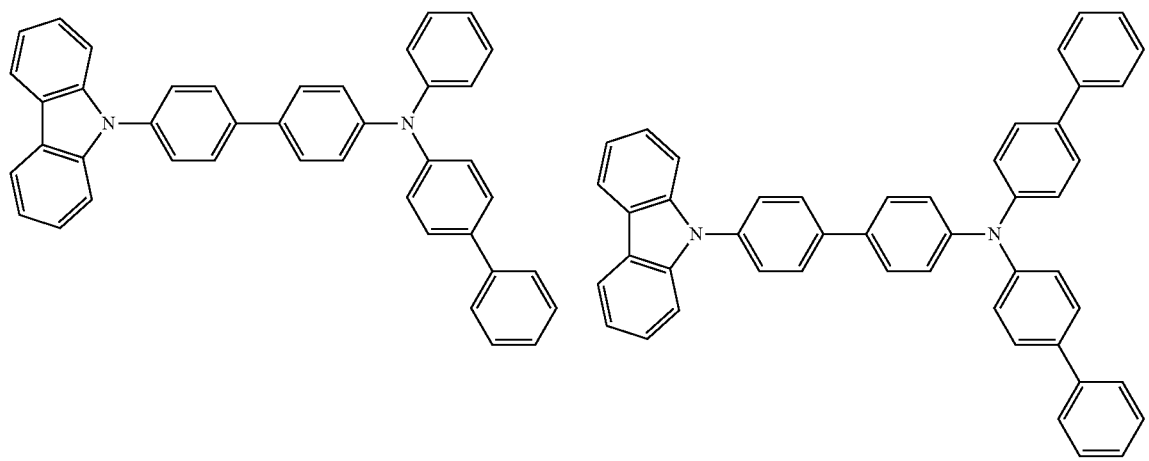
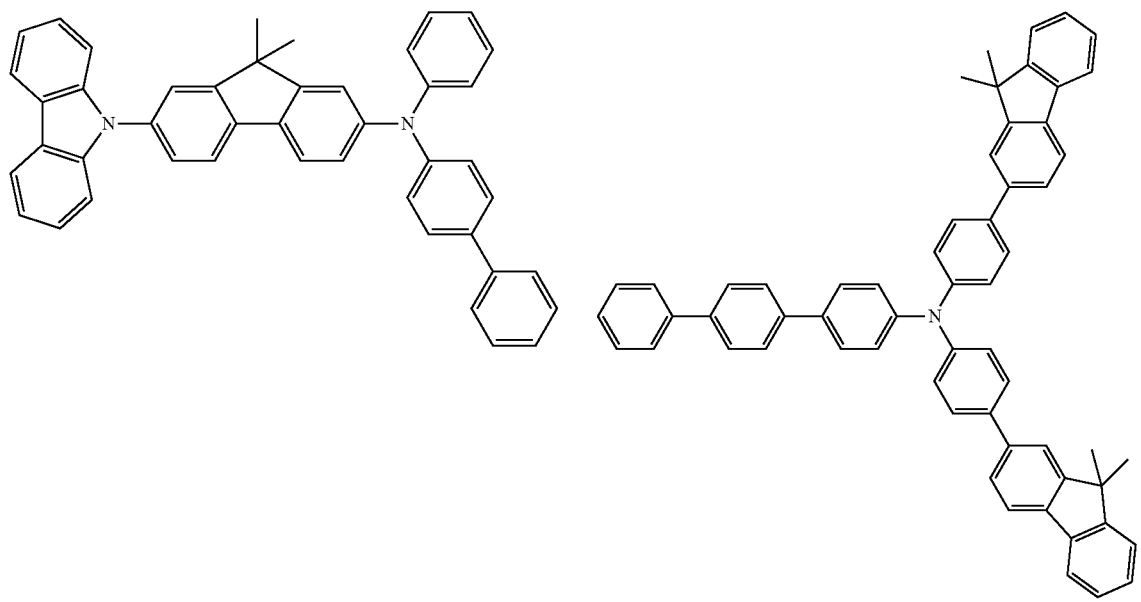

-continued
HT21
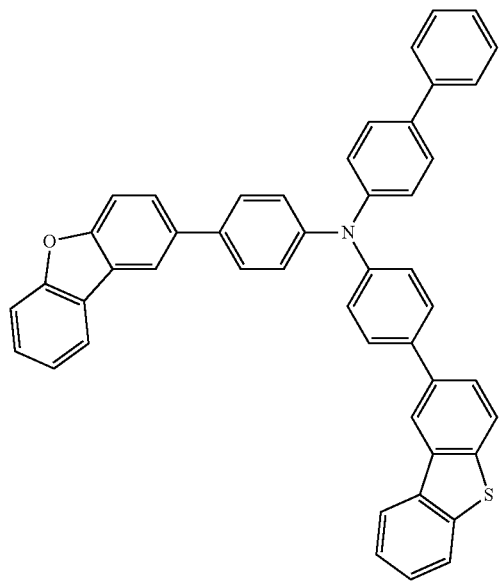
HT22
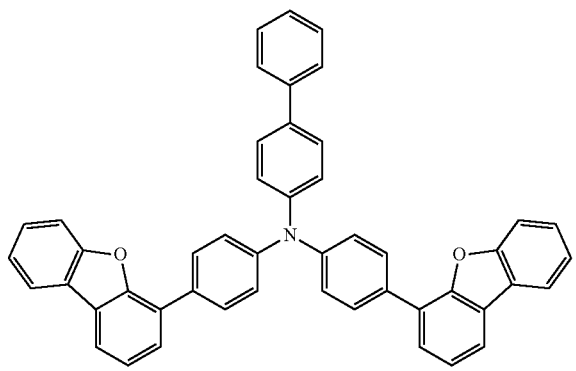
HT23
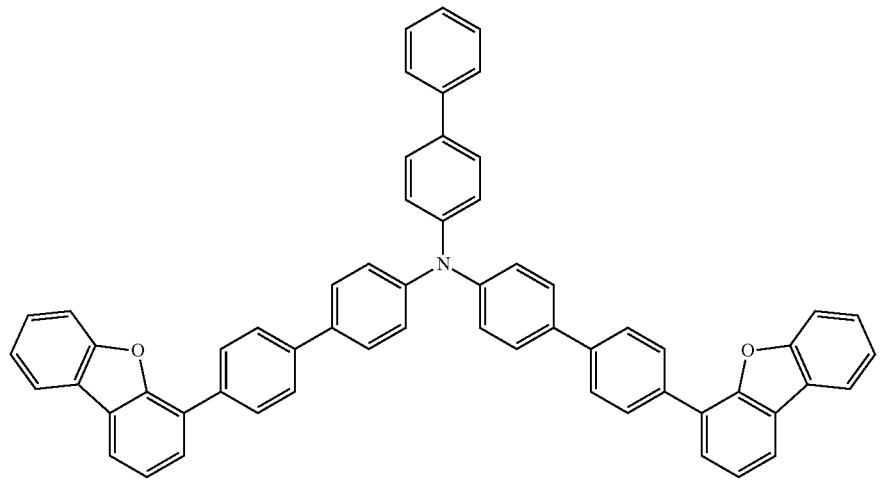
HT24
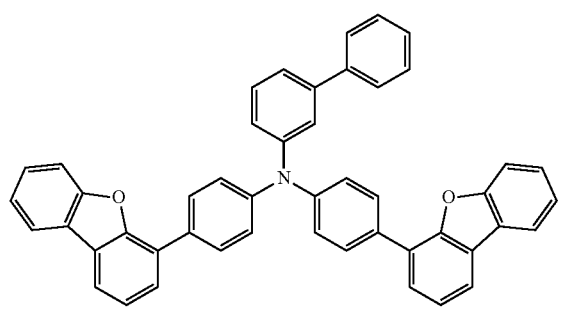
HT25
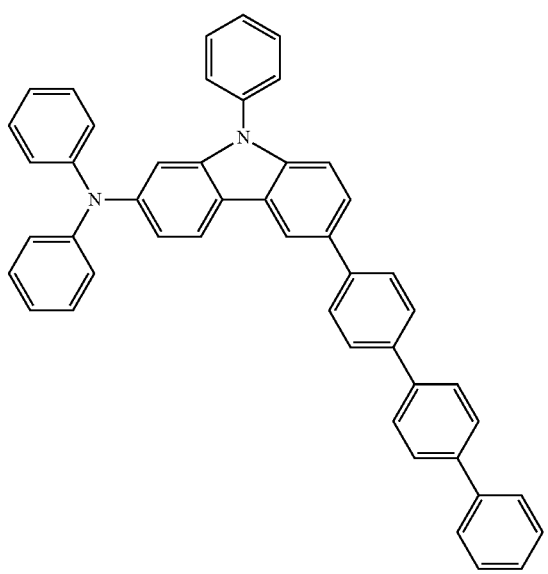

-continued
HT26
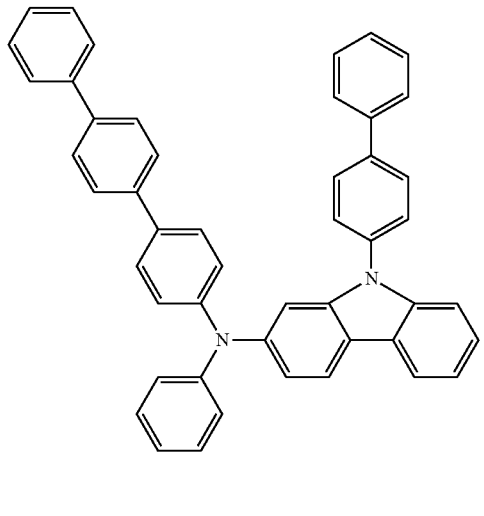
HT27
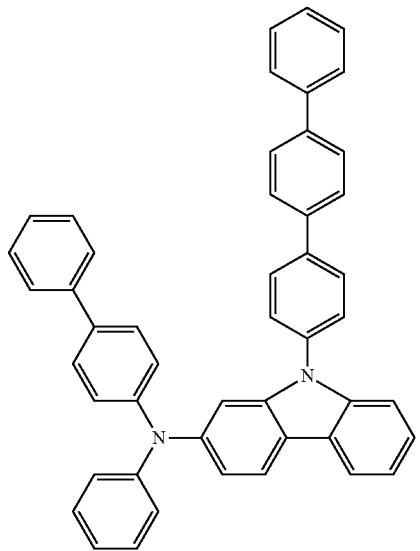
HT28
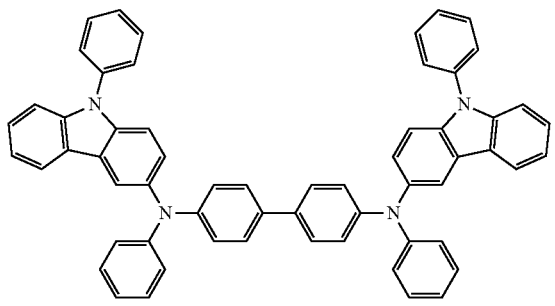
HT29
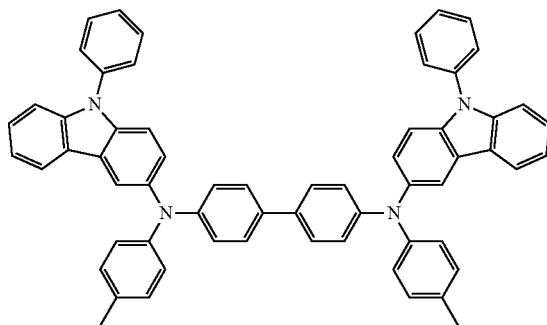
HT30
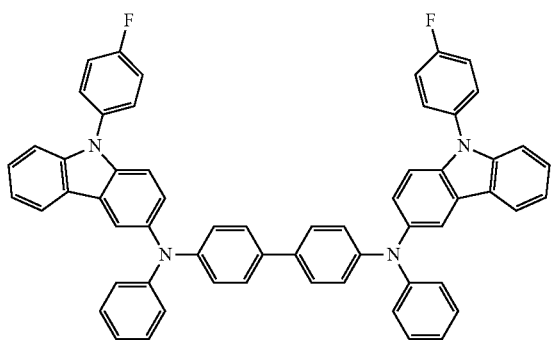
HT31
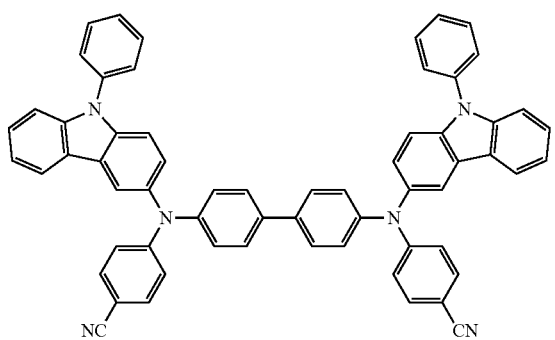

-continued
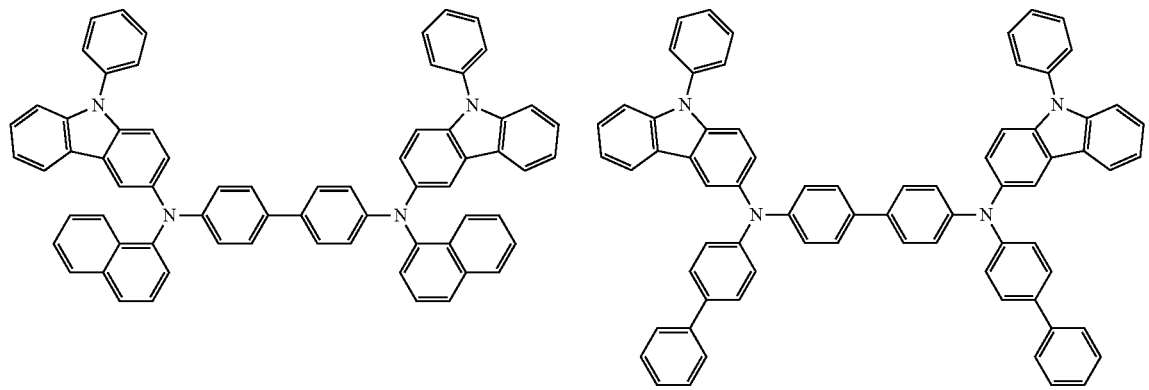
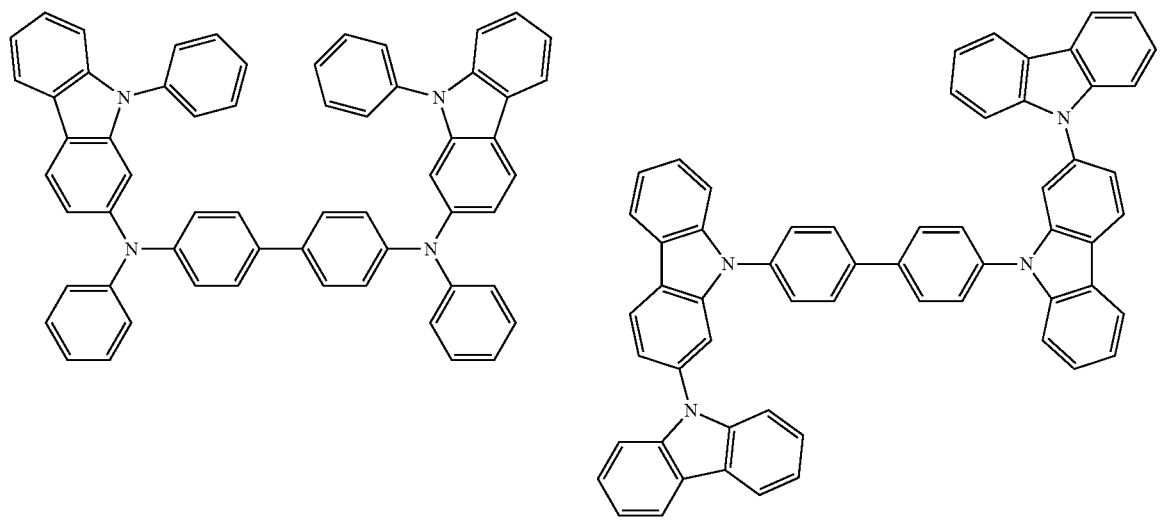
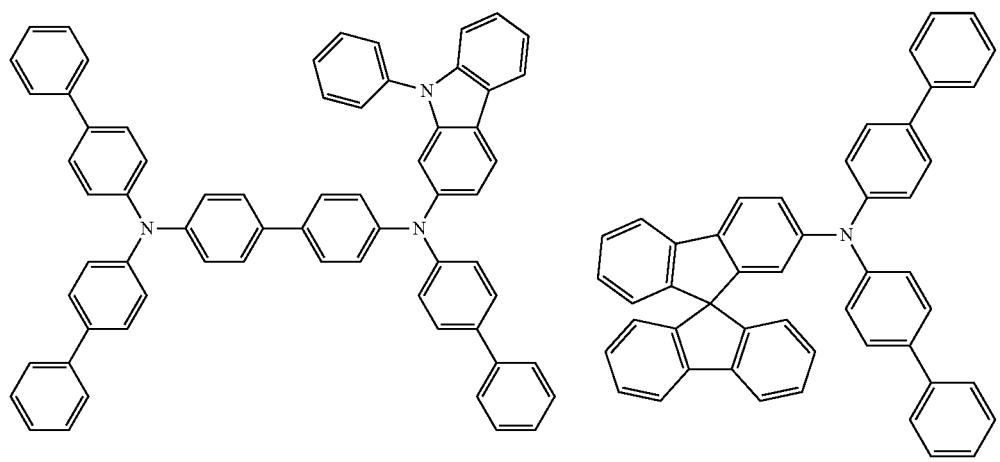

-continued

HT38

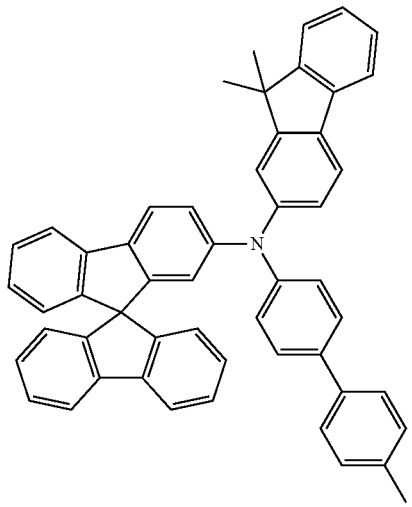

HT39

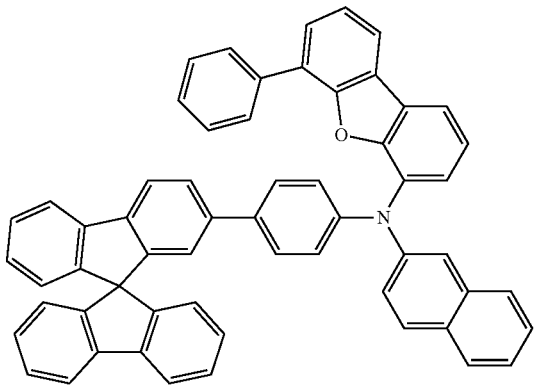

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a LUMO level of about −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:
 a quinone derivative, such as tetracyanoquinodimethane (TCNQ) or 2,3,5,6-tetrafluoro-7,7,8,8-tetracyanoquinodimethane (F4-TCNQ);
 a metal oxide, such as tungsten oxide or molybdenum oxide;

1,4,5,8,9,12-hexaazatriphenylene-hexacarbonitrile (HAT-CN); and
a compound represented by Formula 221,
but embodiments of the present disclosure are not limited thereto:

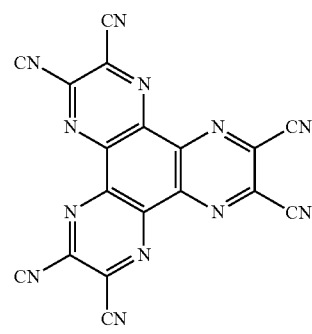

HAT-CN

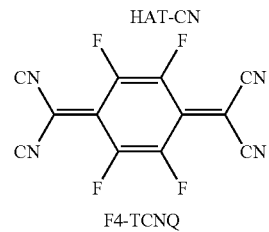

F4-TCNQ

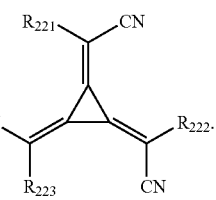

Formula 221

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer, an amount of the dopant may be in a range of about 0.01 parts to about 15 parts by weight based on 100 parts by weight of the host.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Host in Emission Layer

In one or more embodiments, the host may further include a compound represented by Formula 301:

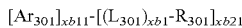

Formula 301

In Formula 301, $Ar_3O_1$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer of 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer of 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_3O_1$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 301, when xb11 is two or more, two or more of $Ar_{301}(s)$ may be linked each other via a single bond.

In one or more embodiments, the compound represented by Formula 301 may be represented by Formula 301-1 or 301-2:

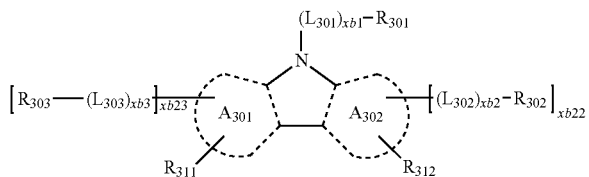

Formula 301-1

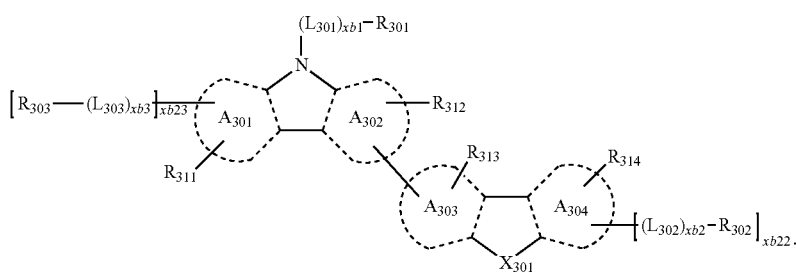

Formula 301-2

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may respectively be the same as defined above, $L_{302}$ to $L_{304}$ may respectively be the same as defined in connection with $L_{301}$, xb2 to xb4 may respectively be the same as defined in connection with xb1, and $R_{302}$ to $R_{304}$ may respectively be the same as defined in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ and $Q_{33}$ may respectively be the same as defined above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_{31}$ and Q$_{33}$ may respectively be the same as defined above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1

H2

H3

H4

-continued

H5

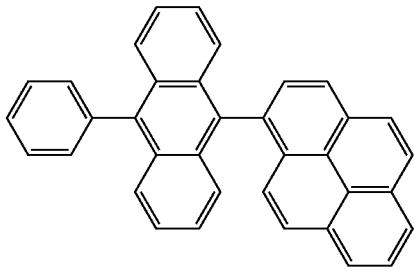

H6

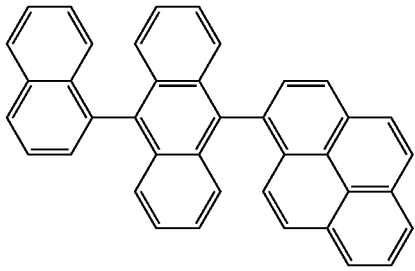

H7

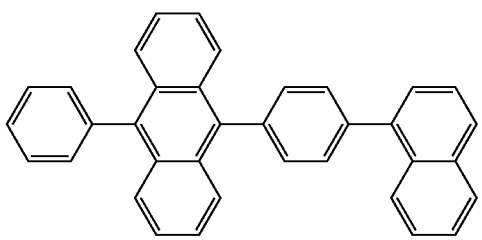

H8

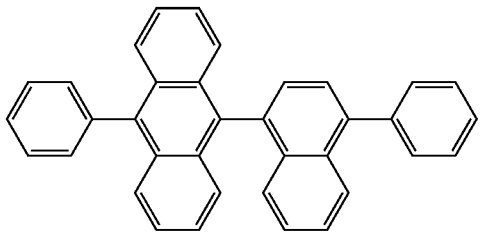

H9

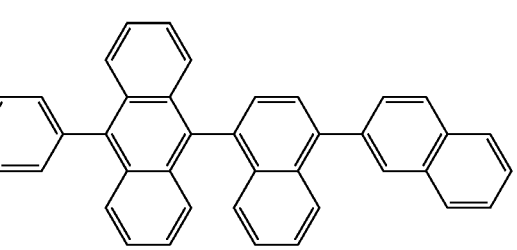

H10

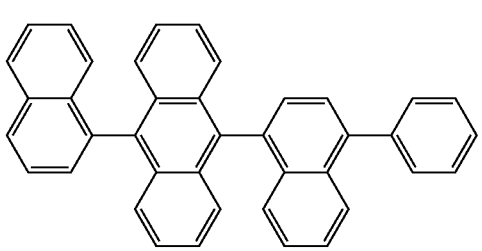

H11
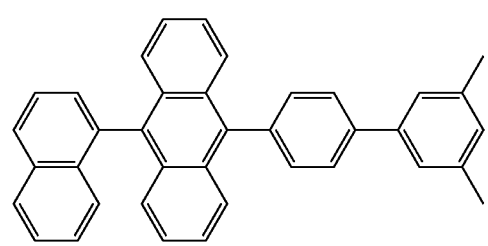
H12
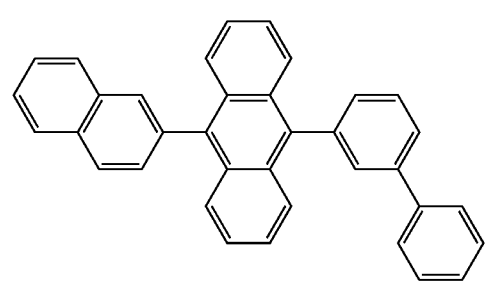
H13
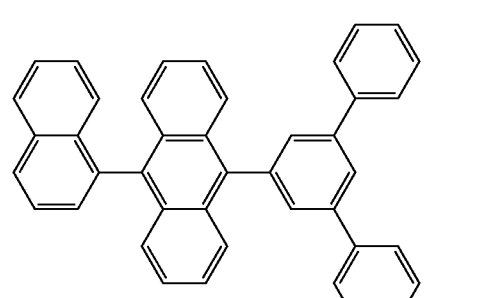
H14
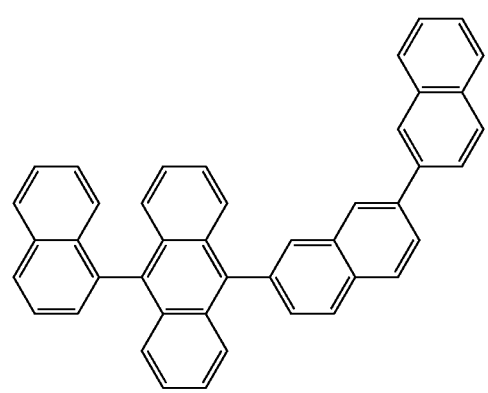
H15
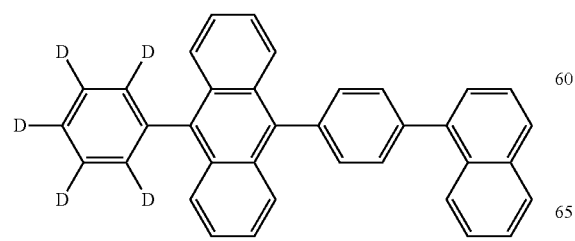
H16
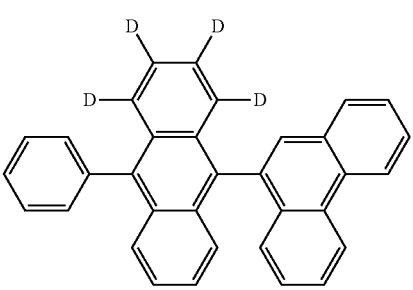
H17
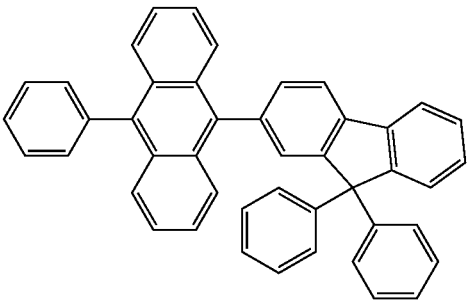
H18
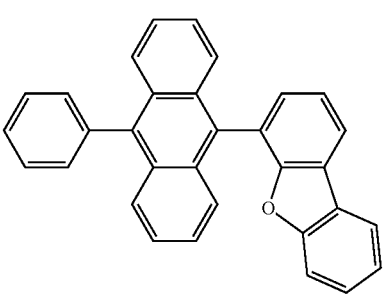
H19
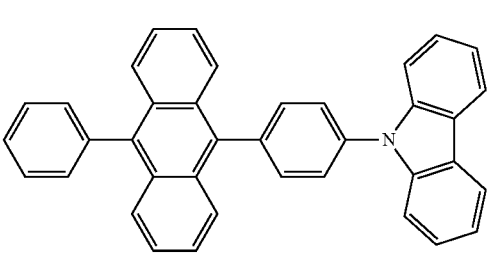
H20
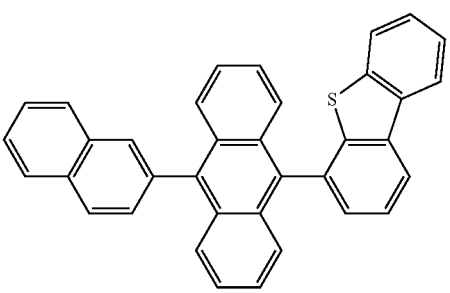

H21
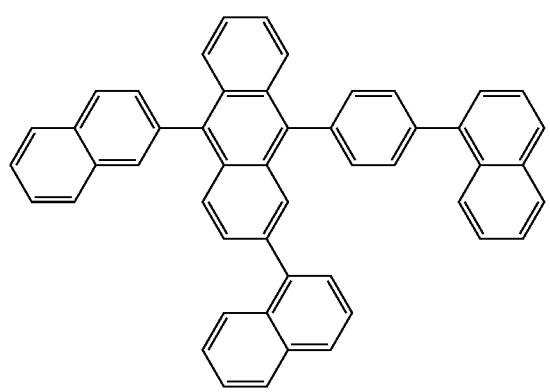
H22
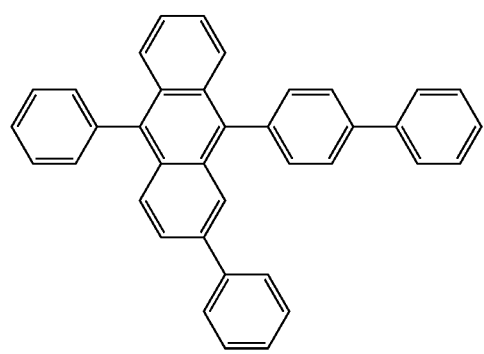
H23
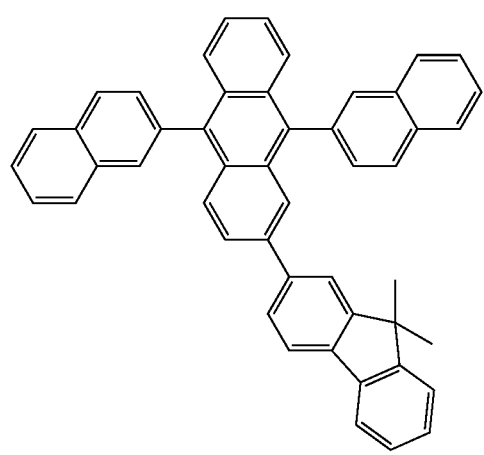
H24
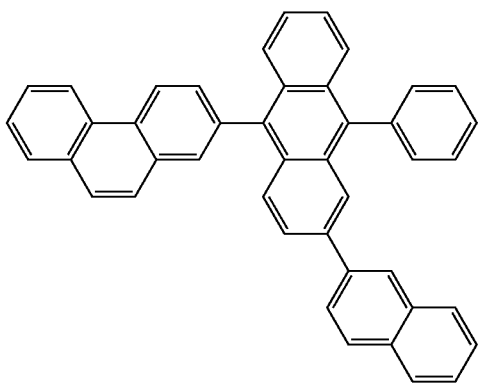
H25
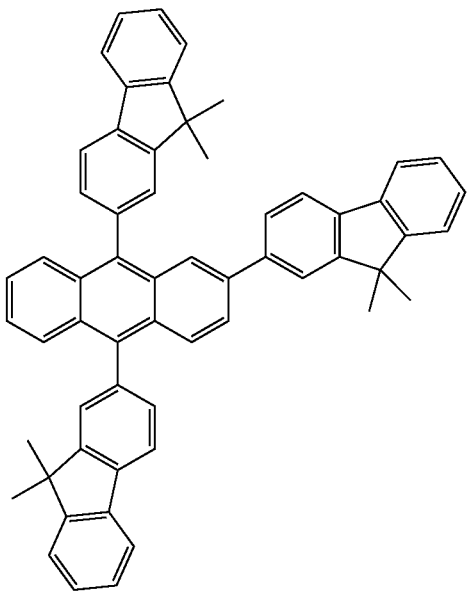
H26
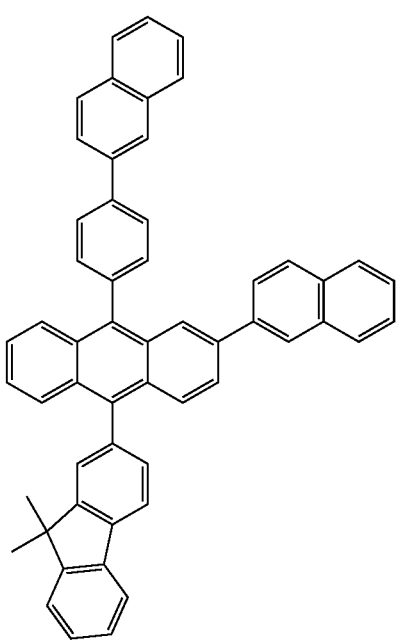

H27
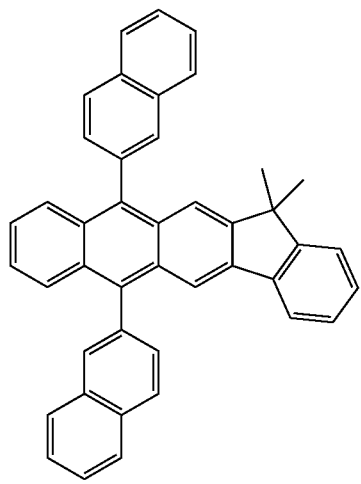
H28
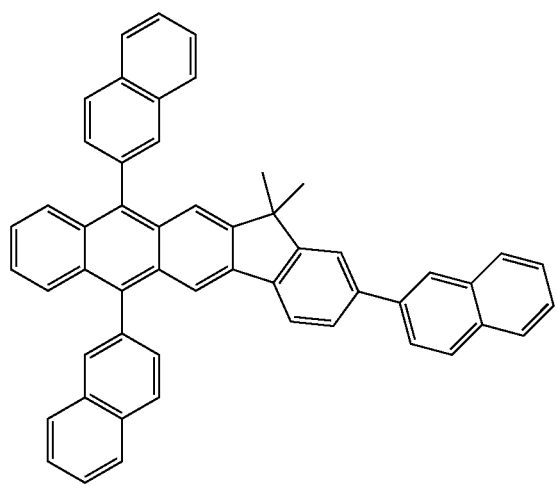
H29
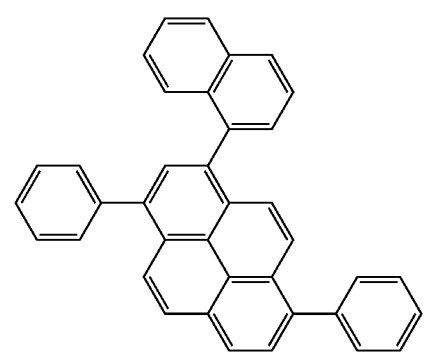
H30
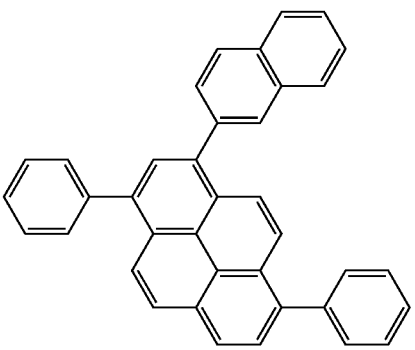
H31
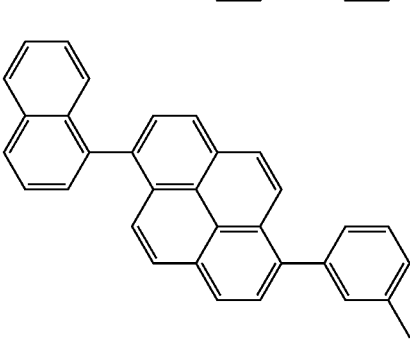
H32
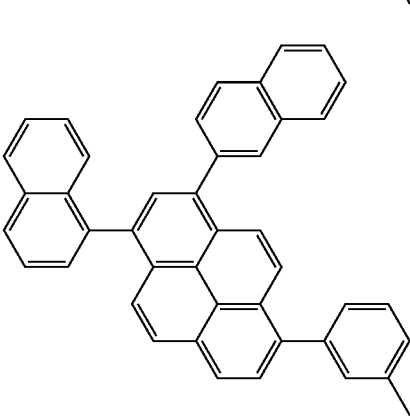
H33
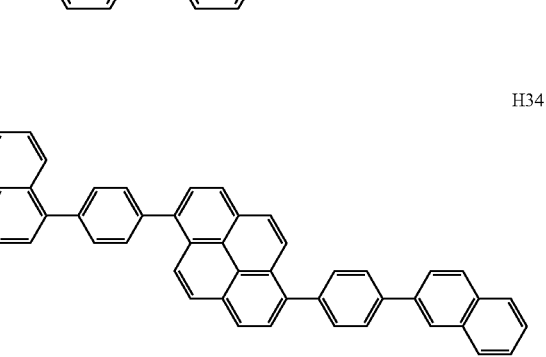
H34
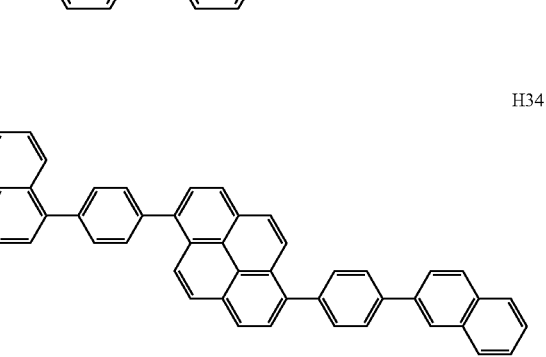

H35
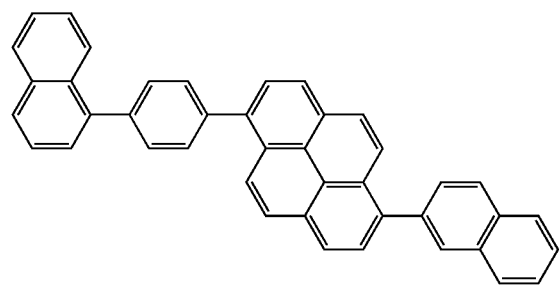
H36
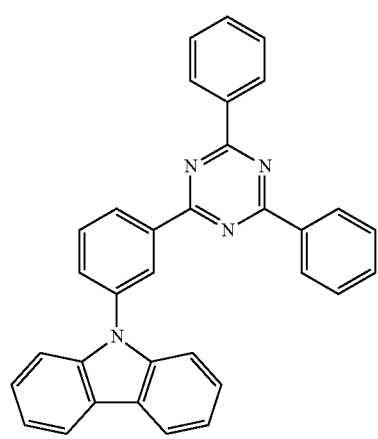
H37
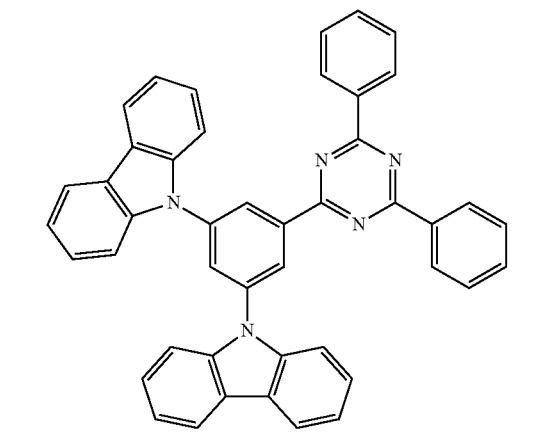
H38
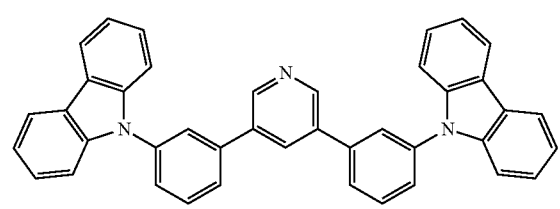
H39
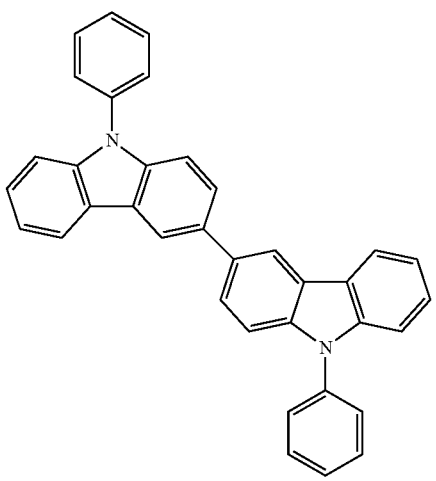
H40
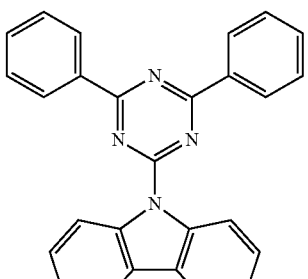
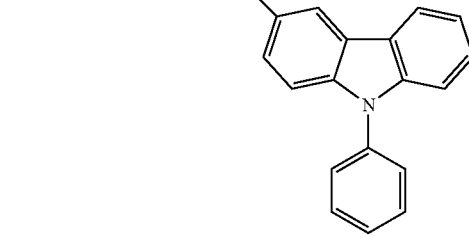
H41
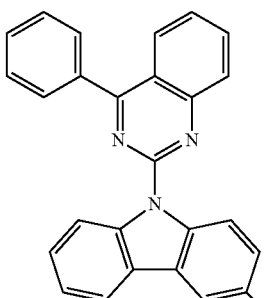
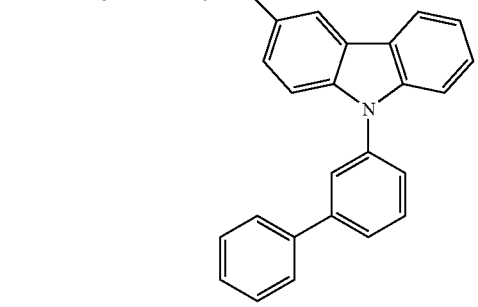

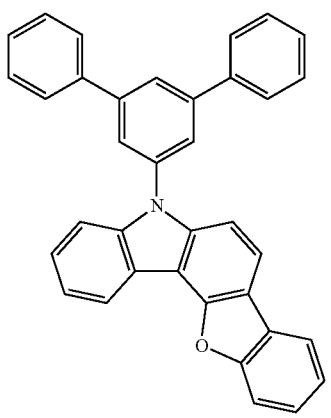
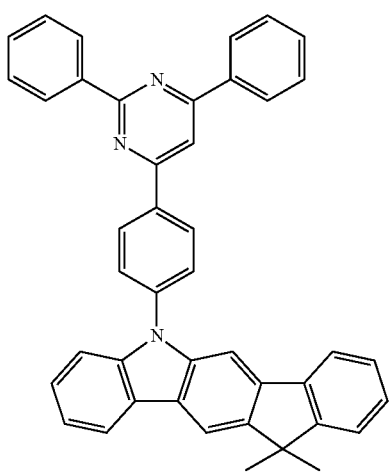
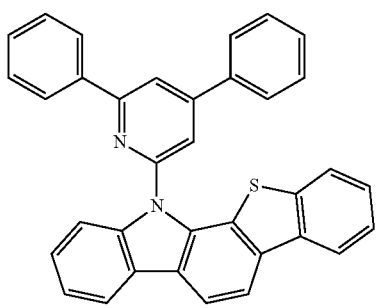
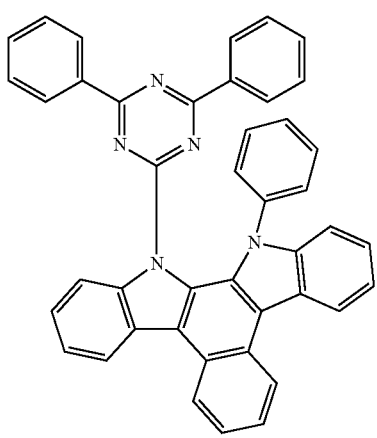
H42
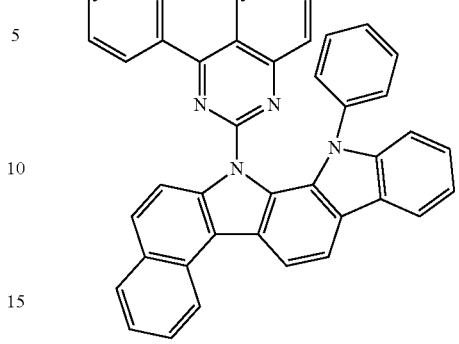
H43
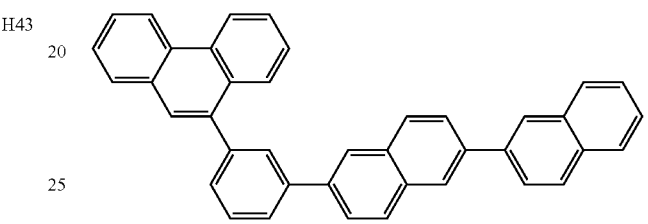
H44
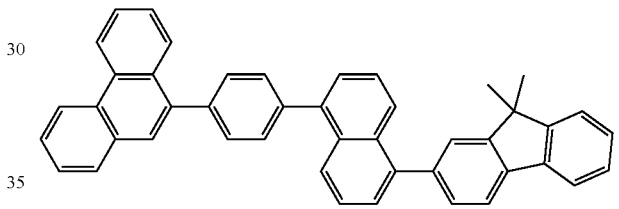
H45
H46
H47
H48
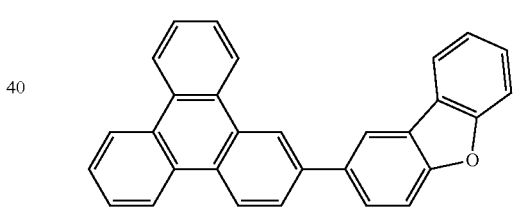
H49
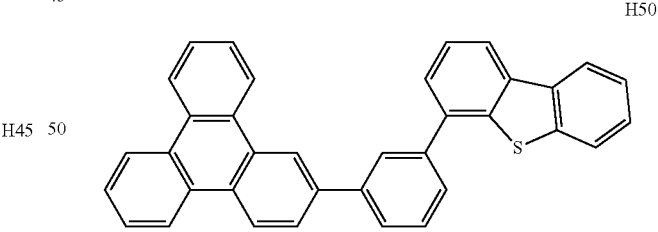
H50
H51
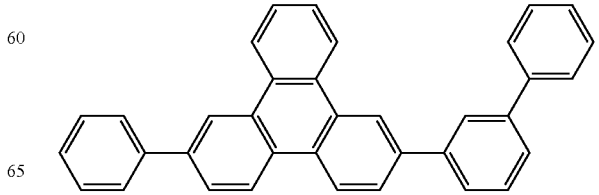

-continued

H52
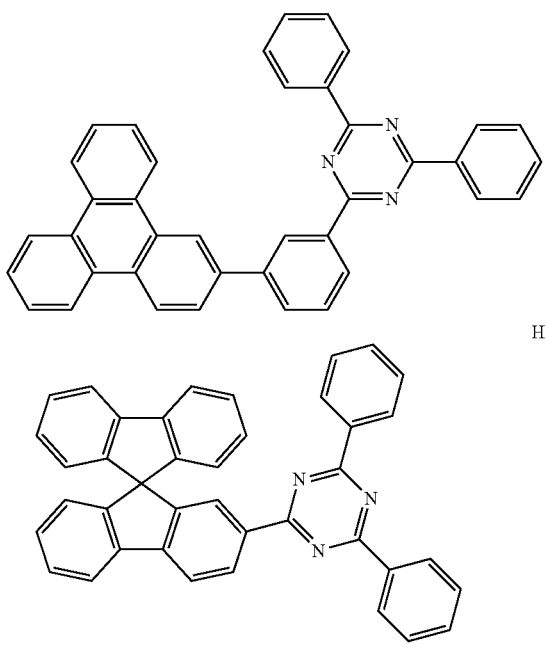

H53

H54
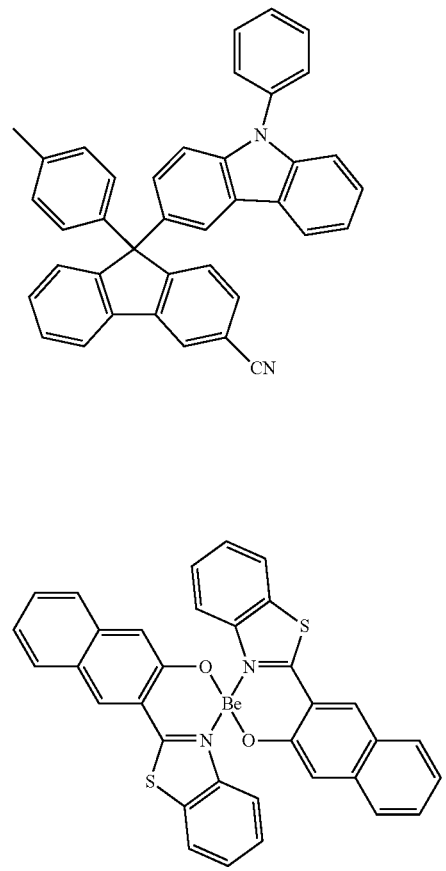

H55

[Phosphorescent Dopant Included in Emission Layer in Organic Layer 150]

The phosphorescent dopant may include an organometallic complex represented by Formula 401:

$$m(L_{401})_{xc1}(L_{402})_{xc2} \quad \text{Formula 401}$$

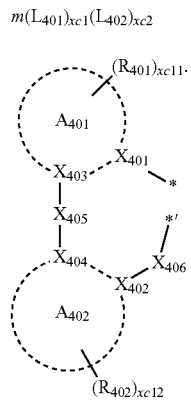

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer of 0 to 4, wherein, when xc2 is two or more, two or more $L_{402}$(S) may be identical to or different from each other, $X_{401}$ to $X_{404}$ may each independently be nitrogen or carbon, $X_{401}$ and $X_{403}$ may be linked each other via a single bond or a double bond, and $X_{402}$ and $X_{404}$ may be linked each other via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and

* and *' in Formula 402 each indicate a binding site to M in Formula 401.

In one embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen concurrently (e.g., at the same time).

In one or more embodiments, $R_{402}$ and $R_{402}$ in Formula 401 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but are not limited thereto.

In one or more embodiments, when xc1 in Formula 401 is two or more, two $A_{401}$(s) in two or more $L_{401}$(S) may optionally be linked each other via $X_{407}$, which is a linking group, or two $A_{402}$(S) in two or more $L_{401}$(S) may optionally be linked each other via $X_{408}$, which is a linking group (see Compounds PD1 to PD4 and PD7). $X_{407}$ and $X_{408}$ may each independently a single bond, *—O—*', *—S—*', *—C(=O)—*', *—N($Q_{413}$)-*', * C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and a phosphorus-containing material (for example, phosphine or phosphite), but embodiments of the present disclosure are not limited thereto.

In one or more embodiments, the phosphorescent dopant may be selected from, for example, Compounds PD1 to PD25, but embodiments of the present disclosure are not limited thereto:

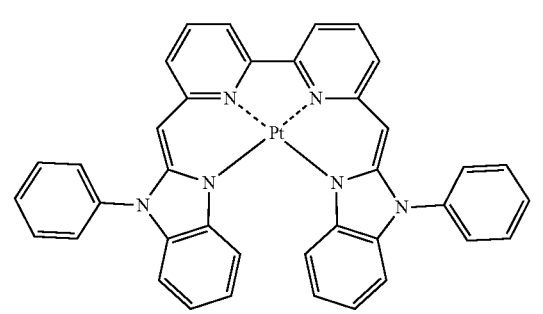

PD1

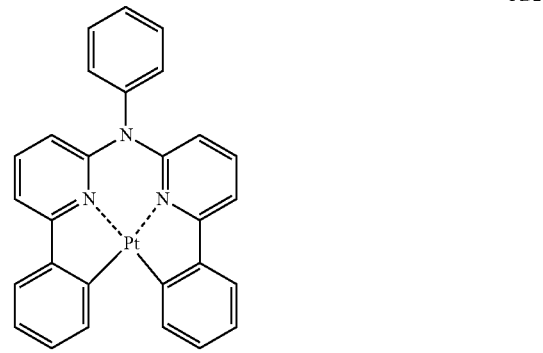

PD2

91
-continued
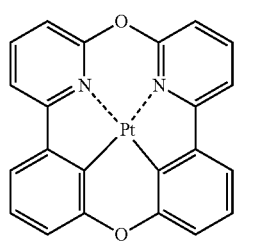
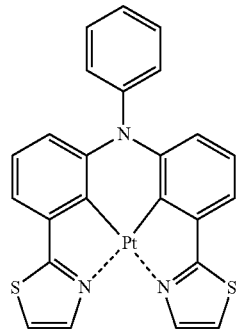
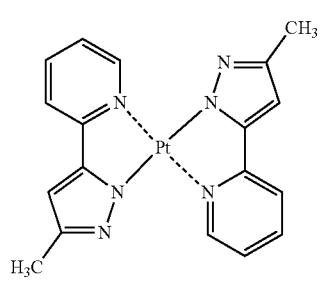
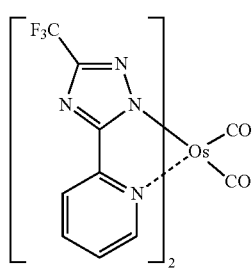
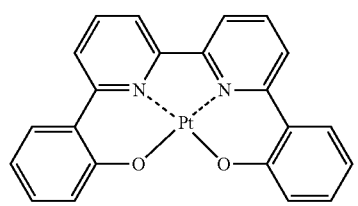
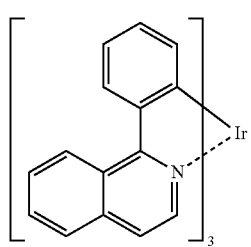
92
-continued
PD3
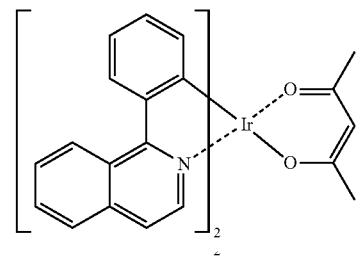
PD4
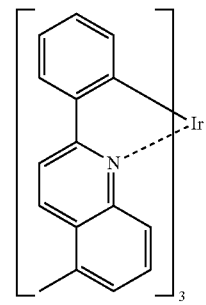
PD5
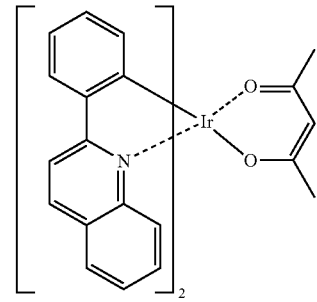
PD6
PD7
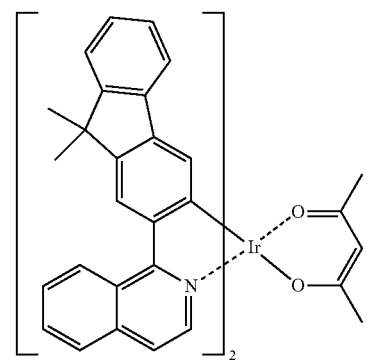
PD8
PD9
PD10
PD11
PD12
PD13
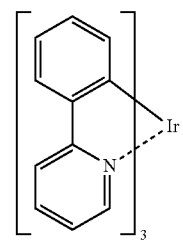

PD14 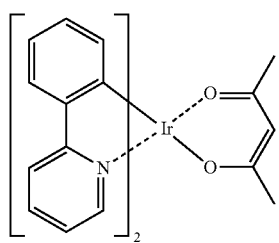
PD15 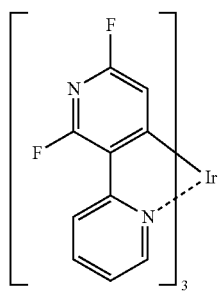
PD16 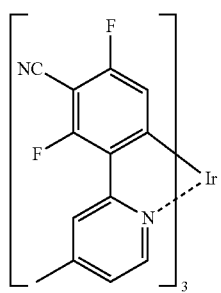
PD17 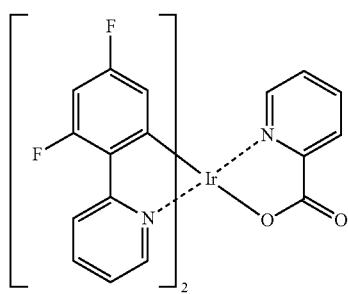
PD18 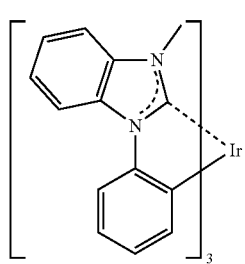
PD19 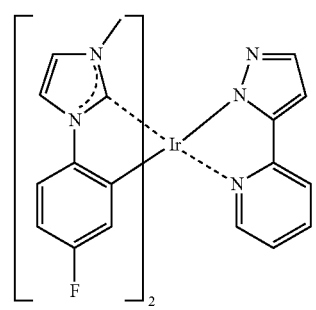
PD20 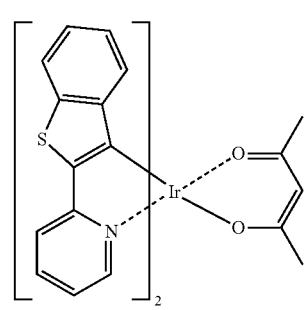
PD21 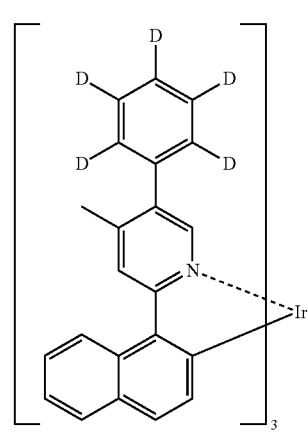
PD22 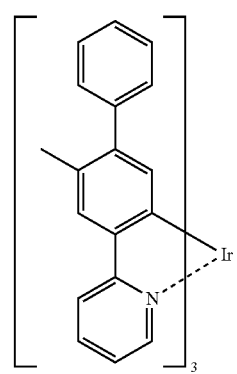

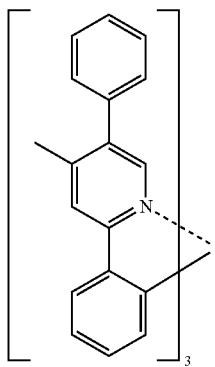

PD23

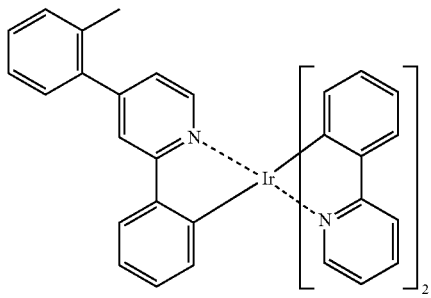

PD24

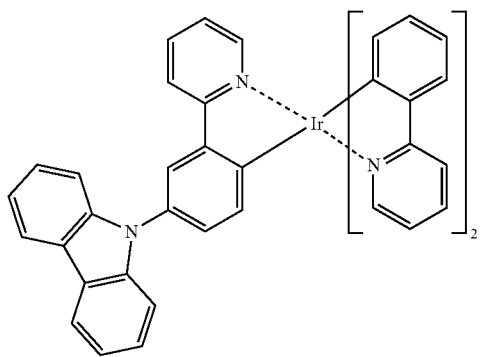

PD25

Fluorescent Dopant in Emission Layer

The fluorescent dopant may include an arylamine compound or a styrylamine compound.

The fluorescent dopant may include a compound represented by Formula 501:

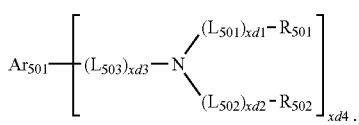

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

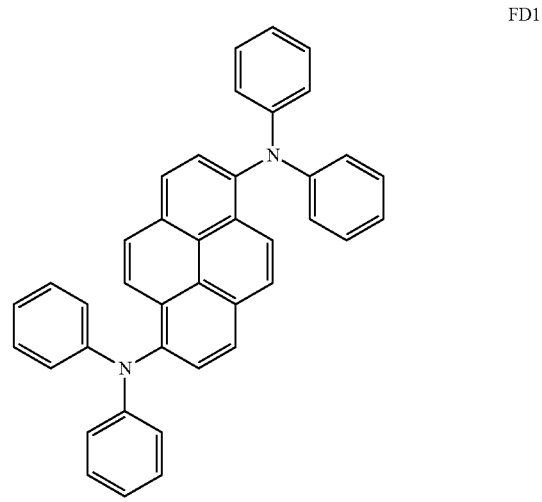

FD1

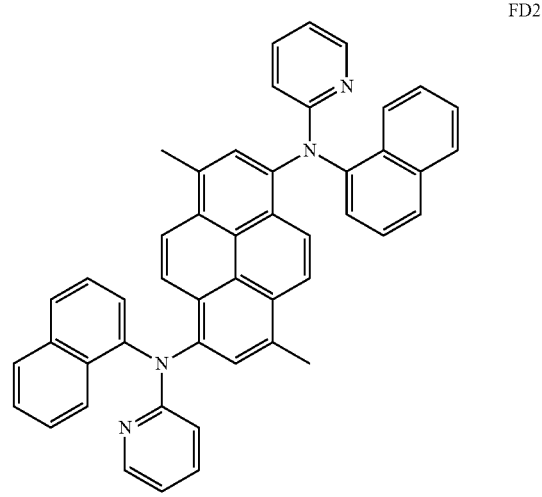

FD2

-continued
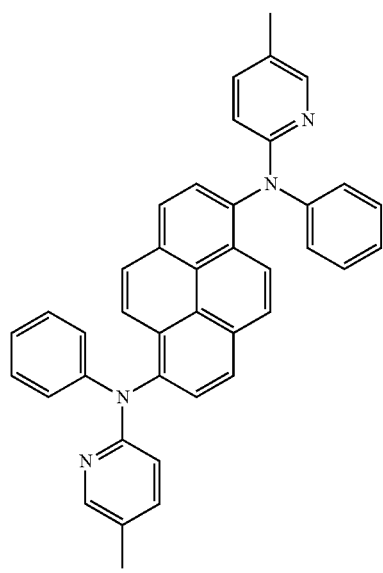
FD3
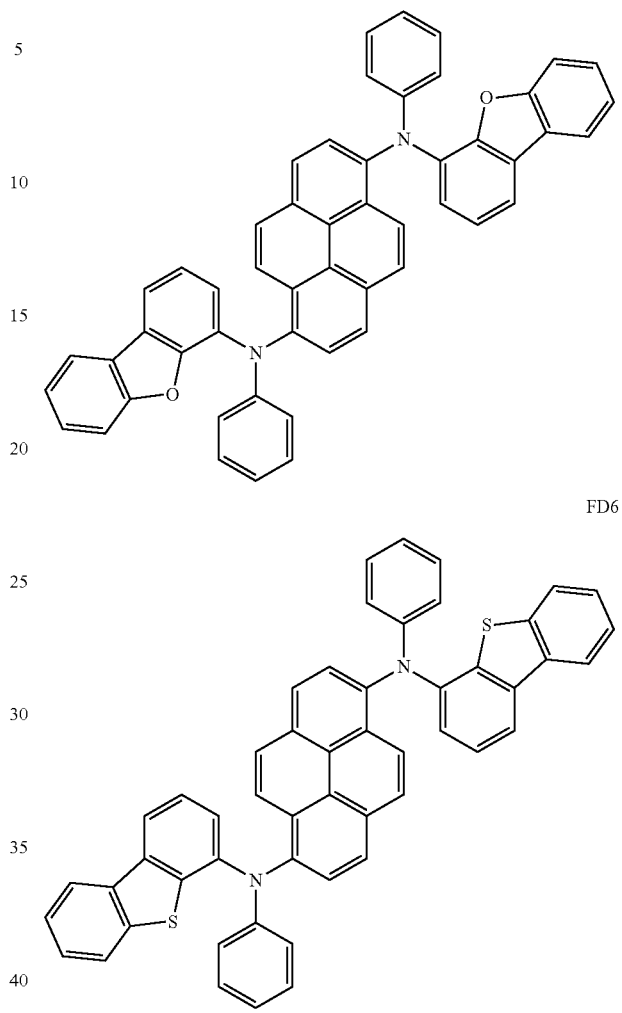
FD5
FD6
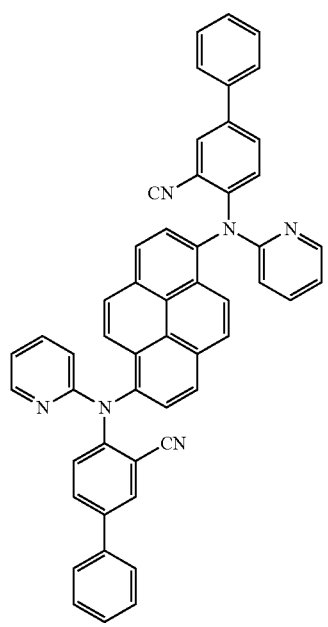
FD4
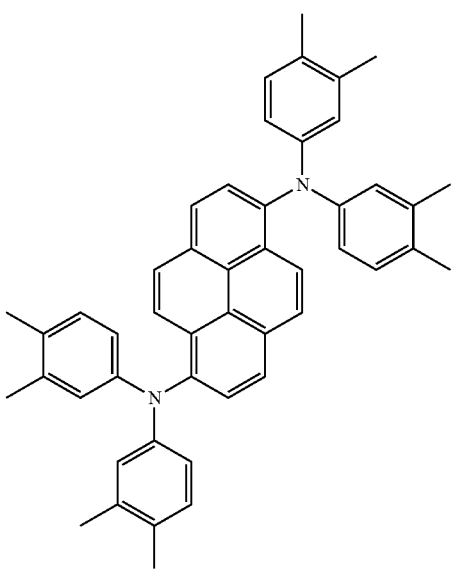
FD7

-continued
FD8
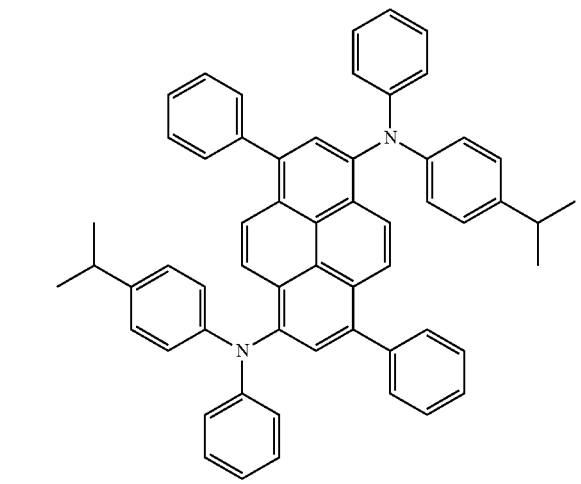
FD9
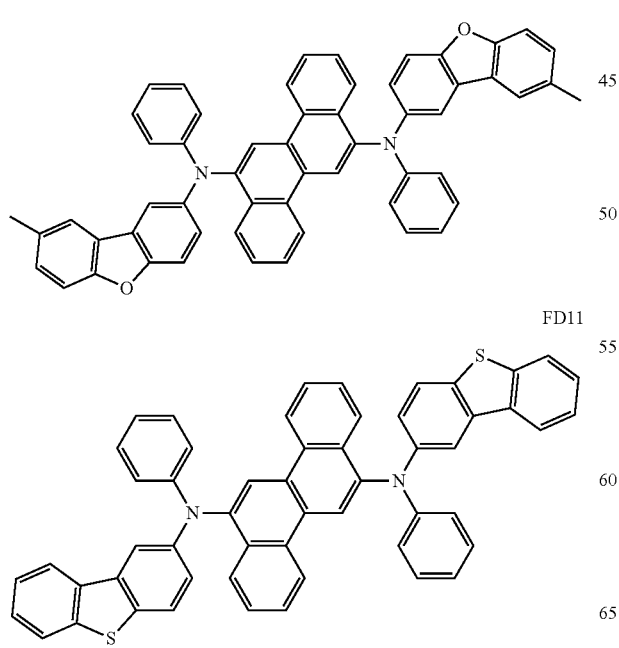
FD10
FD11
FD12
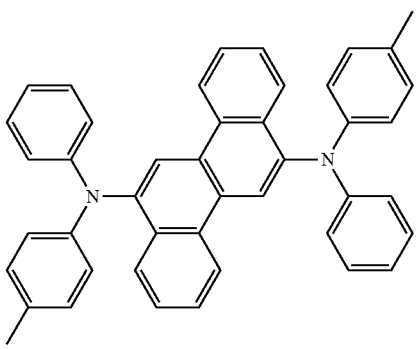
FD13
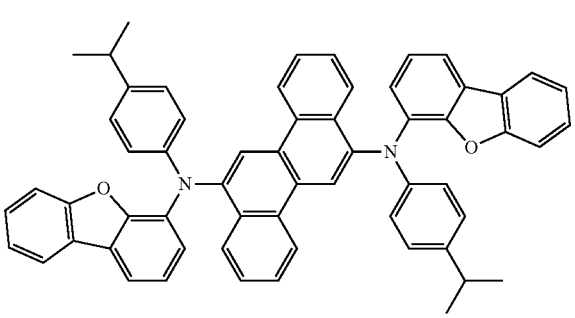
FD14
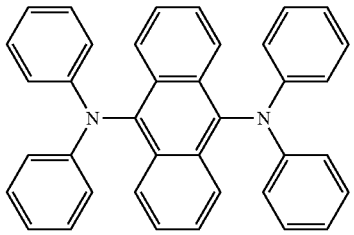
FD15
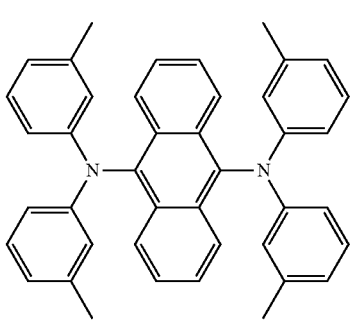
FD16
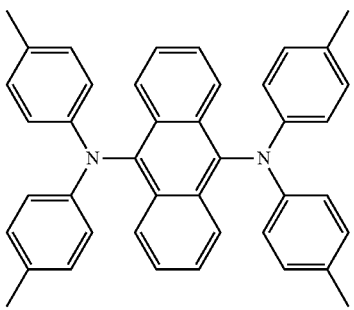

FD17 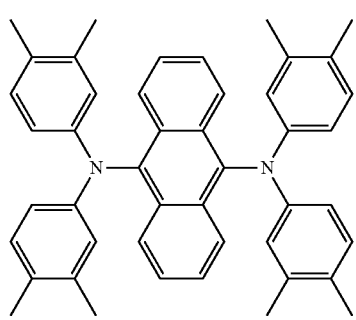
FD18 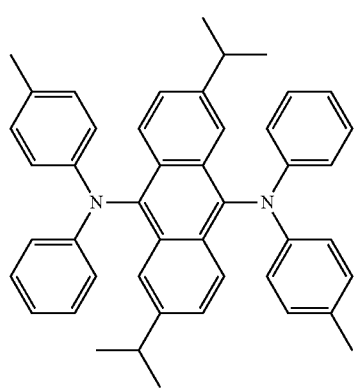
FD19 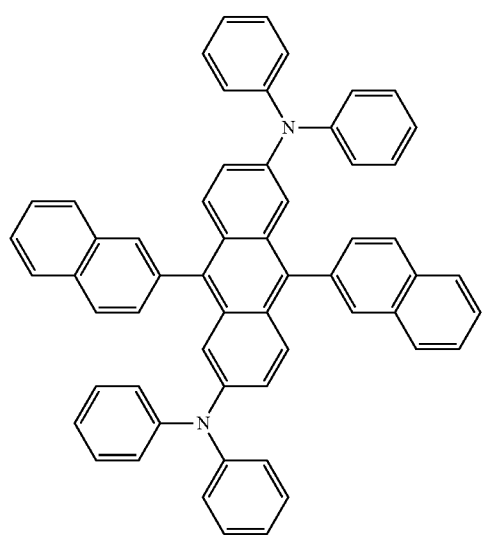
FD20 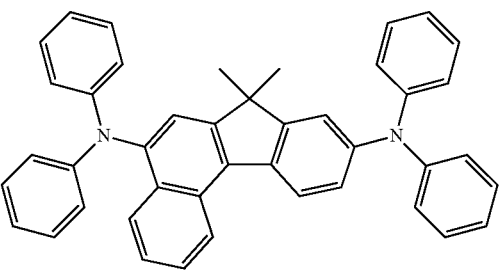
FD21 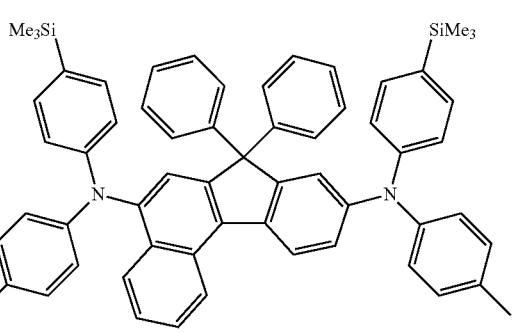
FD22 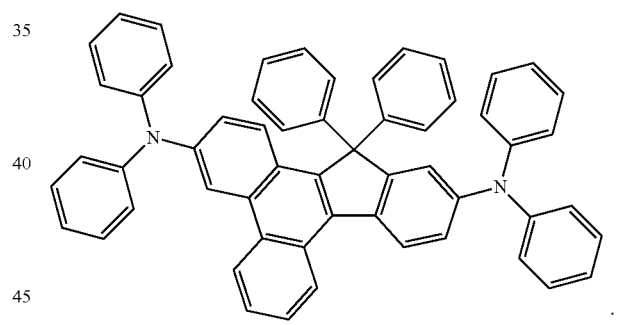
In one or more embodiments, the fluorescent dopant may be selected from the following compounds, but embodiments of the present disclosure are not limited thereto:
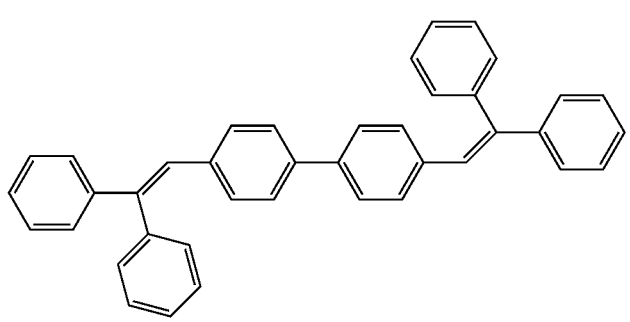
DPVBi -continued

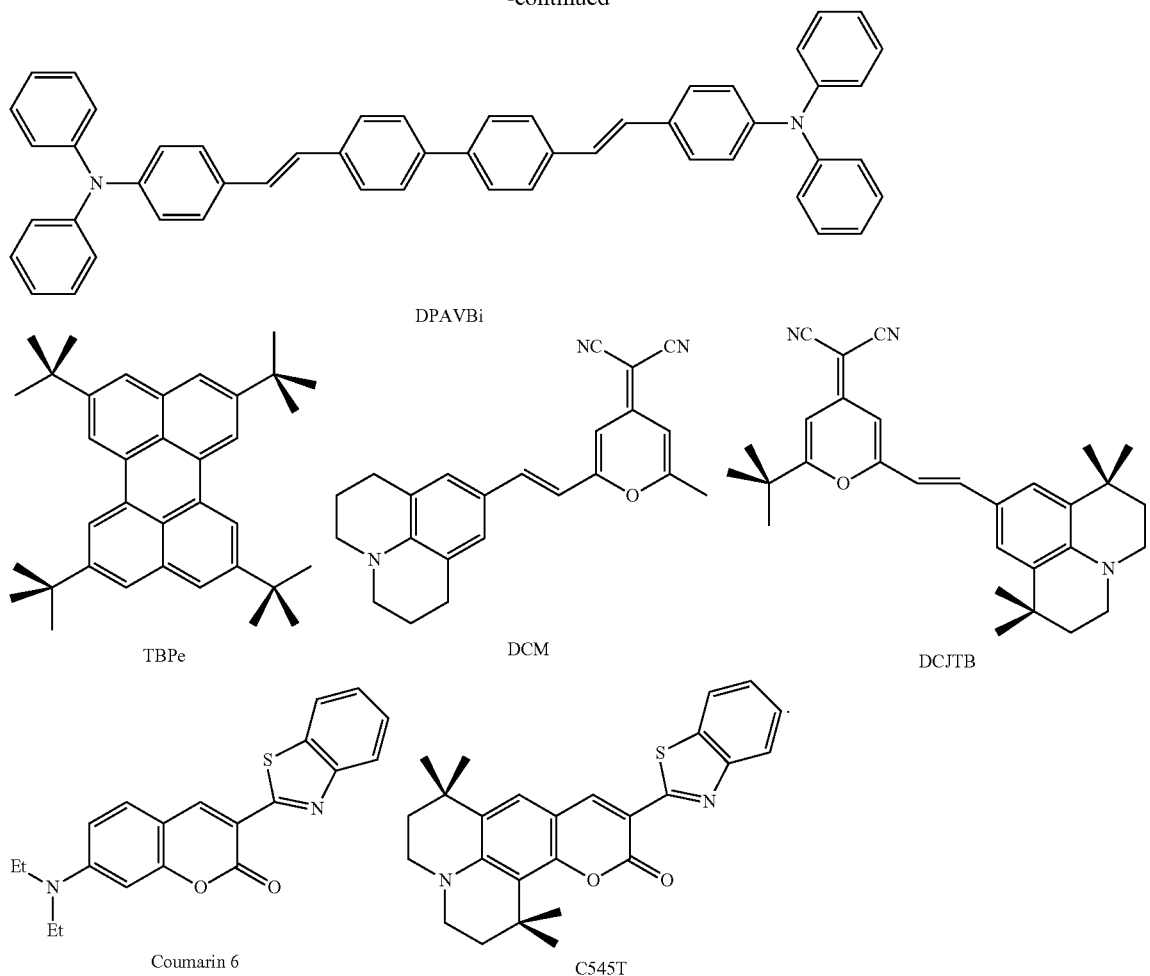

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region may include a heterocyclic compound represented by Formula 1.

In one embodiment, the electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring," as used herein, refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other (e.g., combined together), or iii) a heteropolycyclic group in which at least one of 5-membered to 7-membered heteromonocyclic groups, each having at least one *—N=*' moiety, is condensed with (e.g., combined with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, a thiadiazole, an imidazopyridine, an imidazopyrimidine, and an azacarbazole, but are not limited thereto.

For example, the electron transport region may include a compound represented by Formula 601:

$$[Ar_{601}]_{xe11}\text{-}[(L_{601})_{xe1}\text{-}R_{601}]_{xe21}.$$  Formula 601

In Formula 601, $Ar_{601}$ may be a substituted or unsubstituted $C_5\text{-}C_{60}$ carbocyclic group or a substituted or unsubstituted $C_1\text{-}C_{60}$ heterocyclic group, xe11 may be 1, 2, or 3, $L_{601}$ may each independently be selected from a substituted or unsubstituted $C_3\text{-}C_{10}$ cycloalkylene group, a substituted or unsubstituted $C_1\text{-}C_{10}$ heterocycloalkylene group, a substituted or unsubstituted $C_3\text{-}C_{10}$ cycloalkenylene group, a substituted or unsubstituted $C_1\text{-}C_{10}$ heterocycloalkenylene group, a substituted or unsubstituted $C_6\text{-}C_{60}$ arylene group, a substituted or unsubstituted $C_1\text{-}C_{60}$ heteroarylene group, a substituted or unsubstituted divalent non-aromatic condensed polycyclic group, and a substituted or unsubstituted divalent non-aromatic condensed heteropolycyclic group;

xe1 may be an integer of 0 to 5, $R_{601}$ may be selected from a substituted or unsubstituted $C_3\text{-}C_{10}$ cycloalkyl group, a substituted or unsubstituted $C_1\text{-}C_{10}$ heterocycloalkyl group, a substituted or unsubstituted $C_3\text{-}C_{10}$ cycloalkenyl group, a substituted or unsubstituted $C_1\text{-}C_{10}$ heterocycloalkenyl group, a substituted or unsubstituted $C_6\text{-}C_{60}$ aryl group, a substituted or unsubstituted $C_6\text{-}C_{60}$ aryloxy group, a substituted or unsubstituted $C_6\text{-}C_{60}$ arylthio group, a substituted or unsubstituted $C_1\text{-}C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, and $-P(=O)(Q_{601})(Q_{602})$, $Q_{601}$ to $Q_{603}$ may each independently be a $C_1\text{-}C_{10}$ alkyl group, a $C_1\text{-}C_{10}$ alkoxy group, a phenyl group, a biphenyl group, a terphenyl group, or a naphthyl group, and xe21 may be an integer of 1 to 5.

In one embodiment, at least one of $Ar_{601}(s)$ in the number of xe11 and $R_{601}(s)$ in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1\text{-}C_{20}$ alkyl group, a $C_1\text{-}C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, and $-P(=O)(Q_{31})(Q_{32})$, and $Q_{31}$ to $Q_{33}$ may each independently be selected from a $C_1\text{-}C_{10}$ alkyl group, a $C_1\text{-}C_{10}$ alkoxy group, a phenyl group, a biphenyl group, a terphenyl group, and a naphthyl group.

When xe11 in Formula 601 is two or more, two or more $Ar_{601}(s)$ may be linked each other via a single bond.

In one or more embodiments, $Ar_{601}$ in Formula 601 may be an anthracene group.

In one or more embodiments, a compound represented by Formula 601 may be represented by Formula 601-1:

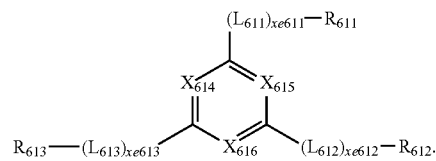

Formula 601-1

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:
- a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and
- a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

but embodiments of the present disclosure are not limited thereto.

In one or more embodiments, xe1 and xe611 to xe613 in Formulae 601 and 601-1 may each independently be 0, 1, or 2.

In one or more embodiments, in Formulae 601 and 601-1, $R_{601}$ and $R_{611}$ to $R_{613}$ may each independently be selected from:
- a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may respectively be the same as defined above.

The electron transport region may include at least one compound selected from Compounds ET1 to ET36, but embodiments of the present disclosure are not limited thereto:

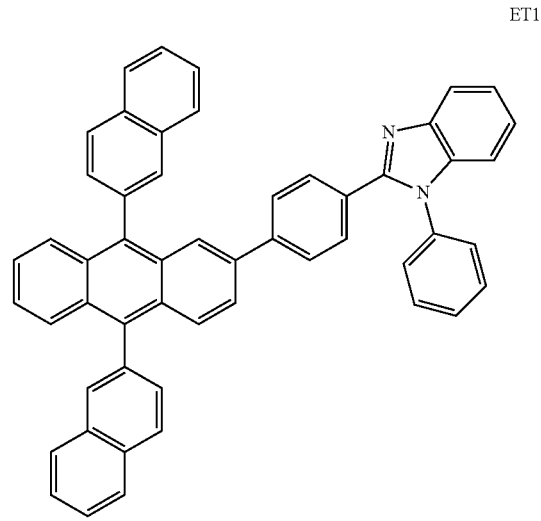

ET1

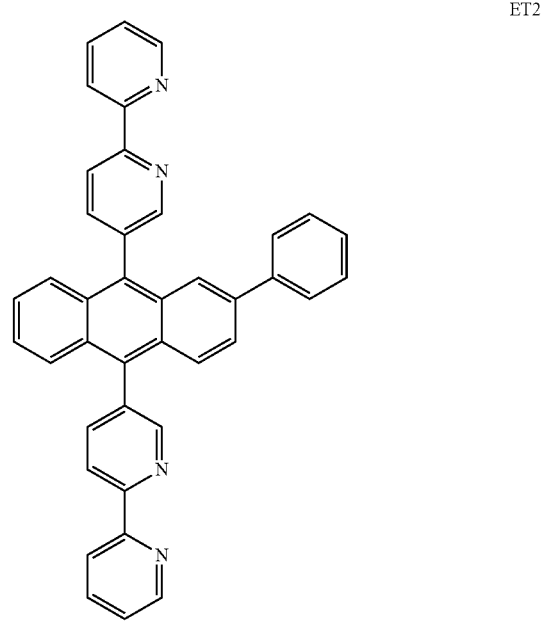

ET2

ET3
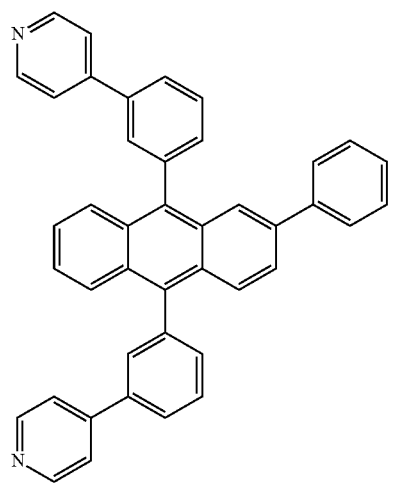
ET4
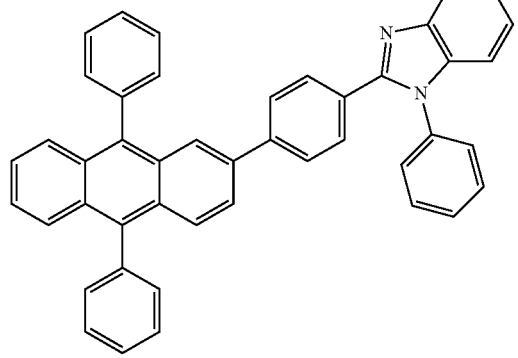
ET5
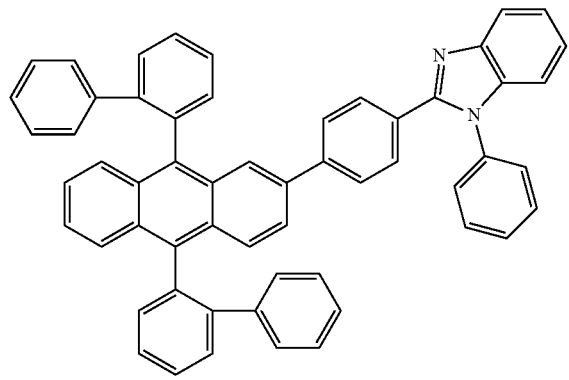
ET6
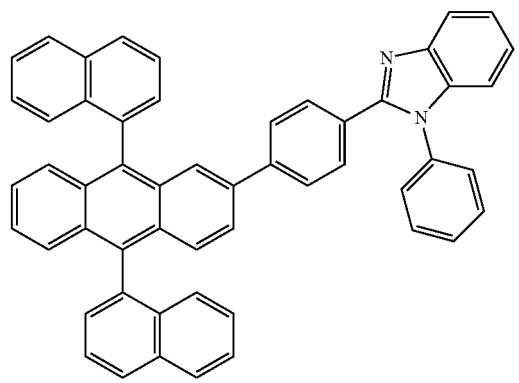
ET7
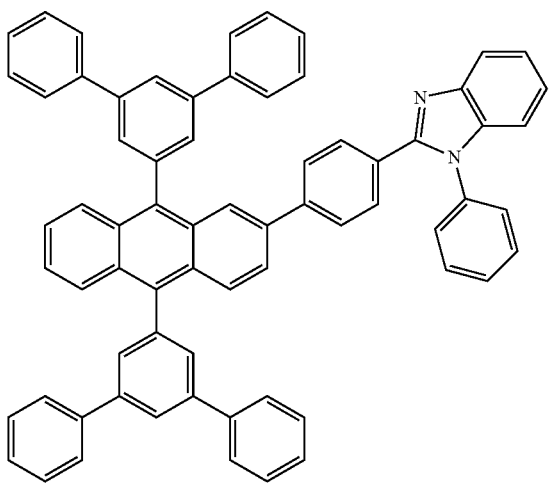
ET8
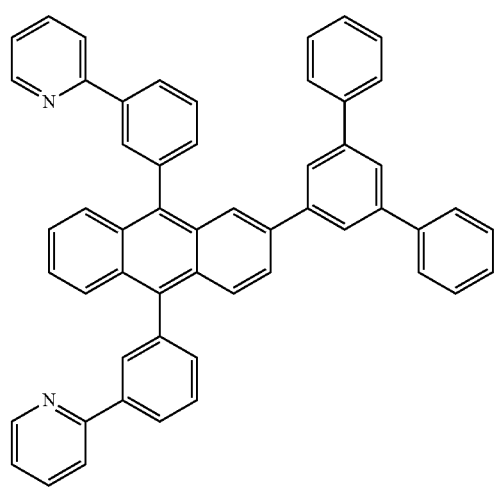

ET9
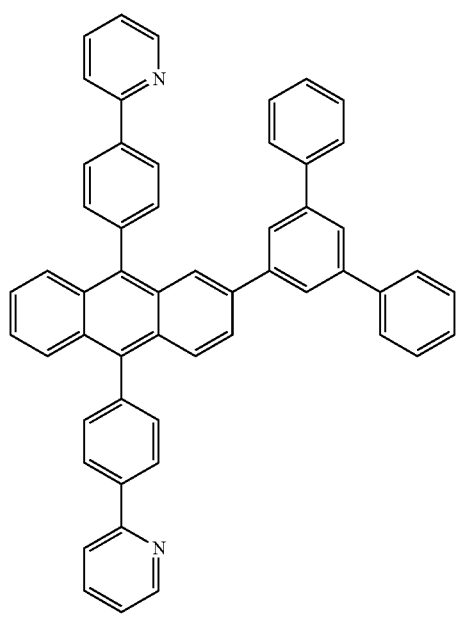
ET10
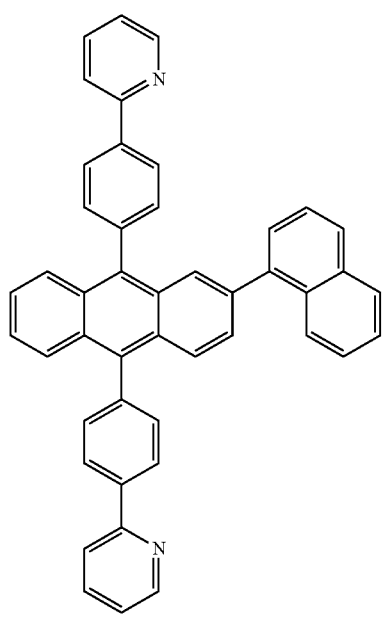
ET11
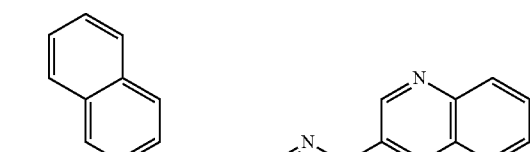
ET12
ET13
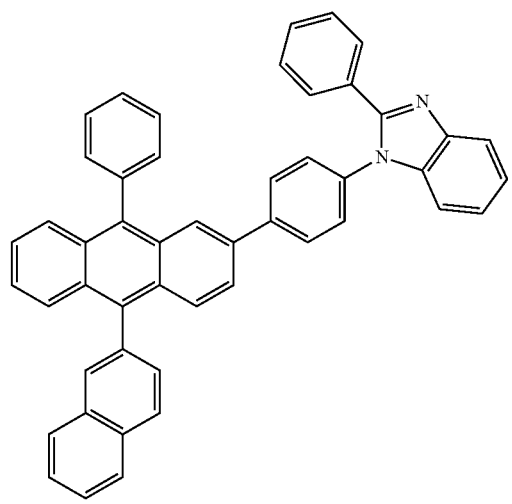

ET14
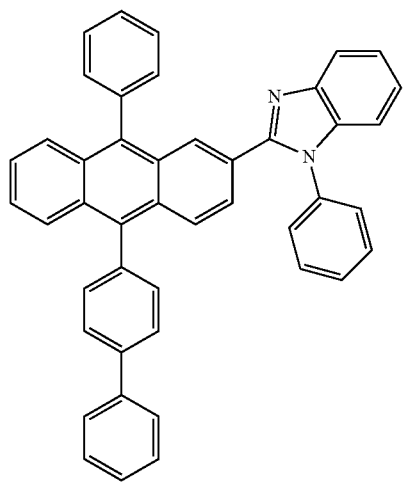
ET15
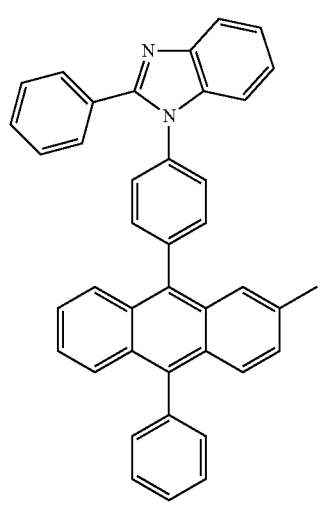
ET16
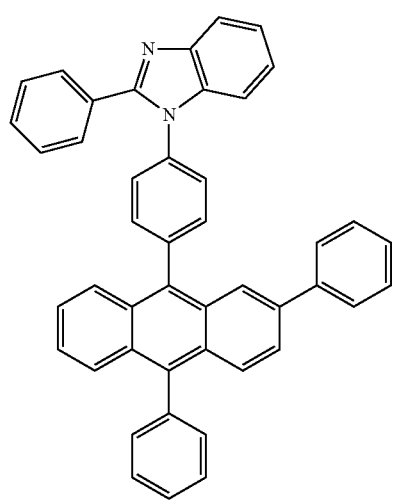
ET17
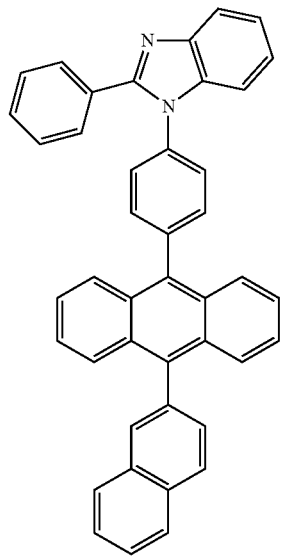
ET18
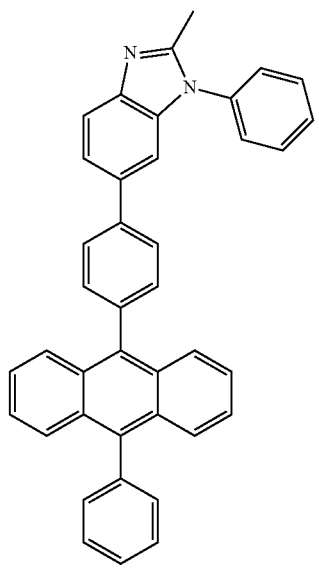
ET19
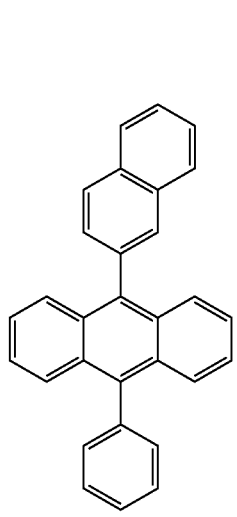

ET20
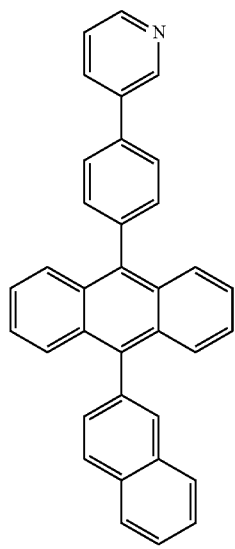
ET21
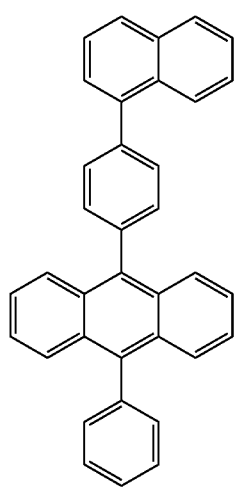
ET22
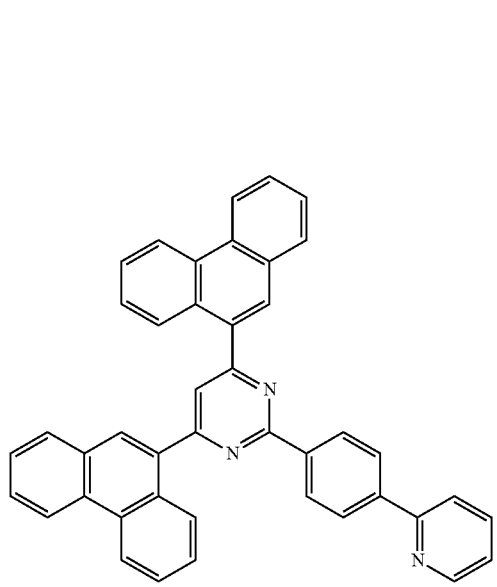
ET23
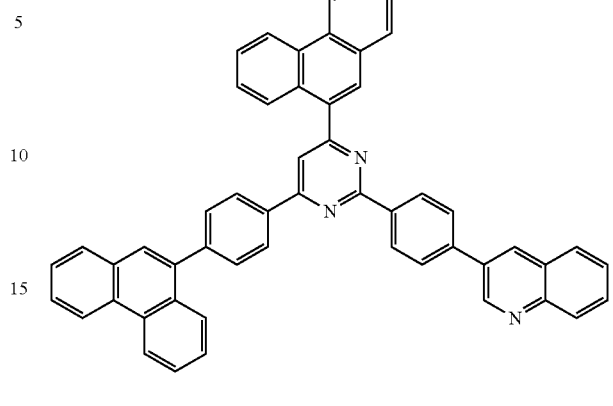
ET24
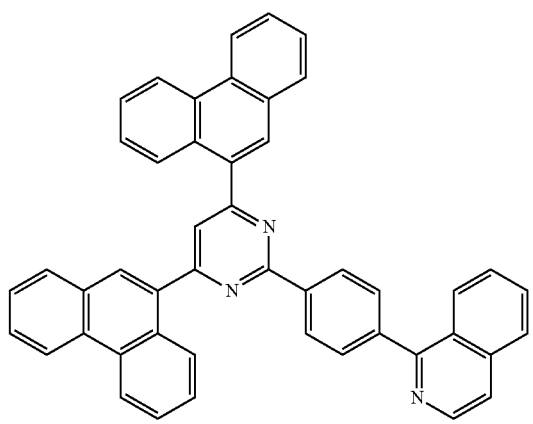
ET25
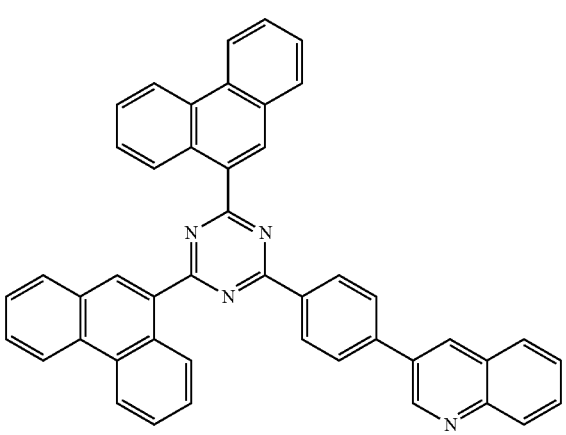

-continued
ET26
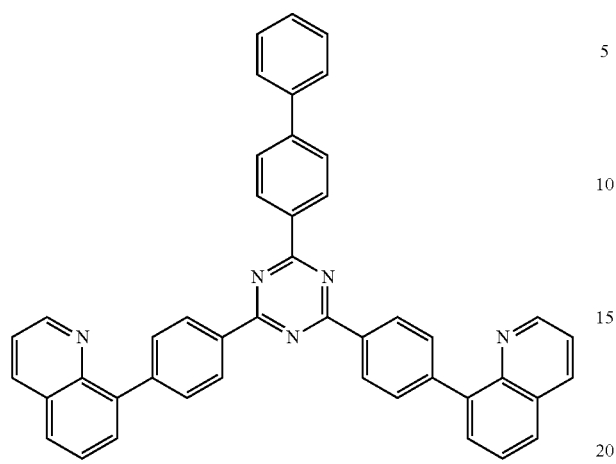
ET27
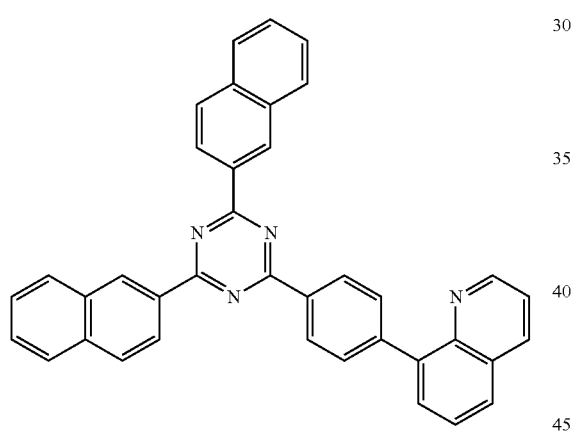
ET28
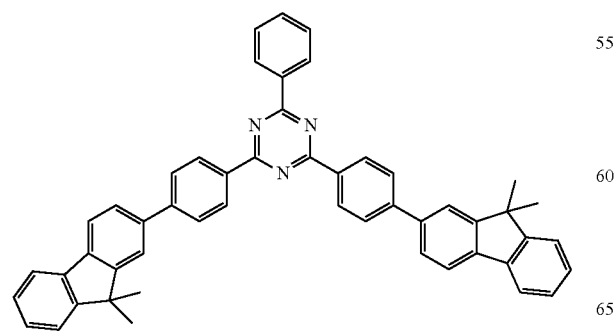
ET29
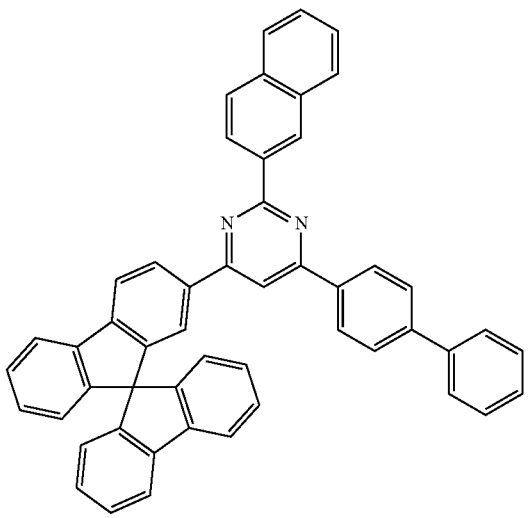
ET30
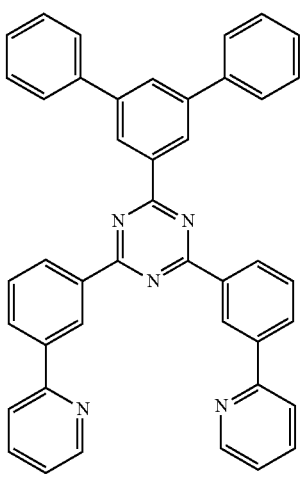
ET31
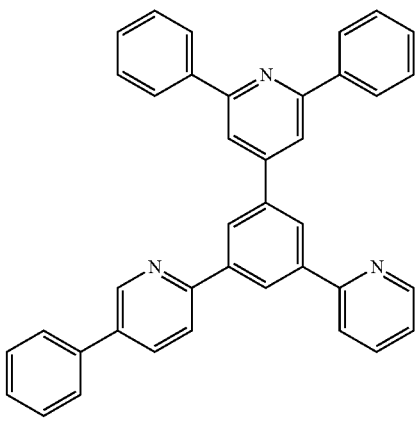

ET32
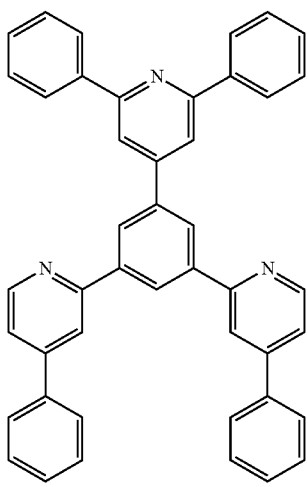
ET33
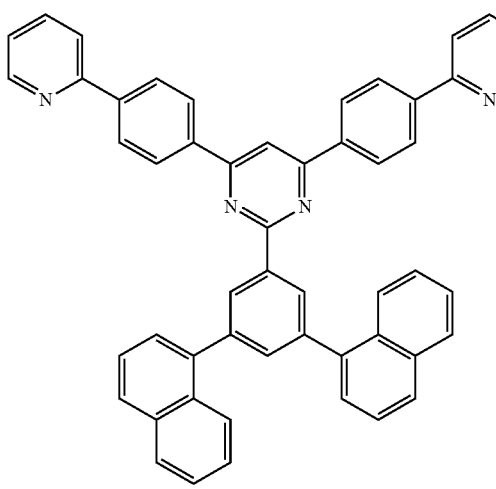
ET34
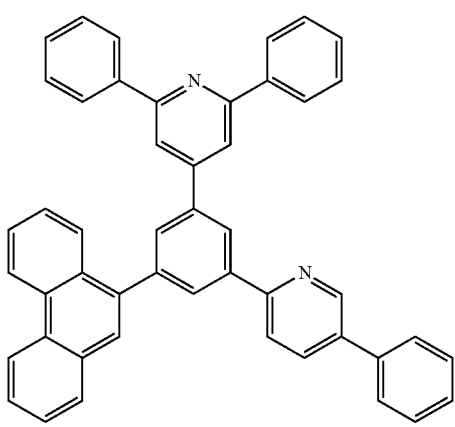
ET35
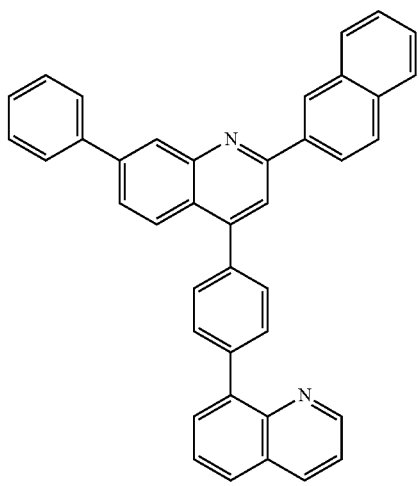
ET36
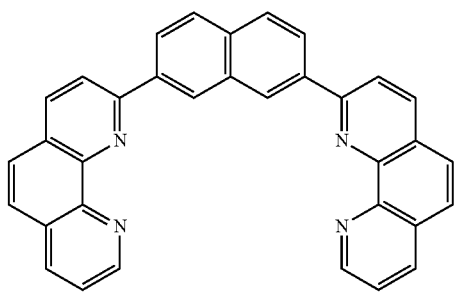
In one or more embodiments, the electron transport region may include at least one selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ:
Alq$_3$
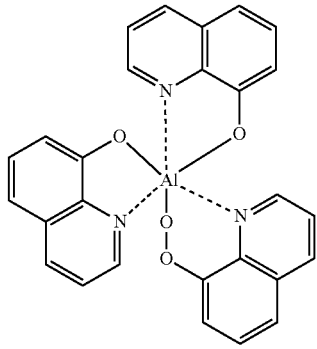

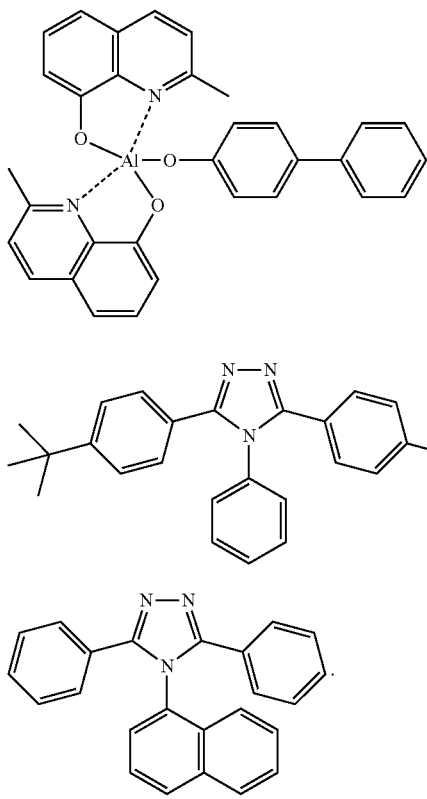

BAlq

TAZ

NTAZ

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2:

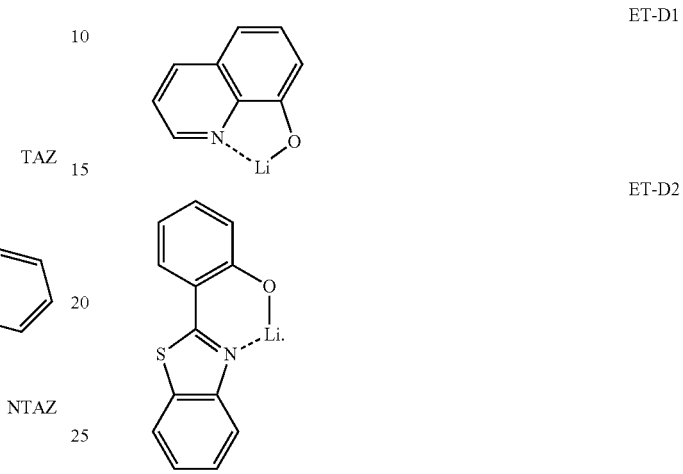

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-}$ $_x$O (0<x<1), or Ba$_x$Ca$_{1-x}$O (0<x<1). In one embodiment, the alkaline earth-metal compound may be selected from BaO, SrO, and CaO, but embodiments of the present disclosure are not limited thereto.

The rare earth metal compound may be selected from YbF$_3$, ScF$_3$, ScO$_3$, Y$_2$O$_3$, Ce$_2$O$_3$, GdF$_3$, and TbF$_3$. In one embodiment, the rare earth metal compound may be selected from YbF$_3$, ScF$_3$, TbF$_3$, YbI$_3$, ScI$_3$, and TbI$_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have suitable or satisfactory electron injection characteristics without a substantial increase in driving voltage.

Second Electrode 190

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figures 3, 4:
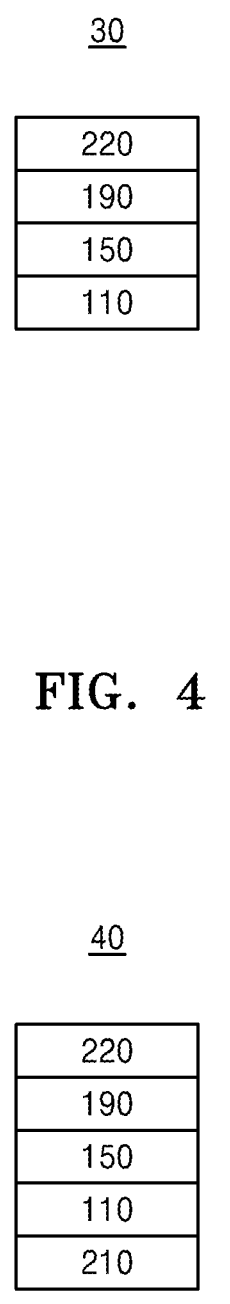

Description of FIGS. 2-4

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Referring FIGS. 2-4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto:

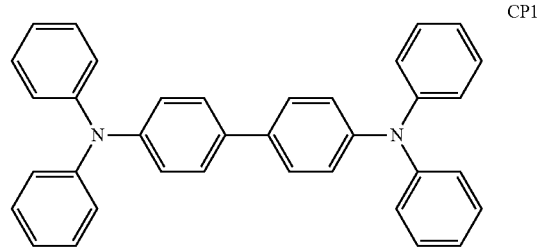

CP1

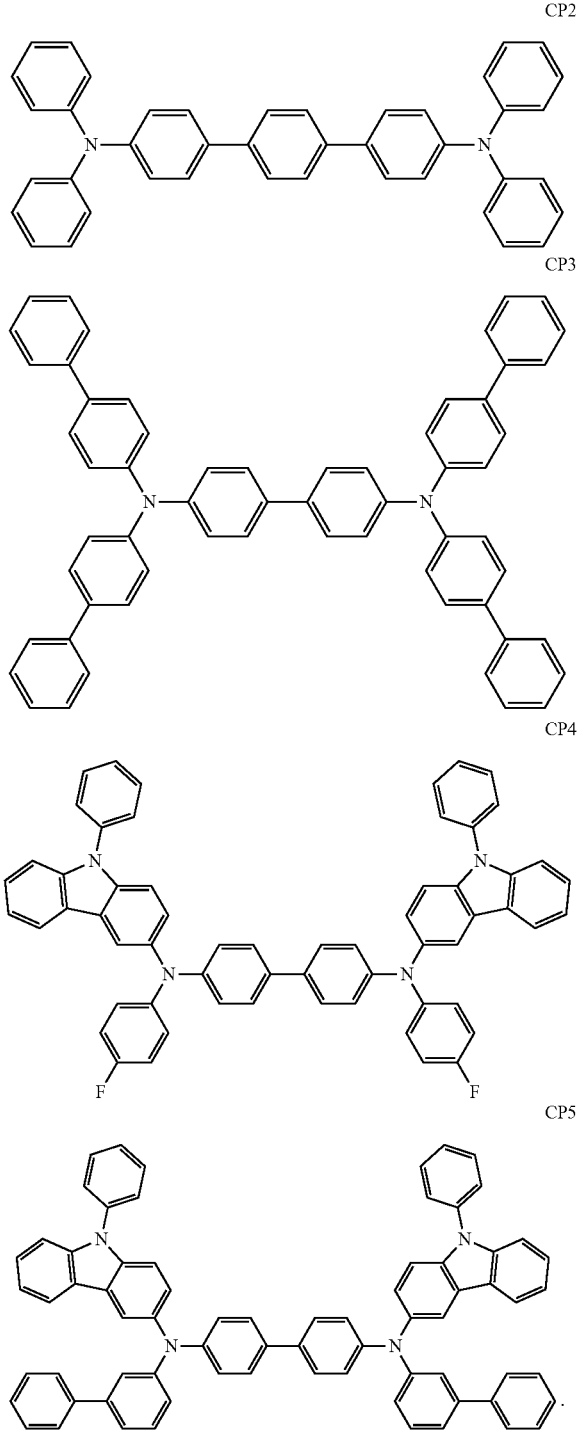

Hereinbefore, the organic light-emitting device according to an embodiment has been described in connection with FIGS. 1-4. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

General Definition of Some of the Substituents

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_{2-60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein refers to a monovalent monocyclic group that has 3 to 10 carbon atoms and at least one carbon-carbon double bond in the ring thereof and no aromaticity (e.g., entire ring, group, or molecule is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group used herein indicates -$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire group or molecule is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire group or molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, substituted divalent non-aromatic condensed polycyclic group, substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical (e.g., substantially identical) molar equivalent of B was used in place of A.

EXAMPLES

Synthesis Example 1: Synthesis of Compound 2

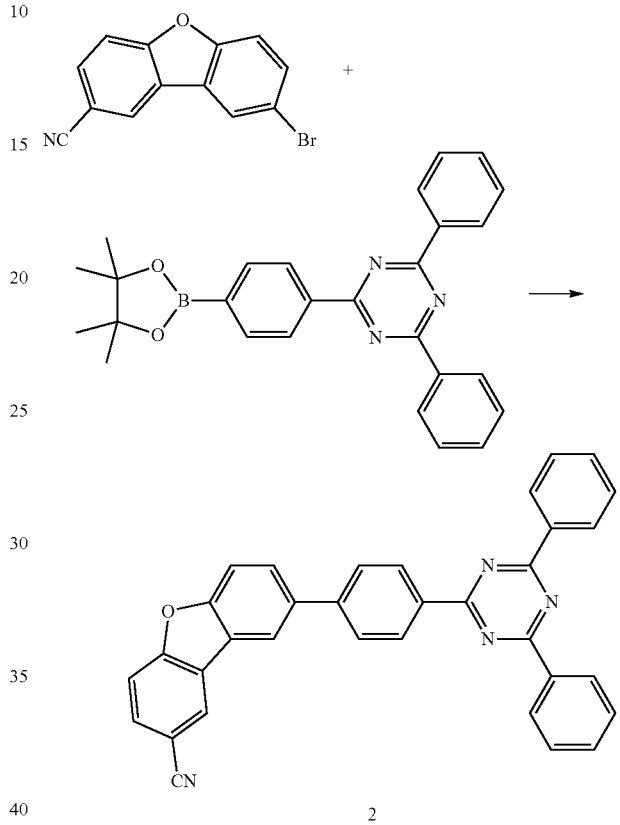

2.71 g (10.0 mmol) of 8-bromodibenzo[b,d]furan-2-carbonitrile, 4.35 g (10.0 mmol) of 2,4-diphenyl-6-(4-(4,4,5,5-tetramethyl-1,3,2-dioxaborolan-2-yl)phenyl)-1,3,5-triazine, 0.58 g (0.50 mmol) of Pd(PPh$_3$)$_4$, 0.16 g (0.5 mmol) of tetrabutylammonium bromide (TBAB), and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel column chromatography, thereby obtaining 3.80 g (yield: 76%) of Compound 2. The obtained compound was identified by MS/FAB and $^1$H NMR.

$C_{47}H_{30}FN$ cal. 500.16, found 500.16.

Synthesis Example 2: Synthesis of Compound 10

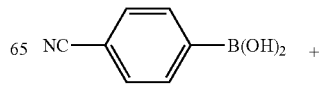

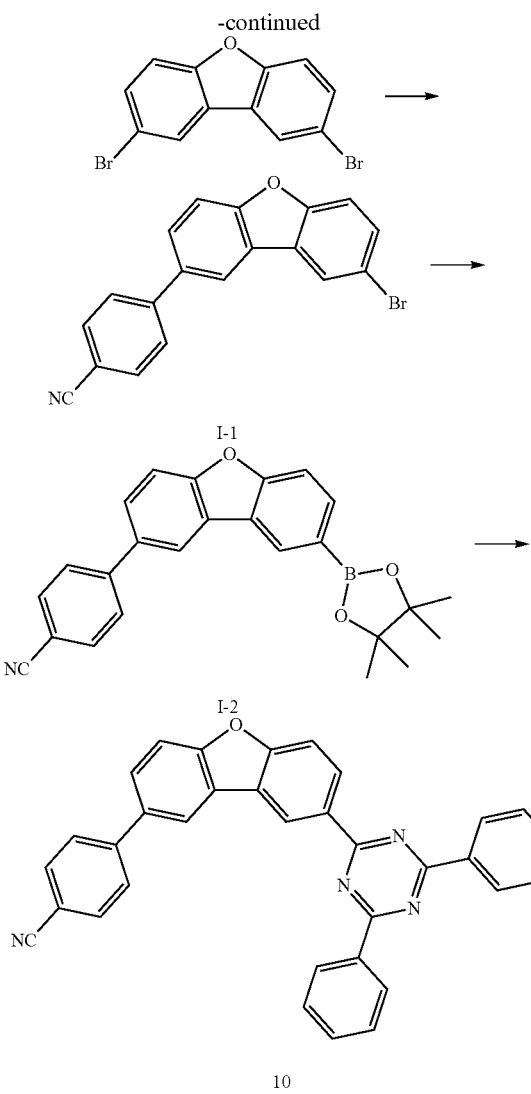

was performed thereon three times by using diethylether (30 mL). A resulting washed diethylether layer was dried by using MgSO$_4$, and then, dried again under reduced pressure. A resulting product was separated and purified by silica gel column chromatography, thereby obtaining 3.04 g (yield: 77%) of Intermediate I-2. The obtained compound was identified by LC-MS.

$C_{25}H_{22}BNO_3$: M+1 395.2

Synthesis of Compound 10

3.95 g (10.0 mmol) of Intermediate I-2, 2.67 g (10.0 mmol) of 2-chloro-4,6-diphenyl-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours.

The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel column chromatography, thereby obtaining 3.55 g (yield: 71%) of Compound 10. The produced compound was identified by MS/FAB.

$C_{34}H_{20}N_4O$ cal. 500.16, found 500.15.

Synthesis Example 3: Synthesis of Compound 16

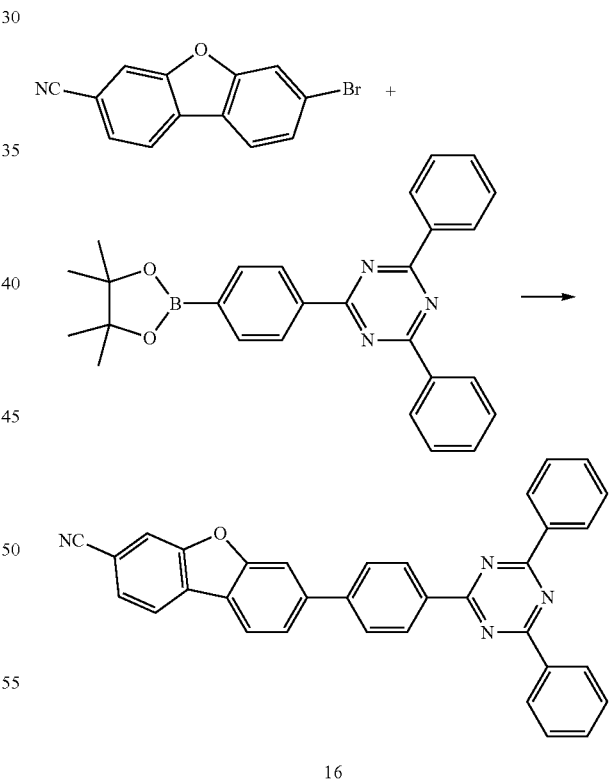

Synthesis of Intermediate I-1

1.47 g (10.0 mmol) of (4-cyanophenyl)boronic acid, 6.46 g (20.0 mmol) of 2,8-dibromodibenzo[b,d]furan, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours.

The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 1.73 g (yield: 50%) of Intermediate I-1. The obtained compound was identified by LC-MS.

$C_{12}H_6Br_2O$: M+1 323.9

Synthesis of Intermediate I-2

3.47 g (10 mmol) of Intermediate I-1 was dissolved in 50 mL of THF, and 4 mL of nBuLi (2.5 M in Hexane) was added thereto at a temperature of −78° C. After one hour at the same temperature, 2.0 mL (10 mmol) of 2-isopropoxy-4,4,5,5-tetramethyl-1,3,2-dioxaborolane was added thereto. Then, the mixed solution was stirred at room temperature for 5 hours, and water was added thereto. A washing process 2.71 g (10.0 mmol) of 7-bromodibenzo[b,d]furan-3-carbonitrile, 4.35 g (10.0 mmol) of 2,4-diphenyl-6-(4-(4,4,5,5-tetramethyl-1,3,2-dioxaborolan-2-yl)phenyl)-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 3.25 g (yield: 65%) of Compound 16. The obtained compound was identified by MS/FAB.

$C_{34}H_{20}N_4O$ cal. 500.16, found 500.16.

Synthesis Example 4: Synthesis of Compound 26

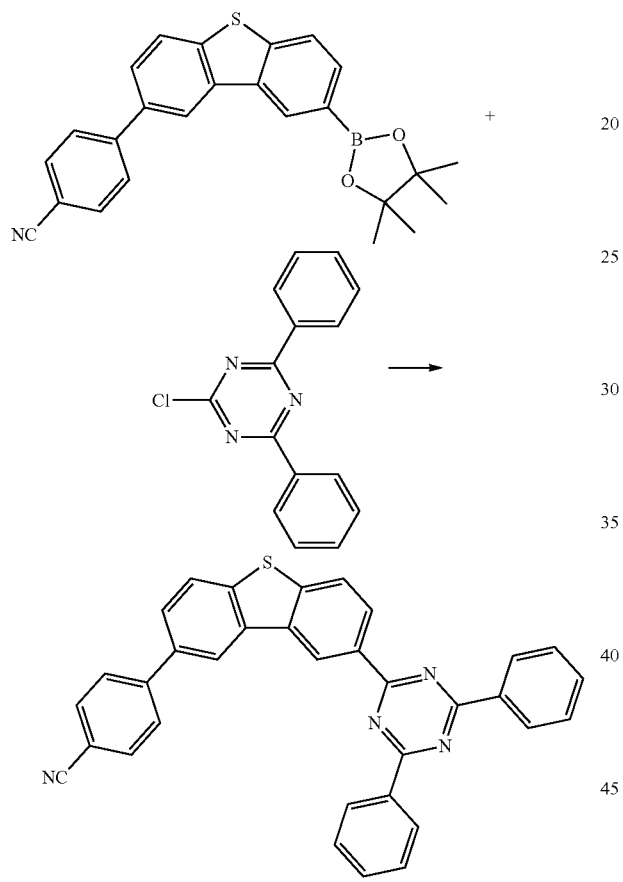

Synthesis Example 5: Synthesis of Compound 28

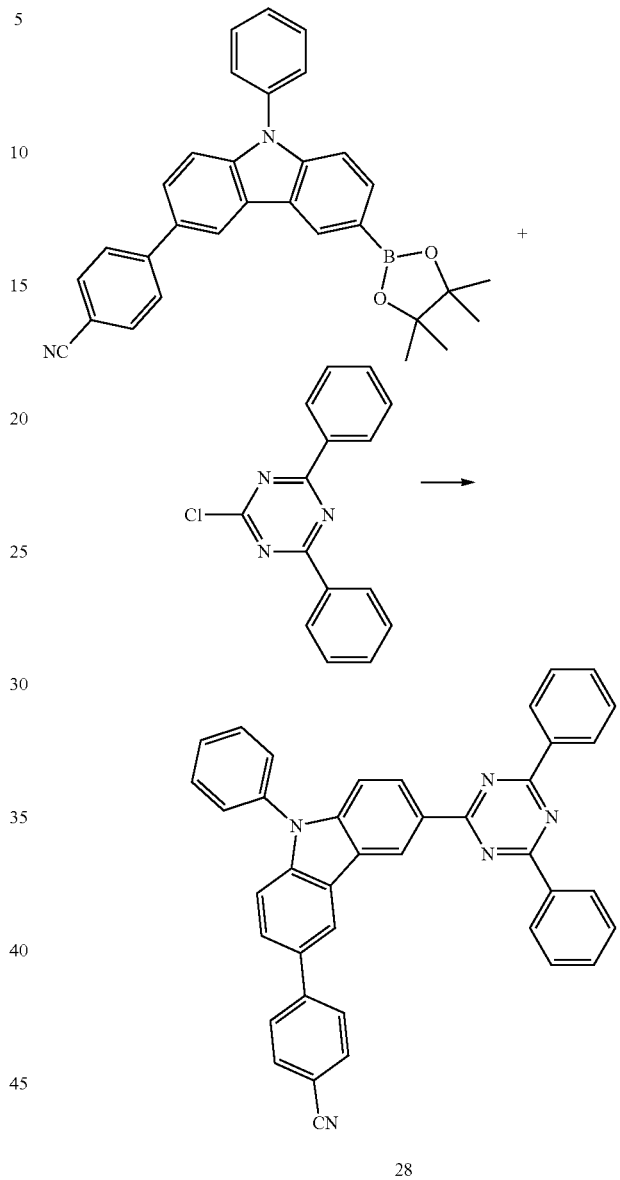

28

4.11 g (10.0 mmol) of 4-(8-(4,4,5,5-tetramethyl-1,3,2-dioxaborolan-2-yl)dibenzo[b,d]thiophen-2-yl)benzonitrile, 2.67 g (10.0 mmol) of 2-chloro-4,6-diphenyl-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 2.68 g (yield: 52%) of Compound 26. The obtained compound was identified by MS/FAB.

$C_{34}H_{20}N_4S$ cal. 516.14, found 516.15.

4.70 g (10.0 mmol) of 4-(9-phenyl-6-(4,4,5,5-tetramethyl-1,3,2-dioxaborolan-2-yl)-9H-carbazol-3-yl)benzonitrile, 2.67 g (10.0 mmol) of 2-chloro-4,6-diphenyl-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 4.37 g (yield: 76%) of Compound 28. The obtained compound was identified by MS/FAB.

$C_{40}H_{25}N_5$ cal. 575.21, found 575.22.

Synthesis Example 6: Synthesis of Compound 31

Synthesis Example 7: Synthesis of Compound 45

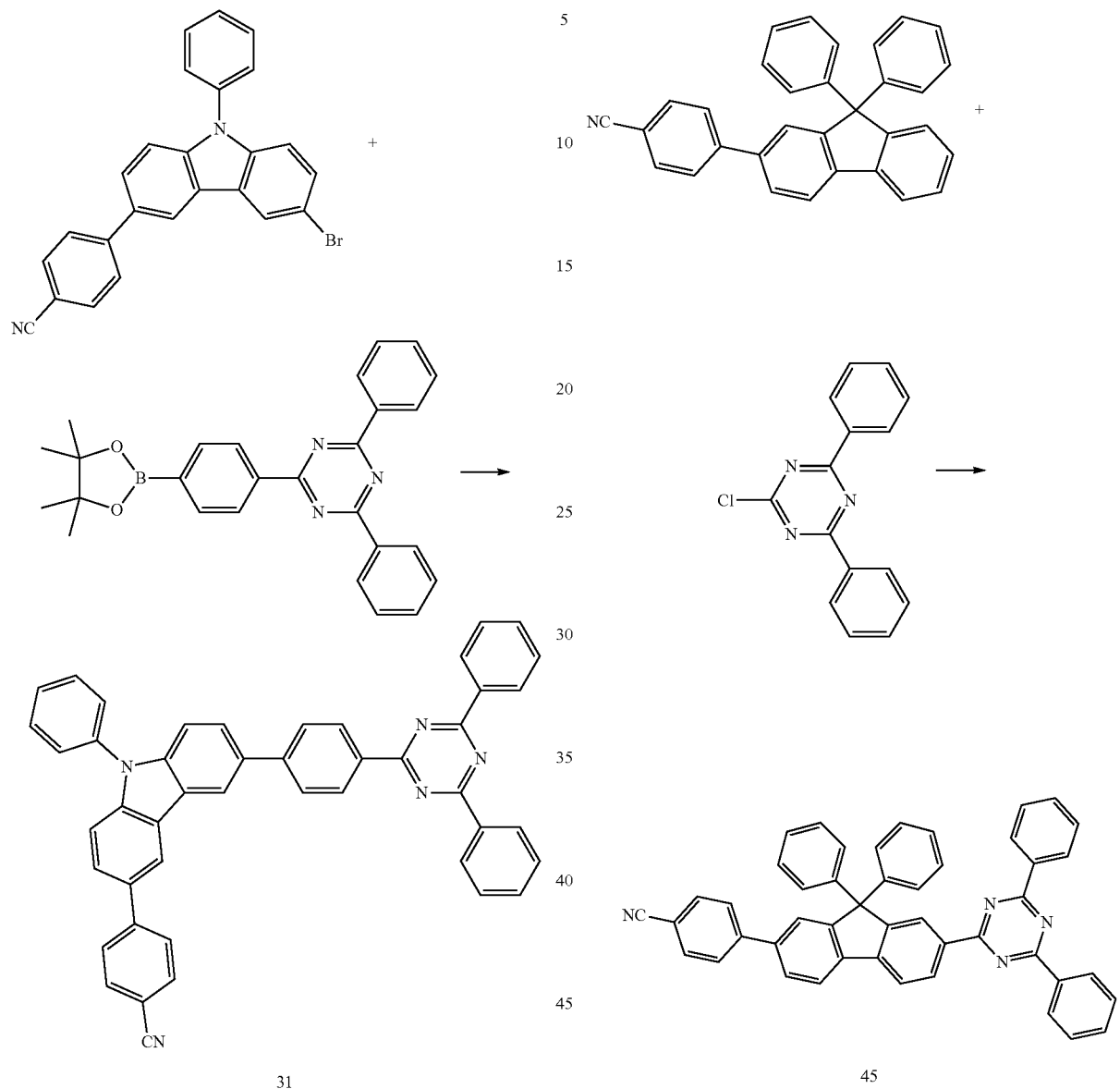

31

45

4.22 g (10.0 mmol) of 4-(6-bromo-9-phenyl-9H-carbazol-3-yl)benzonitrile, 4.35 g (10.0 mmol) of 2,4-diphenyl-6-(4-(4,4,5,5-tetramethyl-1,3,2-dioxaborolan-2-yl)phenyl)-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 4.59 g (yield: 70%) of Compound 31. The obtained compound was identified by MS/FAB.

C$_{46}$H$_{29}$N$_5$ cal. 651.24, found 651.23.

4.19 g (10.0 mmol) of 4-(9,9-diphenyl-9H-fluoren-2-yl)benzonitrile, 2.67 g (10.0 mmol) of 2-chloro-4,6-diphenyl-1,3,5-triazine, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 3.71 g (yield: 57%) of Compound 45. The obtained compound was identified by MS/FAB.

C$_{47}$H$_{30}$N$_4$ cal. 650.25, found 650.26.

Synthesis Example 8: Synthesis of Compound 54

Synthesis Example 9: Synthesis of Compound 70

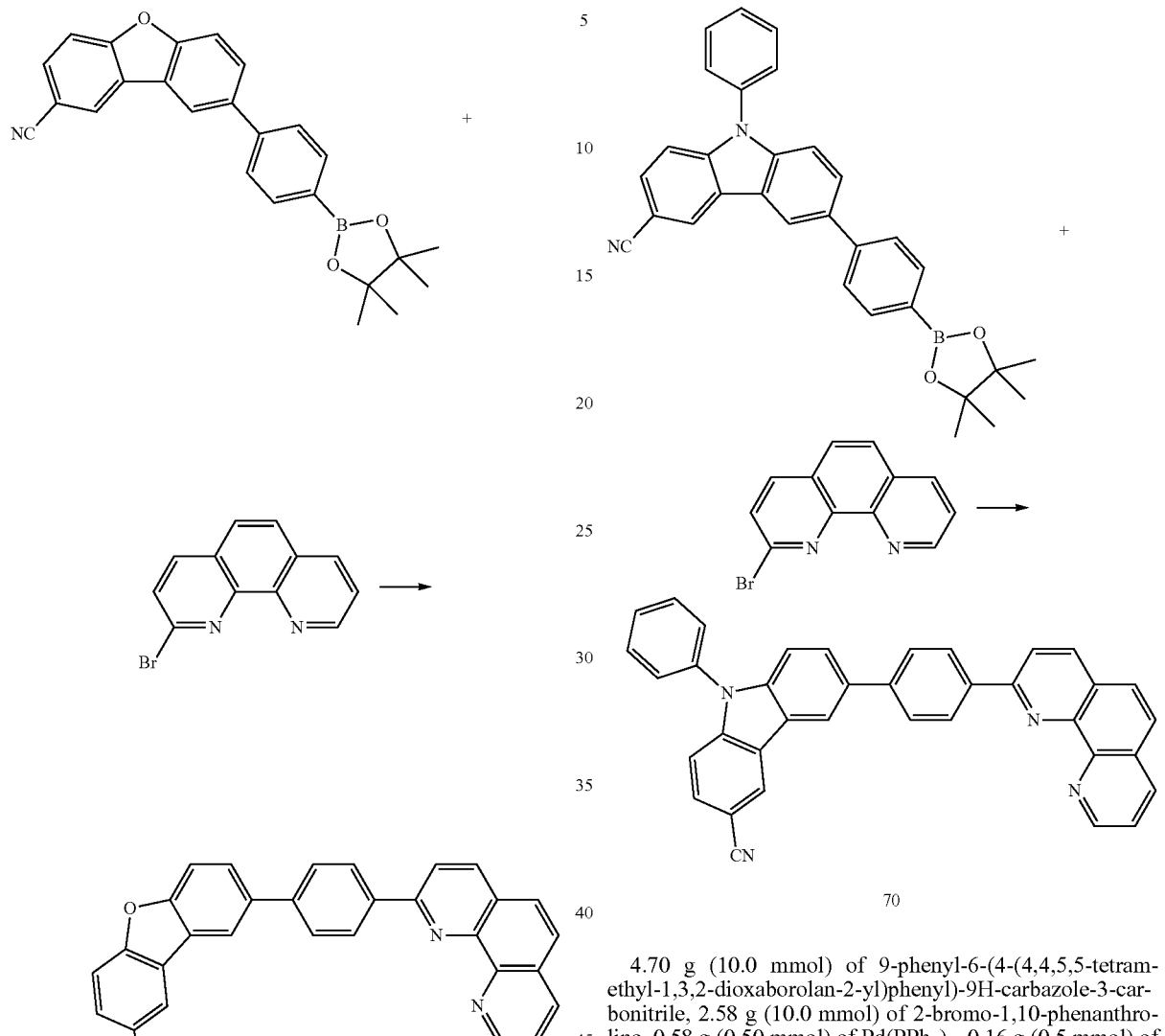

3.95 g (10.0 mmol) of 8-(4-(4,4,5,5-tetramethyl-1,3,2-dioxaborolan-2-yl)phenyl)dibenzo[b,d]furan-2-carbonitrile, 2.58 g (10.0 mmol) of 2-bromo-1,10-phenanthroline, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 2.28 g (yield: 51%) of Compound 54. The obtained compound was identified by MS/FAB.

C$_{31}$H$_{17}$N$_3$O cal. 447.14, found 447.13.

4.70 g (10.0 mmol) of 9-phenyl-6-(4-(4,4,5,5-tetramethyl-1,3,2-dioxaborolan-2-yl)phenyl)-9H-carbazole-3-carbonitrile, 2.58 g (10.0 mmol) of 2-bromo-1,10-phenanthroline, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 3.39 g (yield: 65%) of Compound 70. The obtained compound was identified by MS/FAB.

C$_{37}$H$_{22}$N$_4$ cal. 447.14, found 447.13.

Synthesis Example 10: Synthesis of Compound 82

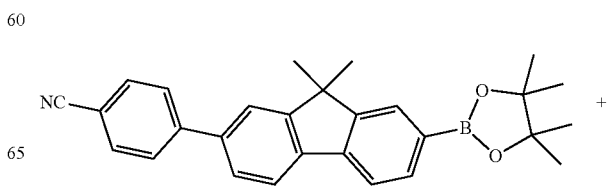

-continued

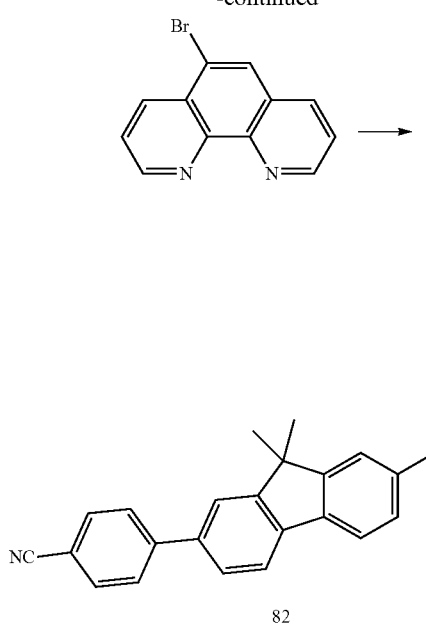

82

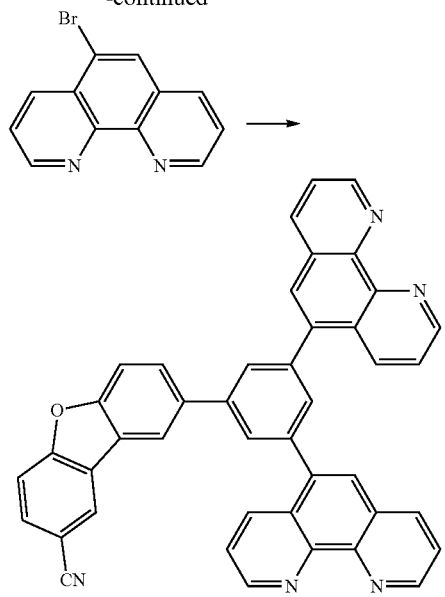

95

4.21 g (10.0 mmol) of 4-(9,9-dimethyl-7-(4,4,5,5-tetramethyl-1,3,2-dioxaborolan-2-yl)-9H-fluoren-2-yl)benzonitrile, 2.58 g (10.0 mmol) of 5-bromo-1,10-phenanthroline, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 2.84 g (yield: 60%) of Compound 82. The obtained compound was identified by MS/FAB.

C$_{34}$H$_{23}$N$_3$ cal. 473.19, found 473.20.

Synthesis Example 11: Synthesis of Compound 95

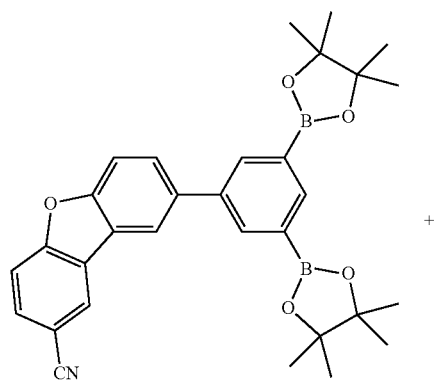

+

5.21 g (10.0 mmol) of 8-(3,5-bis(4,4,5,5-tetramethyl-1,3,2-dioxaborolan-2-yl)phenyl)dibenzo[b,d]furan-2-carbonitrile, 2.58 g (10.0 mmol) of 5-bromo-1,10-phenanthroline, 0.58 g (0.50 mmol) of Pd(PPh$_3$)$_4$, 0.16 g (0.5 mmol) of TBAB, and 3.18 g (30.0 mmol) of Na$_2$CO$_3$ were dissolved in 60 mL of a mixed solution of toluene/ethanol/H$_2$O (3/3/1), and then, stirred at a temperature of 80° C. for 16 hours. The reaction solution was cooled to room temperature, and an extraction process was performed thereon three times by using 60 mL of water and 60 mL of diethylether. An organic layer obtained therefrom was dried by using magnesium sulfate, and a residue obtained by evaporating the solvent was separated and purified by silica gel chromatography, thereby obtaining 3.25 g (yield: 52%) of Compound 95. The obtained compound was identified by MS/FAB.

C$_{43}$H$_{23}$N$_5$O cal. 625.19, found 625.20.

Embodiments of the compounds other than the compounds synthesized according to Synthesis Examples 1 to 11 could be readily recognized by one of ordinary skill in the art by referring to the above-described synthesis routes and raw materials.

Example 1

As an anode, a Corning glass substrate, on which 15 Ω/cm$^2$ (1,200 Å) ITO was formed, was cut into a size of 50 mm×50 mm×0.7 mm, sonicated with isopropyl alcohol and pure water each for 5 minutes, and then, cleaned by exposure to ultraviolet rays and ozone for 30 minutes. Then, the glass substrate was provided to a vacuum deposition apparatus.

First, 2-TNATA, which is a known material, was vacuum-deposited on the substrate to form a hole injection layer having a thickness of 600 Å. Then, 4,4'-bis[N-(1-naphthyl)-N-phenylamino]biphenyl (hereinafter, referred to as NPB), which is a known hole transporting compound, was vacuum-deposited on the hole injection layer to form a hole transport layer having a thickness of 300 Å.

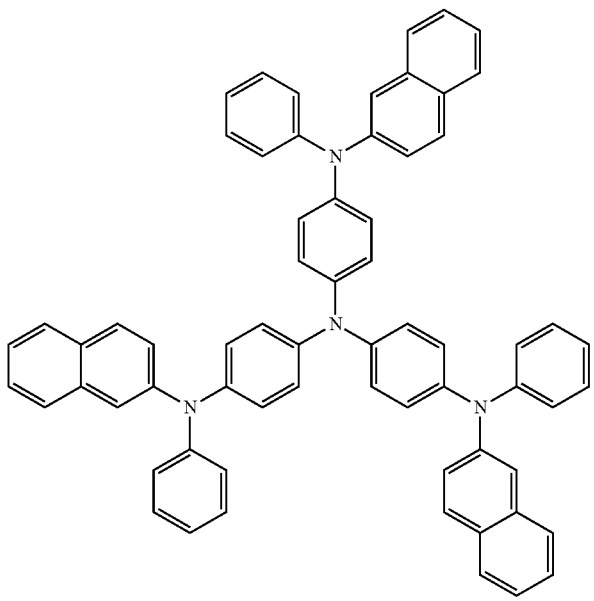

2-TNATA

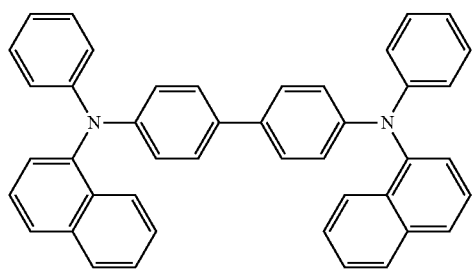

NPB

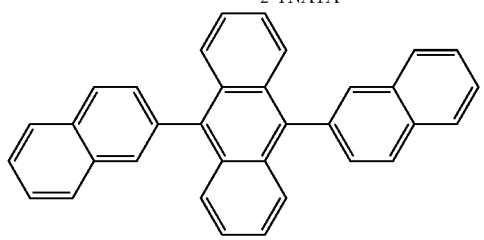

ADN

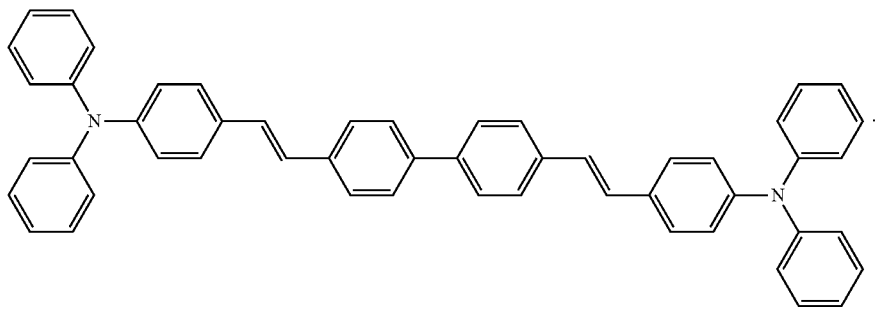

DPAVBi 9,10-di-naphthalene-2-yl-anthracene (hereinafter, referred to as ADN), which is a known compound as a blue fluorescent host, was formed on the hole transport layer, and 4,4'-bis[2-(4-(N,N-diphenylamino)phenyl)vinyl]biphenyl (hereinafter, referred to as DPAVBi), which is a known compound as a blue fluorescent dopant, were co-deposited at a weight ratio of 98:2 on the hole transport layer to form an emission layer having a thickness of 300 Å.

Next, Compound 2 of the present disclosure was deposited on the emission layer to form an electron transport layer having a thickness of 300 Å, and LiF, which is a halogenated alkali metal, was deposited on the electron transport layer to form an electron injection layer having a thickness of 10 Å. Al was then vacuum-deposited on the electron injection layer to form a LiF/Al electrode having a thickness of 3,000 Å (cathode electrode), thereby completing the manufacture of an organic light-emitting device.

Examples 2 to 11, and Comparative Example 1 to 6

Organic light-emitting devices were manufactured substantially in substantially the same manner as in Example 1, except that Compounds shown in Table 1 were each used instead of Compound 2 in forming an electron transport layer.

The driving voltage, luminance, efficiency (cd/A), and half lifespan of the organic light-emitting devices manufactured according to Examples 1 to Example 11 and Comparative Examples 1 to 6 at a current density of 50 mA/cm$^2$ were measured, and results thereof are shown in Table 1.

TABLE 1

| | Material | Driving voltage (V) | Current density (mA/cm$^2$) | Brightness (cd/m$^2$) | Efficiency (cd/A) | Emission color | Half lifespan (hr @ 100 mA/cm$^2$) |
|---|---|---|---|---|---|---|---|
| Example 1 | Compound 2 | 3.55 | 50 | 3,750 | 7.50 | Blue | 702 hr |
| Example 2 | Compound 10 | 3.15 | 50 | 3,790 | 7.58 | Blue | 707 hr |
| Example 3 | Compound 16 | 3.23 | 50 | 3,810 | 7.62 | Blue | 713 hr |
| Example 4 | Compound 26 | 3.21 | 50 | 3,810 | 7.62 | Blue | 763 hr |
| Example 5 | Compound 28 | 3.20 | 50 | 3,830 | 7.66 | Blue | 733 hr |
| Example 6 | Compound 31 | 3.18 | 50 | 3,825 | 7.65 | Blue | 725 hr |
| Example 7 | Compound 45 | 3.22 | 50 | 3,760 | 7.52 | Blue | 757 hr |
| Example 8 | Compound 54 | 3.35 | 50 | 3,800 | 7.60 | Blue | 722 hr |
| Example 9 | Compound 70 | 3.30 | 50 | 3,755 | 7.51 | Blue | 738 hr |
| Example 10 | Compound 82 | 3.26 | 50 | 3,705 | 7.41 | Blue | 710 hr |
| Example 11 | Compound 95 | 3.20 | 50 | 3,730 | 7.46 | Blue | 723 hr |
| Comparative Example 1 | Compound 200 | 4.28 | 50 | 3,250 | 6.50 | Blue | 485 hr |
| Comparative Example 2 | Compound A | 4.05 | 50 | 3,200 | 6.50 | Blue | 317 hr |
| Comparative Example 3 | Compound B | 4.12 | 50 | 3,050 | 6.50 | Blue | 538 hr |
| Comparative Example 4 | Compound C | 3.87 | 50 | 3,285 | 6.50 | Blue | 512 hr |
| Comparative Example 5 | Compound D | 4.80 | 50 | 3,110 | 6.50 | Blue | 286 hr |
| Comparative Example 6 | Compound E | 3.97 | 50 | 3,350 | 6.50 | Blue | 587 hr |

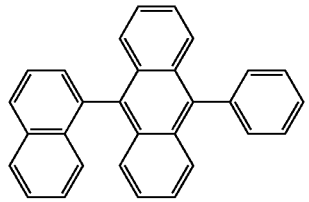

200

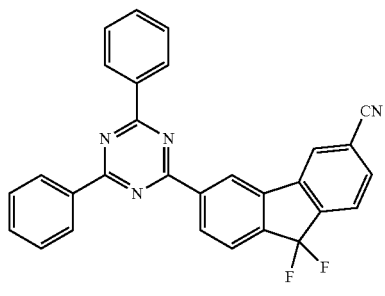

A

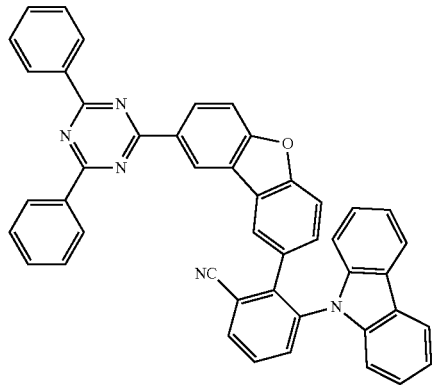

B

TABLE 1-continued

| Material | Driving voltage (V) | Current density (mA/cm$^2$) | Brightness (cd/m$^2$) | Efficiency (cd/A) | Emission color | Half lifespan (hr @ 100 mA/cm$^2$) |
|---|---|---|---|---|---|---|

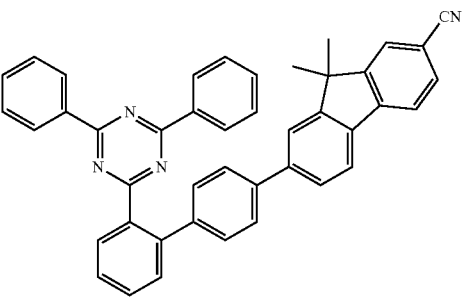

C

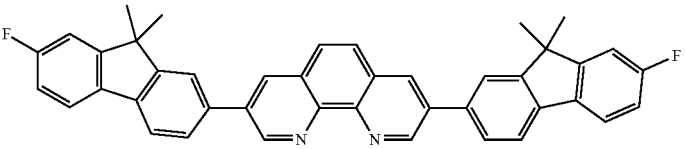

D

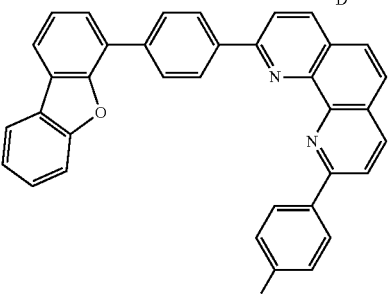

E

Referring to Table 1, it was confirmed that the organic light-emitting devices using, as an electron transporting material, the compound of the present disclosure exhibited lowered driving voltage, excellent I-V-L characteristics with significantly improved efficiency, and excellent effect in the lifespan improvement, as compared with the organic light-emitting devices of Comparative Examples 1 to 6 using Compound 200 and Compounds A to E.

According to the one or more embodiments of the present disclosure, it is confirmed that, when the compound of the present disclosure is used as an electron transporting material in a device, such a device exhibits excellent effects in terms of driving voltage, luminance, efficiency, and lifespan.

Such an organic light-emitting device may accordingly have low driving voltage, high efficiency, and long lifespan.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While the subject matter of the present disclosure has been particularly shown and described with reference to exemplary embodiments thereof, it will be understood by those of ordinary skill in the art that various changes in form and details may be made therein without departing from the spirit and scope as defined by the following claims, and equivalents thereof.

What is claimed is:

1. A heterocyclic compound represented by Formula 1:

Formula 1

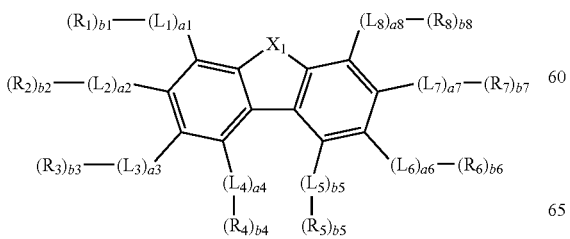

-continued

Formula 2-2

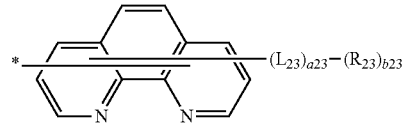

wherein, in Formulae 1, and 2-2, $X_1$ is selected from $N(R_{15})$, O, and S, $L_1$ to $L_8$ and $L_{23}$ are each independently a single bond, a substituted or unsubstituted $C_3$-$C_{60}$ carbocyclic group or a substituted or unsubstituted $C_1$-$C_{60}$ heterocyclic group, a1 to a8 and a23 are each independently an integer of 1 to 5, wherein, when a1 is two or more, two more of $L_1$(s) may be identical to or different from each other, when a2 is two or more, two more of $L_2$(s) may be identical to or different from each other, when a3 is two or more, two more of L(s) may be identical to or different from each other, when a4 is two or more, two more of $L_4$(s) may be identical to or different from each other, when a5 is two or more, two more of $L_5$(s) may be identical to or different from each other, when a6 is two or more, two more of L(s) may be identical to or different from each other, when a7 is two or more, two more of $L_7$(s) may be identical to or different from each other, when a8 is two or more, two more of $L_8$(s) may be identical to or different from each other, and when a23 is two or more, two more of $L_{23}$(s) may be identical to or different from each other, $R_1$ to $R_8$ and $R_{15}$ are each independently selected from a group represented by Formula 2-2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q₁)(Q₂)(Q₃), —N(Q₁)(Q₂), —B(Q₁)(Q₂), —C(═O)(Q₁), —S(═O)₂(Q₁), and —P(═O)(Q₁)(Q₂), at least one selected from $R_1$ to $R_8$ is a cyano group, at least one of the remaining $R_1$ to $R_8$ is a group represented by a group represented by Formula 2-2, wherein the $L_1$ to $L_8$ corresponding to the at least one selected from $R_1$ to $R_8$ that is a cyano group is a single bond, wherein the $L_1$ to $L_8$ corresponding to the at least one selected from $R_1$ to $R_8$ that is a group represented by Formula 2-2 is not an anthracene group or a triazine group, $R_{23}$ is selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $R_{23}$ is not a cyano group, b1 to b8 and b23 are each independently an integer of 1 to 5, wherein, when b1 is two or more, two more of $R_1$(s) may be identical to or different from each other, when b2 is two or more, two more of $R_2$(s) may be identical to or different from each other, when b3 is two or more, two more of $R_3$(s) may be identical to or different from each other, when b4 is two or more, two more of $R_4$(s) may be identical to or different from each other, when b5 is two or more, two more of $R_5$(s) may be identical to or different from each other, when b6 is two or more, two more of $R_6$(s) may be identical to or different from each other, when b7 is two or more, two more of $R_7$(s) may be identical to or different from each other, when b8 is two or more, two more of $R_8$(s) may be identical to or different from each other, and when b23 is two or more, two more of $R_{23}$(s) may be identical to or different from each other, $R_1$ to $R_8$, $R_{15}$, $R_{23}$, $L_1$ to $L_8$, and $L_{23}$ do not include a carbazole group, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The heterocyclic compound of claim 1, wherein $L_1$ to $L_8$ and $L_{23}$ are each independently selected from:

a single bond;

a benzene group, a pentalene group, an indene group, an azulene group, a heptalene group, an indacene group, an acenaphthene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an indole group, an isoindole group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a triazole group, a tetrazole group, an oxadiazole group, a triazine group, a dibenzofuran group, and a dibenzothiophene group; and a benzene group, a pentalene group, an indene group, an azulene group, a heptalene group, an indacene group, an acenaphthene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a rubicene group, a coronene group, an ovalene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an indole group, an isoindole group, an indazole group, a purine group, a quinoline group, an isoquinoline group, a benzoquinoline group, a phthalazine group, a naphthyridine group, a quinoxaline group, a quinazoline group, a cinnoline group, a carbazole group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a triazole group, a tetrazole group, an oxadiazole group, a triazine group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, and a dibenzothiophenyl group.

3. The heterocyclic compound of claim 1, wherein $R_1$ to $R_8$ may each independently be selected from:

a group represented by Formula 2-2, hydrogen, deuterium, —F, —Cl, —Br, —I, a hydroxyl group, a cyano group, a nitro group, an amidino group, a hydrazino group, a hydrazono group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, and a dibenzosilolyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, and a dibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, and a dibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are each independently selected from:

a $C_1$-$C_{20}$ alkyl group, a $C_1$-$C_{20}$ alkoxy group, a phenyl group, a biphenyl group, and a terphenyl group; and a phenyl group substituted with at least one selected from deuterium, —F, —Cl, —Br, —I, a cyano group, a $C_1$-$C_{20}$ alkyl group, and a $C_1$-$C_{20}$ alkoxy group.

4. The heterocyclic compound of claim 1, wherein $R_{23}$ is selected from:
a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, and an imidazopyridinyl group;
a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-fluorenyl group, a phenalenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a thiadiazolyl group, an imidazopyridinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $R_{23}$ does not include a cyano group.

5. The heterocyclic compound of claim 1, wherein at least one of $R_6$ and $R_7$ is a group represented by Formula 2-2, and at least one selected from $R_1$, $R_2$, $R_3$, and $R_4$ is a cyano group.

6. The heterocyclic compound of claim 1, wherein $R_6$ is a group represented by Formula 2-2, and at least one selected from $R_5$, $R_7$, and $R_8$ is a cyano group.

7. The heterocyclic compound of claim 1, wherein $R_7$ is a group represented by Formula 2-2, and at least one selected from $R_5$, $R_6$, and $R_8$ is a cyano group.

8. The heterocyclic compound of claim 1, wherein at least one selected from $R_2$, $R_3$, and $R_8$ is a cyano group.

9. The heterocyclic compound of claim 1, wherein Formula 2-2 is represented by one selected from Formulae 2-2(1) to 2-2(4):

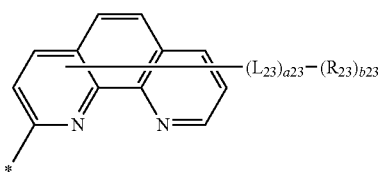

2-2(1)

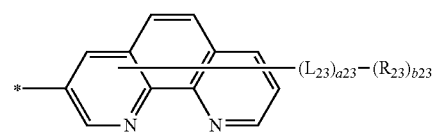

2-2(2)

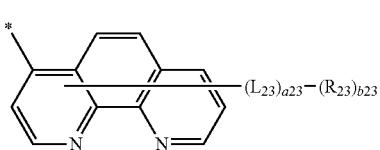

2-2(3)

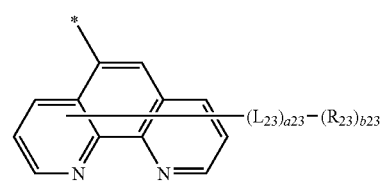

2-2(4)

wherein, in Formulae 2-2(1) to 2-2(4), $L_{23}$, a23, $R_{23}$, and b23 are the same as defined in claim 1.

10. A heterocyclic compound, wherein the heterocyclic compound is selected from Compounds 53 to 61, 70, 90 to 92, 95:
53
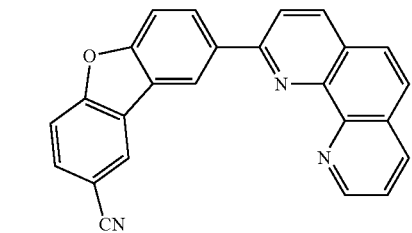
54
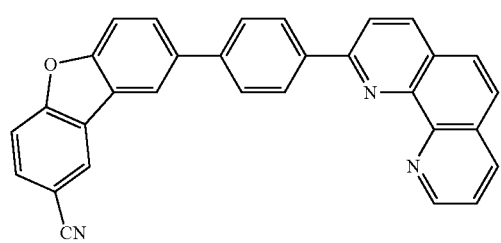
55
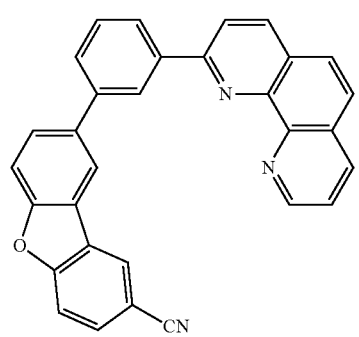
56
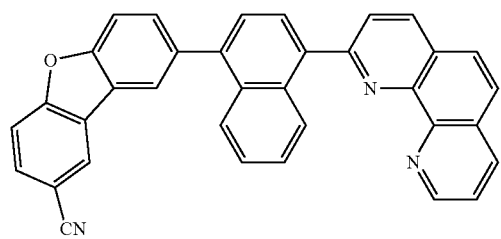
57
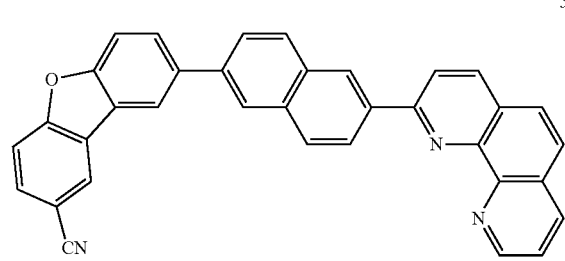
58
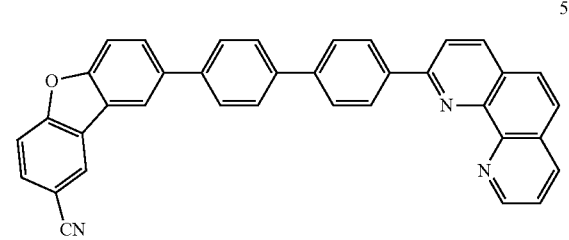
59
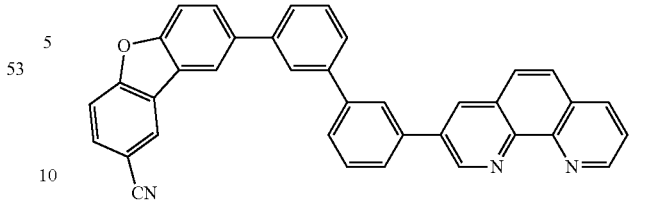
60
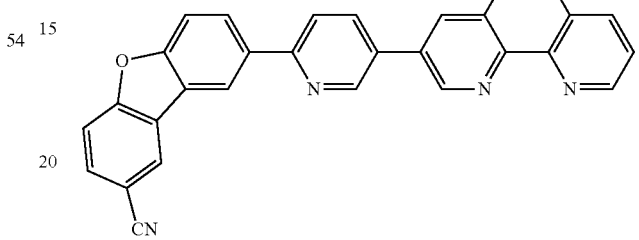
61
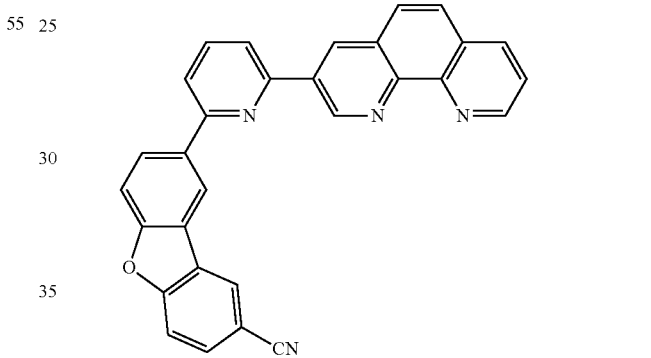
70
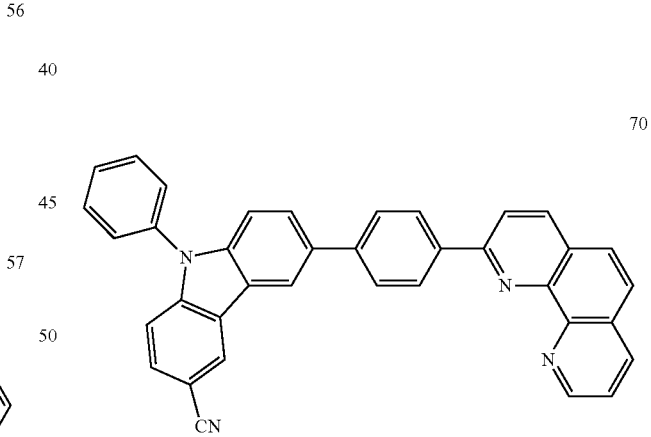
90
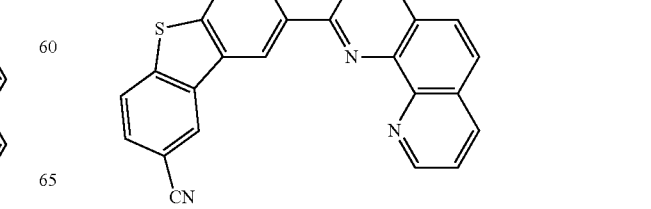

-continued

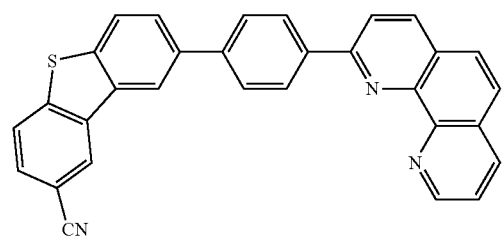

91

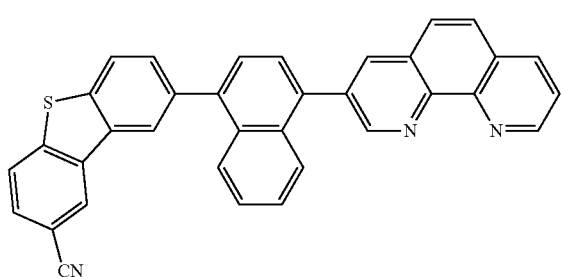

92

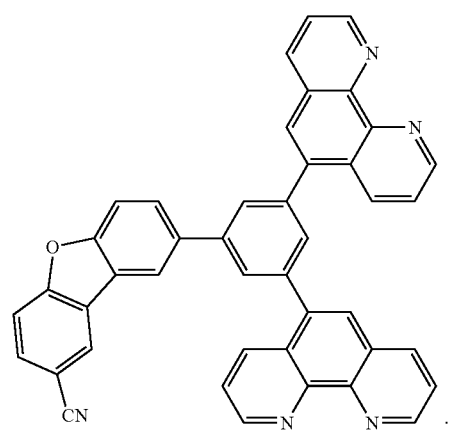

95

11. An organic light-emitting device comprising:
a first electrode;
a second electrode facing the first electrode; and
an organic layer between the first electrode and the second electrode,
wherein the organic layer comprises an emission layer and at least one of the heterocyclic compound of claim 1.

12. The organic light-emitting device of claim 11, wherein:
the first electrode is an anode,
the second electrode is a cathode, and
the organic layer comprises, i) a hole transport region between the first electrode and the emission layer and comprising a hole injection layer, a hole transport layer, a buffer layer, an electron blocking layer, or any combination thereof, and ii) an electron transport region between the emission layer and the second electrode and comprising a hole blocking layer, an electron transport layer, an electron injection layer, or any combination thereof.

13. The organic light-emitting device of claim 12, wherein the electron transport region comprises at least one of the heterocyclic compound.

14. The organic light-emitting device of claim 12, wherein the electron transport region comprises an electron transport layer and an electron injection layer,
wherein the electron transport layer comprises at least one of the heterocyclic compound.

15. The organic light-emitting device of claim 12, wherein the hole transport region comprises a p-dopant,
wherein the p-dopant comprises a cyano group-containing compound.

16. The organic light-emitting device of claim 11, wherein the emission layer comprises at least one selected from an anthracene-based compound, a pyrene-based compound, an arylamine-based compound, and a styryl-based compound.

17. The organic light-emitting device of claim 11, wherein:
the emission layer is a first color light emission layer,
the organic light-emitting device further comprises i) at least one second color light emission layer, or ii) at least one second color light emission layer and at least one third color light emission layer, between the first electrode and the second electrode,
a maximum emission wavelength of the first color light, a maximum emission wavelength of the second color light, and a maximum emission wavelength of the third color light are identical to or different from each other, and
the first color light and the second color light are emitted in the form of mixed light, or the first color light, the second color light, and the third color light are emitted in the form of mixed light.

18. An electronic apparatus comprising:
a thin film transistor comprising a source electrode, a drain electrode, an activation layer, and a gate electrode; and
the organic light-emitting device of claim 11,
wherein the first electrode of the organic light-emitting device is electrically connected to one of the source electrode and the drain electrode of the thin film transistor.

* * * * *